(12) United States Patent
Naka et al.

(10) Patent No.: US 6,232,334 B1
(45) Date of Patent: May 15, 2001

(54) BENZIMIDAZOLE DERIVATIVES, THEIR PRODUCTION AND USE

(75) Inventors: Takehiko Naka, Kobe; Kohei Nishikawa, Kyoto; Takeshi Kato, Higashiosaka, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/376,494

(22) Filed: Aug. 18, 1999

Related U.S. Application Data

(62) Division of application No. 09/280,094, filed on Mar. 29, 1999, now Pat. No. 6,004,989, which is a division of application No. 08/924,919, filed on Sep. 8, 1997, now Pat. No. 5,962,491, which is a division of application No. 08/715,100, filed on Sep. 17, 1996, now Pat. No. 5,703,110, which is a division of application No. 08/131,667, filed on Oct. 5, 1993, now Pat. No. 5,705,517, which is a division of application No. 08/058,739, filed on May 10, 1993, now Pat. No. 5,401,764, which is a division of application No. 07/997,703, filed on Jan. 5, 1993, now Pat. No. 5,328,919, which is a division of application No. 07/687,238, filed on Apr. 18, 1991, now Pat. No. 5,196,144.

(30) Foreign Application Priority Data

| | | |
|---|---|---|
| Apr. 27, 1990 | (JP) | 2-113148 |
| May 30, 1990 | (JP) | 2-141942 |
| Aug. 6, 1990 | (JP) | 2-208662 |
| Oct. 1, 1990 | (JP) | 2-264579 |
| Dec. 24, 1990 | (JP) | 2-413679 |

(51) Int. Cl.$^7$ .......... A61K 31/4184; A61P 9/12; C07D 235/26; C07D 235/28; C07D 235/30
(52) U.S. Cl. .......... 514/381; 514/382; 514/397; 514/398; 514/399; 514/400; 548/251; 548/252; 548/253; 548/304.7; 548/306.1
(58) Field of Search .......... 514/381, 382, 514/397–400; 548/251–253, 304.7, 306.1

(56) References Cited

U.S. PATENT DOCUMENTS

4,526,896  7/1985  Schevral et al. .......... 548/253

(List continued on next page.)

FOREIGN PATENT DOCUMENTS

28833  5/1981  (EP) .

(List continued on next page.)

OTHER PUBLICATIONS

Noda et al., "Inhibition of Rabbit Aortic Angiotensin II (AII) Receptor by CU–11974, A New Nonpeptide AII Antagonist", Biochem Pharm, vol. 46, No. 2, pp. 311–318 (1993).

Primary Examiner—Jane C. Osweeki
(74) Attorney, Agent, or Firm—Foley & Lardner

(57) ABSTRACT

Benzimidazole derivatives of the formula (I):

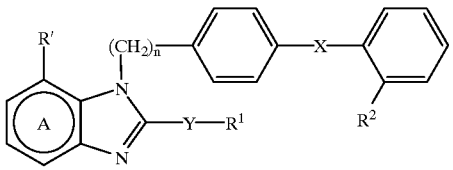

wherein the ring A is a benzene ring which may optionally contain substitution in addition to the R' group; $R^1$ is hydrogen or an optionally substituted hydrocarbon residue; $R^2$ is a group capable of forming an anion or a group convertible thereinto; X is a direct bond or a spacer having an atomic length of two or less between the phenylene group and the phenyl group; R' is carboxyl, an ester thereof, an amide thereof or a group capable of forming an anion or convertible to an anion; Y is —O—, —S(O)$_m$— or —N(R$^4$)— wherein m is an integer of 0, 1 or 2 and $R^4$ is hydrogen or an optionally substituted alkyl group; and n is an integer of 1 or 2; and the pharmaceutically acceptable salts thereof, have potent angiotensin II antagonistic activity and antihypertensive activity, thus being useful as therapeutic agents for treating circulatory system diseases such as hypertensive diseases, heart diseases, strokes, cerebral apoplexy and nephritis.

25 Claims, 3 Drawing Sheets

U.S. PATENT DOCUMENTS

| | | | | |
|---|---|---|---|---|
| 4,764,623 | 8/1988 | Kees | ............................. | 548/253 |
| 4,775,679 | 10/1988 | Chang | ............................. | 548/253 |
| 4,880,804 | 11/1989 | Carini et al. | ............................. | 514/381 |
| 5,864,043 | 1/1999 | Narr et al. | ............................. | 548/307 |

FOREIGN PATENT DOCUMENTS

| | | |
|---|---|---|
| 28834 | 5/1981 | (EP) . |
| 245637 | 11/1987 | (EP) . |
| 253310 | 1/1988 | (EP) . |
| 291969 | 11/1988 | (EP) . |
| 323841 | 7/1989 | (EP) . |
| 392317 | 10/1990 | (EP) . |
| 399732 | 11/1990 | (EP) . |
| 400835 | 12/1990 | (EP) . |
| 420237 | 4/1991 | (EP) . |

BENZIMIDAZOLE DERIVATIVES, THEIR PRODUCTION AND USE

This application is a divisional of application Ser. No. 09/280,094, filed Mar. 29, 1999, now U.S. Pat. No. 6,004, 989, which is in turn a divisional of application Ser. No. 08/924,919, filed Sep. 8, 1997, now U.S. Pat. No. 5,462,481 which is in turn a divisional of application Ser. No. 08/715, 100, filed Sep. 17, 1996 now U.S. Pat. No. 5,703,110, which is in turn a divisional of application Ser. No. 08/131,667, filed Oct. 5, 1993, now U.S. Pat. No. 5,705,517, which is in turn a divisional of application Ser. No. 08/058,739, filed May 10, 1993, now U.S. Pat. No. 5,401,764, which is in turn is a divisional of Ser. No. 07/997,703, filed Jan. 5. 1993, now U.S. Pat. No. 5,328,919, which is in turn a divisional of Ser. No. 07/687,238, filed Apr. 18, 1991, now U.S. Pat. No. 5,196,144.

FIELD OF THE INVENTION

The present invention relates to novel benzimidazole derivatives having potent pharmacological actions and intermediates for the preparation thereof. More particularly, the present invention relates to compounds having potent anti-hypertensive activity and strong angiotensin II antagonistic activity, which are useful as therapeutic agents for treating circulatory diseases such as hypertensive diseases, heart diseases (e.g. hypercardia, heart failure, cardiac infarction, etc.), strokes, cerebral apoplexy, nephritis, etc.

BACKGROUND OF THE INVENTION

The renin-angiotensin system is involved in the homeostatic function to control systemic blood pressure, the volume of body fluid, balance among the electrolytes, etc., associated with the aldosterone system. Development of angiotensin II converting enzyme inhibitors (ACE inhibitor) (this converting enzyme produces angiotensin II which possesses a strong vasoconstrictive action) has clarified the relation between the renin-angiotensin system and hypertension. Since angiotensin II constricts blood vessel to elevate blood pressure via the angiotensin II receptors on the cellular membranes, angiotensin II antagonists, like the ACE inhibitor, wouLd be useful in treating hypertension caused by angiotensin.

It has been reported that various angiotensin II analogues such as saralasin, [Sar$^1$,Ile$^8$]A II, and the like, possess potent angiotensin II antagonist activity.

It has, however, been reported that, when peptide antagonists are administered parenterally, their actions are not prolonged and, when administered orally, they are ineffective (M. A. Ondetti and D. W. Cushman, Annual Reports in Medicinal Chemistry, 13, 82–91 (1978)).

It would be highly desirable to develop a non-peptide angiotensin II antagonist which overcomes these drawbacks. In the earliest studies in this field, imidazole derivatives having angiotensin II antagonist activity have been disclosed in Japanese Patent Laid Open No. 71073/1981; No. 71074/ 1981; No. 92270/1982; No. 157768/1983; U.S. Pat. Nos. 4,355,040, 4,355,040, etc. Later, improved imidazole derivatives are disclosed in European Patent Laid Open No. 0253310, No. 0291969, No. 0324377, Japanese Patent Laid Open No. 23868/1988; and No. 117876/1989. Further, pyrole, pyrazole, and triazole derivatives are disclosed as angiotensin II antagonists in European Patent Laid Open No. 0323841, and Japanese Patent Laid Open No. 287071/1989.

U.S. Pat. No. 4,880,804 discloses benzimidazole derivatives having an angiotensin II receptor antagonistic action, which are intravenously active in vivo in rats with renal hypertension. Examples of such benzimidazole derivatives are those represented by the following formula (A):

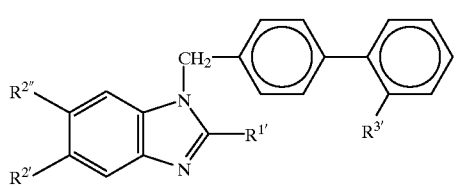

(A)

wherein substituents, for example, in the 5- and/or 6-position are hydroxymethyl, methoxy, formyl, chloro, or carboxy. Although most compounds among those exemplified are orally inactive, it is said that only the 6-hydroxymethyl and 6-chloro compounds are orally effective (100 mg/kg or less). It is, however, believed that the activity of even these disclosed compounds is insufficient for clinical uses.

SUMMARY OF THE INVENTION

The present invention provides novel benzimidazole derivatives having potent anti-hypertensive activity and strong angiotensin II antagonistic action, which are of practical value in clinical use as therapeutic agents.

The present inventors considered that compounds functioning to control the renin-angiotensin system as well as clinically useful for the treatment of circulatory diseases such as hypertensive diseases, heart diseases (e.g. hypercardia, heart failure, cardiac infarction, etc.), strokes, cerebral apoplexy, etc. are required to have potent angiotensin II receptor antagonistic activity and to exert strong oral and long-lasting angiotensin II antagonist action. Extensive investigations were made based on those consideration. As a result of this research, the present inventors have succeeded in synthesizing novel 2-substituted benzimidazole derivatives (I) possessing highly angiotensin II receptor antagonistic activity as well as exerting strong oral and long-lasting angiotensin II antagonistic and anti-hypertensive action and developed the present invention.

The present invention relates to benzimidazole derivatives having the formula I:

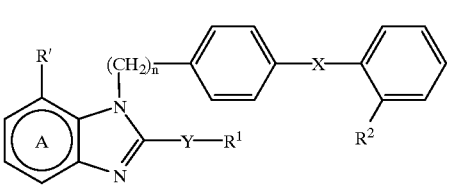

(I)

wherein the ring A is a benzene ring which may optionally contain substitution in addition to the R' group; $R^1$ is hydrogen or an optionally substituted hydrocarbon residue; $R^2$ is a group capable of forming an anion or a group convertible thereinto; X is a direct bond or a spacer having an atomic length of two or less between the phenylene group and the phenyl group; R' is carboxyl, an ester thereof, an amide thereof or a group capable of forming an anion or convertible to an anion; Y is —O—, —S(O)$_m$— or —N(R$^4$)— wherein m is an integer of 0, 1 or 2 and $R^4$ is hydrogen or an optionally substituted alkyl group; and n is an integer of 1 or 2; and the pharmaceutically acceptable salts thereof.

These compounds are unexpectedly potent angiotensin II antagonists which are of value in the treatment of circulatory system diseases such as hypertensive diseases, heart diseases, strokes, nephritis, etc.

Another aspect of the present invention relates to pharmaceutical compositions comprising an effective amount of the benzimidazole derivative having the formula I and a pharmaceutically acceptable carrier useful in treating circulatory system diseases such as hypertensive diseases, heart diseases, strokes, renal failure, nephritis, etc., and processes for preparing such compounds and compositions.

Still another aspect of the present invention relates to a method for treating said circulatory system diseases of animals, which comprises administering an effective amount of the benzimidazole derivatives having the formula I or the pharmaceutical composition thereof to said animal.

DETAILED DESCRIPTION OF THE INVENTION

Figure 1:
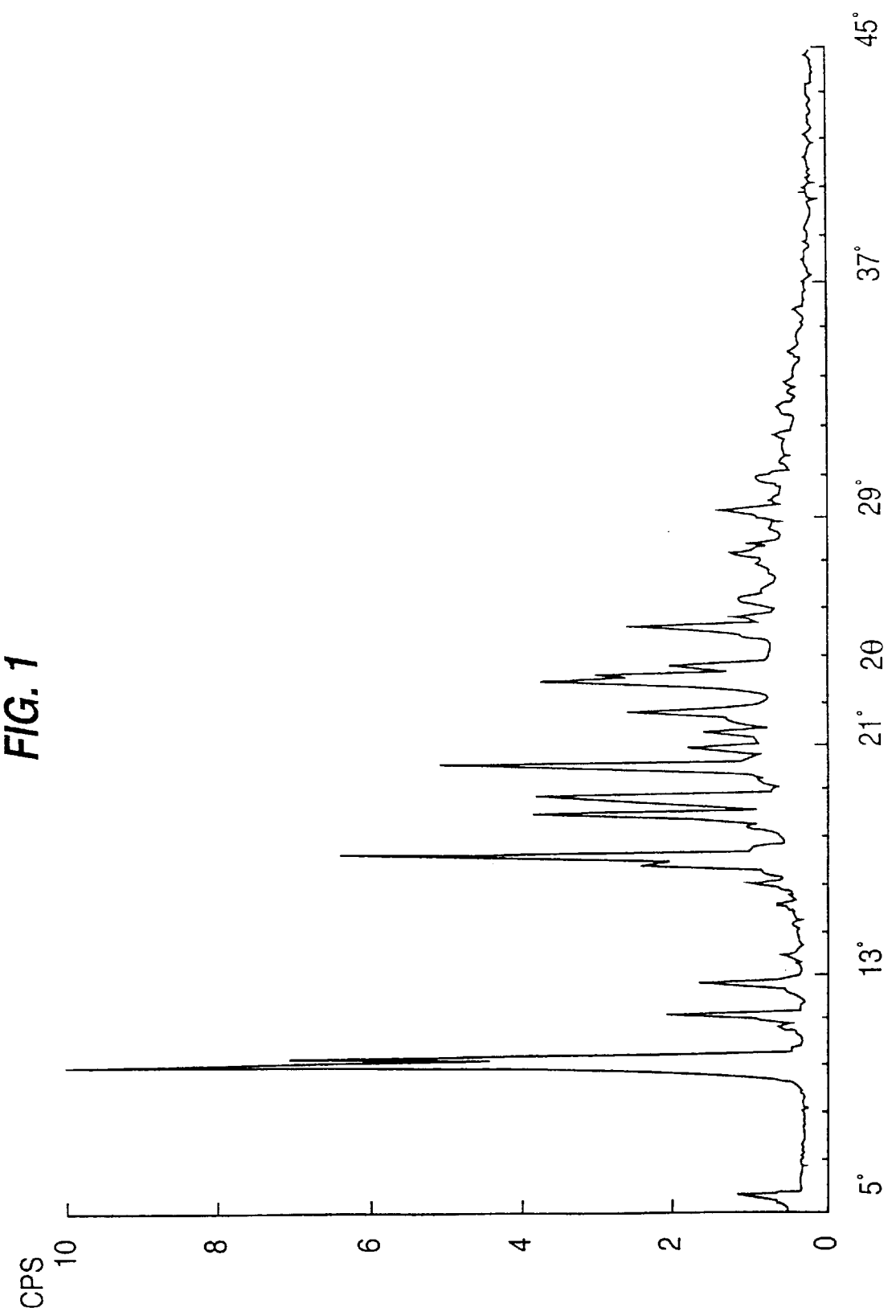
FIG. 1 depicts a X ray scattering chart obtained in Experimental Example 1.

The present invention provides the benzimidazole derivatives (I) and the pharmaceutically acceptable salts thereof, which possess strong angiotensin II antagonist activity and are of value in the treatment of circulatory diseases such as hypertensive diseases, heart diseases, strokes, cerebral diseases, nephritis, etc., pharmaceutical compositions comprising an effective amount of the benzimidazole derivative having the formula I and a pharmaceutically acceptable carrier useful in treating said circulatory diseases, and processes for preparing such compounds and compositions.

The present invention further provides a method for treating said circulatory system diseases of animals, which comprises administering an effective amount of the benzimidazole derivative (I) or the pharmaceutical composition thereof to said animal.

An important group of compounds according to the present invention are the compounds of the formula I″:

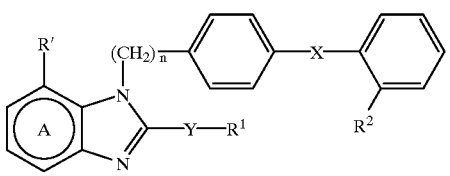

(I″)

wherein the ring A is a benzene ring which may optionally contain substitution in addition to the R' group; $R^1$ is hydrogen or an optionally substituted hydrocarbon residue; $R^2$ is a group capable of forming an anion or a group convertible thereinto; X is a direct bond or a spacer having an atomic length of two or less between the phenylene group and the phenyl group; R' is carboxyl, an ester thereof or an amide thereof ; Y is —O—, —S(O)$_m$— or —N(R$^4$)— wherein m is an integer of 0, 1 or 2 and $R^4$ is hydrogen or an optionally substituted alkyl group; and n is an integer of 1 or 2; and the pharmaceutically acceptable salts thereof.

With regard to the foregoing formula (I), hydrocarbon residues for $R^1$ include, for example, alkyl, alkenyl, alkynyl, cycloalkyl, aryl, and aralkyl groups. Among them, alkyl, alkenyl, and cycloalkyl groups are preferable.

Alkyl groups for $R^1$ are lower alkyl groups having 1 to about 8 carbon atoms, which may be straight or branched, and include, for example, methyl, ethyl, propyl, isopropyl, butyl, isobutyl, sec-butyl, t-butyl, pentyl, i-pentyl, hexyl, heptyl, octyl, and the like.

Alkenyl groups for $R^1$ are lower alkenyl groups having 2 to about 8 carbon atoms, which may be straight or branched, and include, for example, vinyl, propenyl, 2-butenyl, 3-butenyl, isobutenyl, octenyl, and the like.

Alkynyl groups for $R^1$ are lower alkynyl groups having 2 to about 8 carbon atoms, which may be straight or branched, and include, for example, ethynyl, 2-propynyl, 2-butynyl, 2-pentynyl, 2-octynyl, and the like.

Cycloalkyl groups for $R^1$ are lower cycloalkyl groups having 3 to about 6 carbon atoms, and include, for example, cyclopropyl, cyclobutyl, cyclopentyl, and the like.

The above-mentioned alkyl, alkenyl, alkynyl, and cycloalkyl groups may be substituted with hydroxyl, an optionally substituted amino group (e.g. amino, methylamino, etc.), halogen, a lower ($C_{1-4}$) alkoxy group or the like.

Aralkyl groups for $R^1$ include, for example, phenyl-lower ($C_{1-4}$) alkyl such as benzyl, phenethyl, and the like, and the aralkyl group may be substituted with, for example, halogen (e.g. F, Cl, Br, etc.), nitro, lower ($C_{1-4}$) alkoxy (e.g. methoxy, ethoxy, etc.), lower ($C_{1-4}$) alkyl (e.g. methyl, ethyl, etc.), or the like at various positions of the benzene ring.

Aryl groups for $R^1$ include, for example, phenyl and the aryl group may be substituted with, for example, halogen (e.g. F, Cl, Br, etc.), nitro, lower ($C_{1-4}$) alkoxy (e.g. methoxy, ethoxy, etc.), lower ($C_{1-4}$) alkyl (e.g. methyl, ethyl, etc.), or the like at various positions of the benzene ring.

Among the above-mentioned groups for $R^1$, preferred examples are optionally substituted alkyl and alkenyl groups (e.g. lower ($C_{1-5}$) alkyl and lower ($C_{2-5}$) alkenyl groups optionally substituted with hydroxyl, an amino group, halogen or a lower ($C_{1-4}$) alkoxy group).

Examples of groups capable of forming an anion and groups convertible thereinto for $R^2$ include carboxyl, tetrazolyl, trifluoromethanesulfonic amide (—NHSO$_2$CF$_3$), phosphoric acid, sulfonic acid, cyano, lower ($C_{1-4}$) alkoxycarbonyl, and the like. These groups may be protected with, for example, an optionally substituted lower alkyl group (e.g. lower ($C_{1-4}$) alkoxymethyl, optionally substituted arylmethyl, etc.) or an acyl group (e.g. lower ($C_{2-5}$) alkanoyl, optionally substituted benzoyl, etc.). Such groups may include those which are capable of forming anions or convertible thereinto either chemically or under biological and/or physiological conditions (for example, in vivo reaction such as oxidation-reduction or hydrolysis catalyzed by in vivo enzymes).

The compounds wherein $R^2$ is a group capable of forming an anion or convertible thereinto chemically (e.g. by oxidation, reduction or hydrolysis) (for example, an optionally protected tetrazolyl group (e.g. a group having the formula:

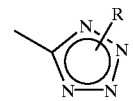

wherein R is methyl, triphenylmethyl, 2-tetrahydropyranyl, tert-butyl, methoxymethyl, ethoxymethyl, or optionally substituted benzyl such as p-methoxybenzyl and p-nitrobenzyl), cyano and the like), are useful as synthetic intermediates.

Among the above-mentioned groups for $R^2$, preferred examples are tetrazolyl groups optionally protected with optionally substituted lower alkyl or acyl, carboxyl groups optionally protected with optionally substituted lower alkyl, and trifluoromethanesulfonic amide.

Examples of carboxyl, esters thereof or amides thereof for R' include, for example, groups having the formula: —CO—D' wherein D' is hydroxyl, optionally substituted amino (e.g. amino, N-lower ($C_{1-4}$) alkylamino, N,N-dilower ($C_{1-4}$) alkyl amino, etc.), or optionally substituted alkoxy [e.g. lower ($C_{1-4}$) alkoxy optionally substituted with hydroxyl, optionally substituted amino (e.g. amino, dimethylamino, diethylamino, piperidino, morpholino, etc.), halogen, lower ($C_{1-6}$) alkoxy, lower ($C_{1-6}$) alkylthio or optionally substituted dioxolenyl (e.g. 5-methyl-2-oxo-1,3-dioxolen-4-yl, etc.) on the alkyl moiety and groups having the formula: —OCH($R^7$)OCOR$^8$ wherein $R^7$ is hydrogen, straight or branched lower alkyl having 1 to 6 carbon atoms (e.g. methyl, ethyl, n-propyl, isopropyl, n-butyl, isobutyl, t-butyl, n-pentyl, isopentyl, neopentyl, etc.), or cycloalkyl having 5 to 7 carbon atoms (e.g. cyclopentyl, cyclohexyl, cycloheptyl, etc.) and $R^8$ is straight or branched lower alkyl having 1 to 6 carbon atoms (e.g. methyl, ethyl, n-propyl, isopropyl, n-butyl, isobutyl, sec-butyl, t-butyl, n-pentyl, isopentyl, neopentyl, etc.), straight or branched lower alkenyl having 2 to about 8 carbon atoms (e.g. vinyl, propenyl, 2-butenyl, 3-butenyl, isobutenyl, octenyl, etc.), cycloalkyl having 5 to 7 carbon atoms (e.g. cyclopentyl, cyclohexyl, cycloheptyl, etc.), lower ($C_{1-3}$) alkyl (e.g. methyl, ethyl, n-propyl, isopropyl, etc.) which is substituted with optionally substituted aryl or cycloalkyl having 5 to 7 carbon atoms (e.g. benzyl, p-chlorobenzyl, phenethyl, cyclopentylmethyl, cyclohexylmethyl, etc.), lower ($C_{2-3}$) alkenyl (e.g. vinyl, propenyl, allyl, isopropenyl, etc.) which is substituted with optionally substituted aryl or cycloalkyl having 5 to 7 carbon atoms (e.g. cinnamyl, etc.), optionally substituted aryl (e.g. phenyl, p-tolyl, naphthyl, etc.), straight or branched lower alkoxy having 1 to 6 carbon atoms (e.g. methoxy, ethoxy, n-propoxy, isopropoxy, n-butoxy, Isobutoxy, sec-butoxy, t-butoxy, n-pentyloxy, isopentyloxy, neopentyloxy, etc.), straight or branched lower alkenyloxy having 2 to about 3 carbon atoms (e.g. allyloxy, isobutenyloxy, etc.), cycloalkyloxy having 5 to 7 carbon atoms (e.g. cyclopentyloxy, cyclohexyloxy, cycloheptyloxy, etc.), lower ($C_{1-3}$) alkoxy (e.g. methoxy, ethoxy, n-propoxy, isopropoxy, etc.) which is substituted with optionally substituted aryl or cycloalkyl having 5 to 7 carbon atoms (e.g. benzyloxy, phenethyloxy, cyclopentylmethyloxy, cyclohexylmethyloxy, etc.), lower ($C_{2-3}$) alkenyloxy (e.g. vinyloxy, propenyloxy, allyloxy, isopropenyloxy, etc.) which is substituted with optionally substituted aryl or cycloalkyl having 5 to 7 carbon atoms (e.g. cinnamyloxy, etc.), optionally substituted aryloxy (e.g. phenoxy, p-nitrophenoxy, naphthoxy, etc.)]. Examples of groups capable of forming.an anion and groups convertible thereinto for R' may include, for example, tetrazolyl groups optionally protected with optionally substituted lower alkyl such as lower ($C_{1-4}$) alkyl and lower ($C_{1-4}$) alkoxy lower ($C_{1-4}$) alkyl or acyl such as lower ($C_{2-5}$) alkanoyl and optionally substituted benzoyl, trifluoromethanesulfonic amide, phosphoric acid, sulfonic acid, and the like. Examples of substituents for R' include —COOH and salts thereof, —COOMe, —COOEt, —COOtBu, —COOPr, pivaloyloxymethoxycarbonyl, 1-(cyclohexyloxycarbonyloxy)ethoxycarbonyl, 5-methyl-2-oxo-1,3-dioxolen-4-ylmethyloxycarbonyl, acetoxymethyloxycarbonyl, propionyloxymethoxycarbonyl, n-butyryloxymethoxycarbonyl, isobutyryloxymethoxycarbonyl, 1-(ethoxycarbonyloxy) ethoxy-carbonyl, 1-(acetyloxy)ethoxycarbonyl, 1-(isobutyryloxy)ethoxycarbonyl, cyclohexylcarbonyloxymethoxycarbonyl, benzoyloxymethoxycarbonyl, cinnamyloxycarbonyl, cyclopentylcarbonyloxymethoxycarbonyl, etc. Such groups may include those which are capable of forming anions (e.g. —COO—, derivatives thereof, etc.) or convertible thereinto either chemically or under biological and/or physiological conditions (for example, in vivo reaction such as oxidation-reduction or hydrolysis catalyzed by in vivo enzymes).

The benzene ring A may optionally contain substitution in addition to the R' group and such substituents include halogen [e.g. F, Cl, Br, etc.); nitro; cyano; optionally substituted amino (e.g. amino, N-lower ($C_{1-4}$) alkyl such as methylamino and ethylamino, N,N-dilower ($C_{1-4}$) alkyl amino such as dimethylamino and diethylamino, N-arylamino such as phenylamino and naphthylamino, N-aralkylamino such as benzylamino and naphthylmethylamino, and alicyclic amino such as morpholino, piperidino, piperazino and N-phenylpiperazino]; groups having the formula: —W—$R^{13}$ wherein W is a chemical bond, —O—, —S—, or

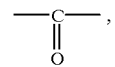

and $R^{13}$ is hydrogen or an optionally substituted lower alkyl group (e.g. lower ($C_{1-4}$) alkyl optionally substituted with hydroxyl, optionally substituted amino (e.g. amino, dimethylamino, diethylamino, piperidino, morpholino, etc.), halogen or lower ($C_{1-4}$) alkoxy, etc.); groups having the formula: —(CH$_2$)$_s$—CO—D wherein D is hydrogen, hydroxyl, optionally substituted amino (e.g. amino, N-lower ($C_{1-4}$) alkylamino, N,N-dilower ($C_{1-4}$) alkyl amino, etc.), or optionally substituted alkoxy [e.g. lower ($C_{1-6}$) alkoxy optionally substituted with hydroxyl, optionally substituted amino (e.g. amino, dimethylamino, diethylamino, piperidino, morpholino, etc.), halogen, lower ($C_{1-6}$) alkoxy, lower ($C_{1-6}$) alkylthio or optionally substituted dioxolenyl (e.g. 5-methyl-2-oxo-1,3-dioxolen-4-yl, etc.) on the alkyl moiety and groups having the formula: —OCH($R^9$)OCOR$^{10}$ wherein $R^9$ is hydrogen, straight or branched lower alkyl having 1 to 6 carbon atoms (e.g. methyl, ethyl, n-propyl, isopropyl, n-butyl, isobutyl, t-butyl, n-pentyl, isopentyl, neopentyl, etc.), or cycloalkyl having 5 to 7 carbon atoms (e.g. cyclopentyl, cyclohexyl, cycloheptyl, etc.) and $R^{10}$ is straight or branched lower alkyl having 1 to 6 carbon atoms (e.g. methyl, ethyl, n-propyl, isopropyl, n-butyl, isobutyl, sec-butyl, t-butyl, n-pentyl, isopentyl, neopentyl, etc.), straight or branched lower alkenyl having 2 to about 8 carbon atoms (e.g. vinyl, propenyl, 2-butenyl, 3-butenyl, isobutenyl, octenyl, etc.), cycloalkyl having 5 to 7 carbon atoms (e.g. cyclopentyl, cyclohexyl, cycloheptyl, etc.), lower ($C_{1-3}$) alkyl (e.g. methyl, ethyl, n-propyl, isopropyl, etc.) which is substituted with optionally substituted aryl or cycloalkyl having 5 to 7 carbon atoms (e.g. benzyl, p-chlorobenzyl, phenethyl, cyclopentylmethyl, cyclohexylmethyl, etc.), lower ($C_{2-3}$) alkenyl (e.g. vinyl, propenyl, allyl, isopropenyl, etc.) which is substituted with optionally substituted aryl or cycloalkyl having 5 to 7 carbon atoms (e.g. cinnamyl, etc.), optionally substituted aryl (e.g. phenyl, p-toluyl, naphthyl, etc.), straight or branched lower alkoxy having 1 to 6 carbon atoms (e.g. methoxy, ethoxy, n-propoxy, isopropoxy, n-butoxy, isobutoxy, sec-butoxy, t-butoxy, n-pentyloxy, isopentyloxy, neopentyloxy, etc.), straight or branched lower alkenyloxy having 2 to about 8 carbon atoms (e.g. allyloxy, isobutenyloxy, etc.), cycloalkyloxy having 5 to 7 carbon atoms (e.g. cyclopentyloxy, cyclohexyloxy, cycloheptyloxy, etc.), lower ($C_{1-3}$) alkoxy (e.g. methoxy, ethoxy, n-propoxy, isopropoxy, etc.) which is substituted with optionally substituted aryl or cycloalkyl having 5 to 7 carbon atoms (e.g. benzyloxy, phenethyloxy, cyclopentylmethyloxy, cyclohexylmethyloxy, etc.), lower ($C_{2-3}$) alkenyloxy (e.g. vinyloxy, propenyloxy, allyloxy, isopropenyloxy, etc.) which is substituted with optionally substituted aryl or cycloalkyl having 5 to 7 carbon atoms (e.g. cinnamyloxy, etc.), optionally substituted aryloxy (e.g. phenoxy, p-nitrophenoxy, naphthoxy, etc.)], and p is 0 or 1; tetrazolyl optionally protected with, for example, an optionally substituted lower alkyl group (e.g. lower ($C_{1-4}$) alkoxymethyl, optionally substituted arylmethyl, etc.) or an acyl group (e.g. lower ($C_{2-5}$) alkanoyl, optionally substituted benzoyl, etc.); trifluoromethanesulfonic amide; phosphoric acid; sulfonic acid; etc.

One or two of these substituents may be substituted at various positions of the benzene ring. When two substituents are present at the 4 and 5 or 5 and 6 positions on the ring A, they may be taken together to form a ring (e.g. benzene, etc.). Such rings may be substituted with the same groups as for the ring A.

X shows that the adjacent phenylene group is bonded to the phenyl group directly or through a spacer with an atomic chain of 2 or less. As the spacer, any one can be exemplified, so long as it is a divalent chain in which the number of atoms constituting the straight chain is 1 or 2, and it may have a side chain. Examples of such spacers include lower ($C_{1-4}$) alkylene,

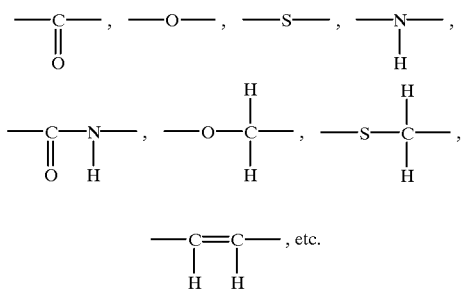

The most preferred X is a chemical bond between the phenylene group and the phenyl group.

Y represents that $R^1$ is bonded to the 2-position of benzimidazole through a hetero atom. Examples of Y include —O—, —$SO_m$— wherein m is 0, 1, or 2, —$N(R^4)$— wherein $R^4$ is hydrogen or an optionally substituted lower ($C_{1-4}$) alkyl group, and the like, preferably —O—, —S—, and —NH—, more preferably —O— and —S—, especially —O—. $R^1$ and $R^4$ may be taken together with the N atom attached thereto to form a heterocyclic ring (e.g. piperidino, morpholino, etc.).

When $R^1$=H, the compounds having the formula (I) [Compound (I)] can exist in two tautomeric forms.

When the compounds of the present invention have several asymmetric carbon atoms, they can thus exist in several stereochemical forms. The invention includes the mixture of isomers and the individual stereoisomers. It is intended that the present invention includes geometrical isomers, rotational isomers, enantiomers, racemates, and diastereomers.

The compounds of the present invention can exist in any pro-drug form of those wherein R' is carboxyl or the anion therefrom.

Among the compounds represented by the above formula (I), a preferred embodiment of the invention is a compound of the formula:

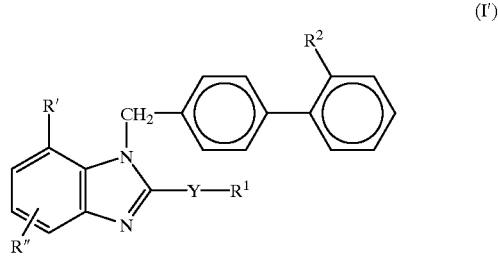

(I')

wherein $R^1$ is lower ($C_{1-5}$) alkyl optionally substituted with hydroxyl, amino, halogen, or a lower ($C_{1-4}$) alkoxy group (inter alia lower ($C_{2-3}$) alkyl); R' is —CO—D' wherein D' is hydroxyl, amino, N-lower ($C_{1-4}$) alkylamino, N,N-dilower ($C_{1-4}$) alkyl amino, or lower ($C_{1-4}$) alkoxy optionally substituted with hydroxyl, amino, halogen, lower ($C_{1-4}$) alkoxy, lower ($C_{2-6}$) alkanoyloxy (e.g. acetyloxy, pivaloyloxy, etc.) or 1-lower ($C_{1-6}$) alkoxycarbonyloxy (e.g. methoxycarbonyloxy, ethoxycarbonyloxy, cyclohexyloxycarbonyloxy, etc.) on the alkyl moiety, or tetrazolyl optionally protected with an optionally substituted lower ($C_{1-4}$) alkyl or acyl group (e.g. lower ($C_{2-5}$) alkanoyl, benzoyl, etc.); $R^2$ is tetrazolyl optionally protected with an optionally substituted lower ($C_{1-4}$) alkyl (e.g. methyl, triphenylmethyl (trityl), methoxymethyl, ethoxymethyl, p-methoxybenzyl, p-nitrobenzyl, etc.) or acyl group (e.g. lower ($C_{2-5}$) alkanoyl, benzoyl, etc.), or carboxyl optionally protected with an optionally substituted lower ($C_{1-4}$) alkyl group (e.g. methyl, triphenylmethyl (trityl), methoxymethyl, ethoxymethyl, p-methoxybenzyl, p-nitrobenzyl, etc.); R" is hydrogen, halogen, lower ($C_{1-4}$) alkyl, lower ($C_{1-4}$) alkoxy, nitro or —CO—D" wherein D" is hydroxyl or lower ($C_{1-2}$) alkoxy optionally substituted with hydroxyl, lower ($C_{1-4}$) alkoxy, lower ($C_{2-6}$) alkanoyloxy (e.g. acetyloxy, pivaloyloxy, etc.) or 1-lower ($C_{1-6}$) alkoxycarbonyloxy (e.g. methoxycarbonyloxy, ethoxycarbonyloxy, cyclohexyloxycarbonyloxy, etc.) on the alkyl moiety, or amino optionally substituted with lower ($C_{1-4}$) alkyl (inter alia hydrogen, lower ($C_{1-4}$) alkyl, or halogen, more preferably hydrogen); and Y is —O—, —S—, or —$N(R^4)$— wherein $R^4$ is hydrogen or an lower ($C_{1-4}$) alkyl group; and the pharmaceutically acceptable salts thereof.

The compounds (I) of the present invention may be prepared by several reaction schemes, as illustrated below for a preferred compound.

Scheme A

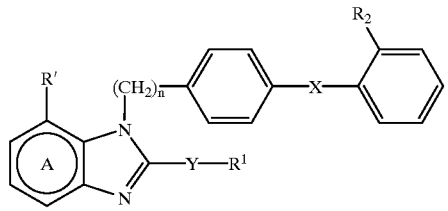

wherein $R^1$, $R^2$, R', A, X, Y and n have the above-defined meanings and Z is halogen.

Scheme B
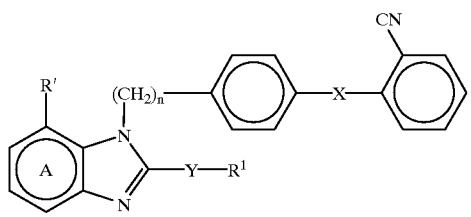
Ia
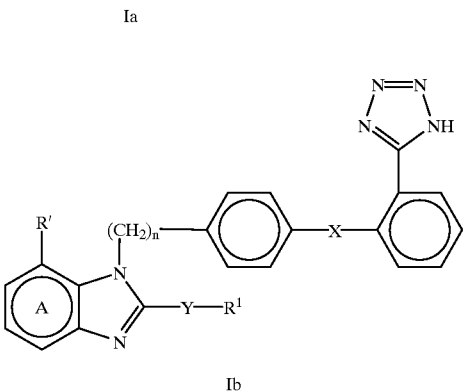
Ib
wherein each group has the above-defined meaning.
Scheme C
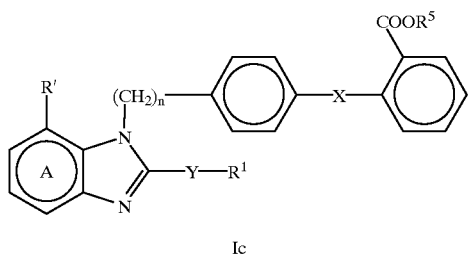
Ic
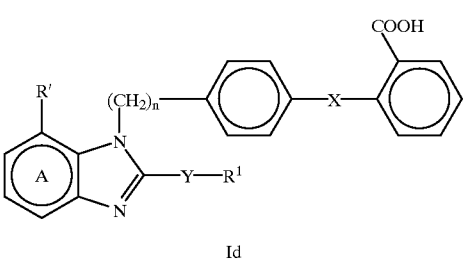
Id
wherein $R^1$, R', A, X, Y and n have the above-defined meanings, and $R^5$ is optionally substituted lower ($C_{1-5}$) alkyl.
Scheme D
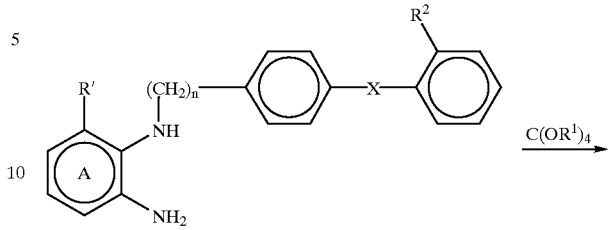
IV
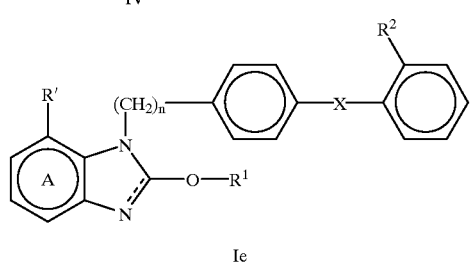
Ie
wherein each group has the above-defined meaning.
Scheme E
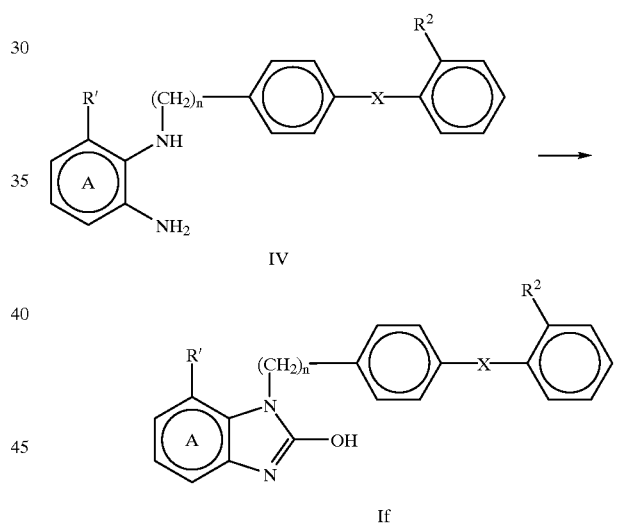
IV
If
wherein each group has the above-defined meaning.
Scheme F
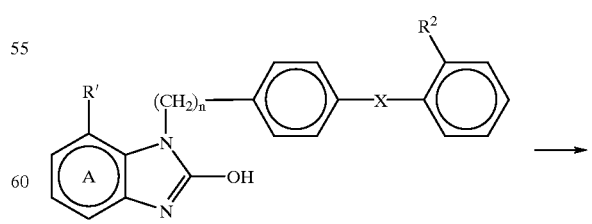
If -continued
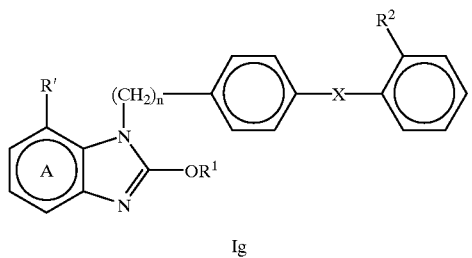
Ig
wherein each group has the above-defined meaning.
Scheme G
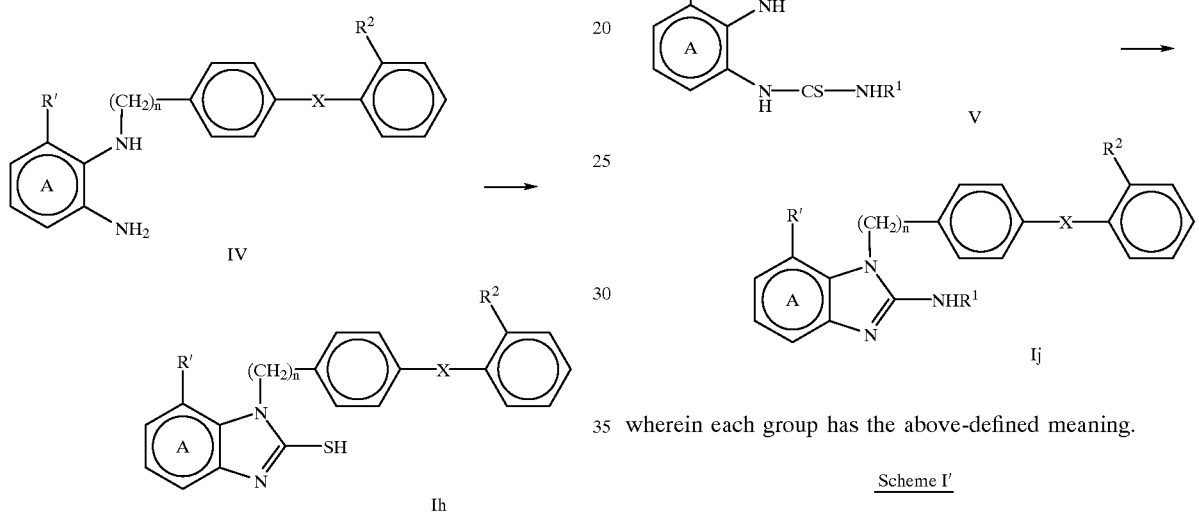
wherein each group has the above-defined meaning.
Scheme H
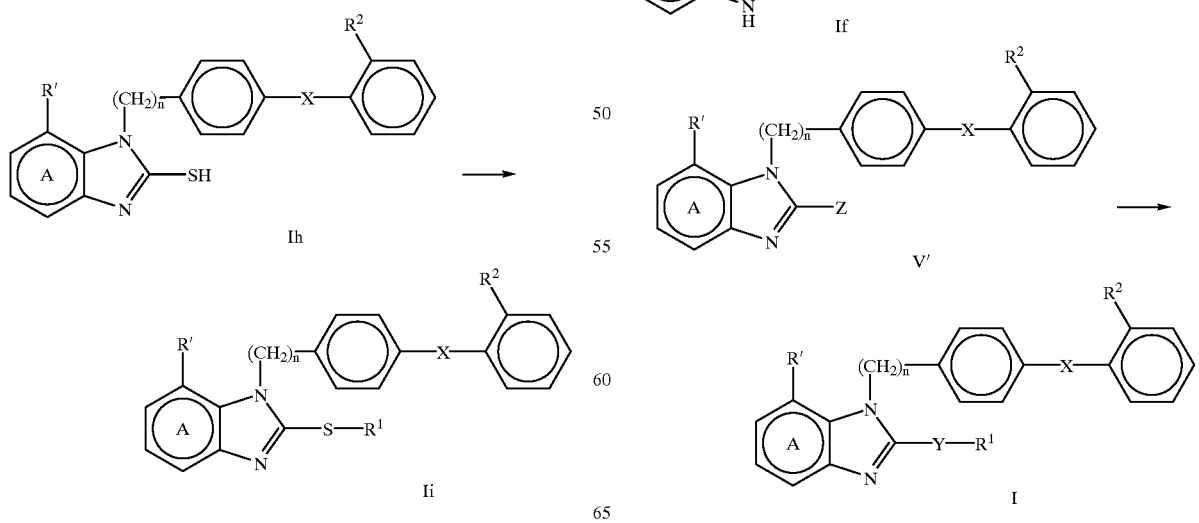
wherein each group has the above-defined meaning.
Scheme I
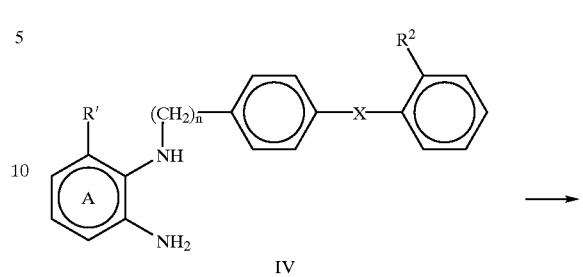
wherein each group has the above-defined meaning.
Scheme I' wherein each group has the above-defined meaning.
Scheme I″
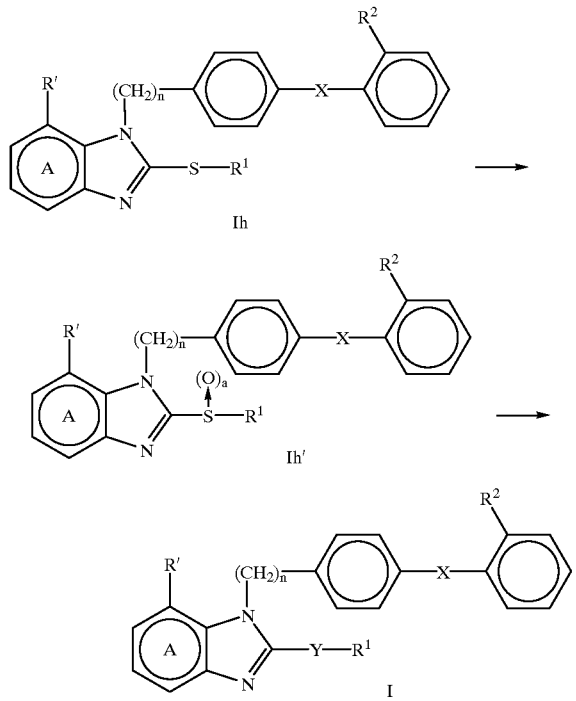
wherein each group has the above-defined meaning.
Scheme J
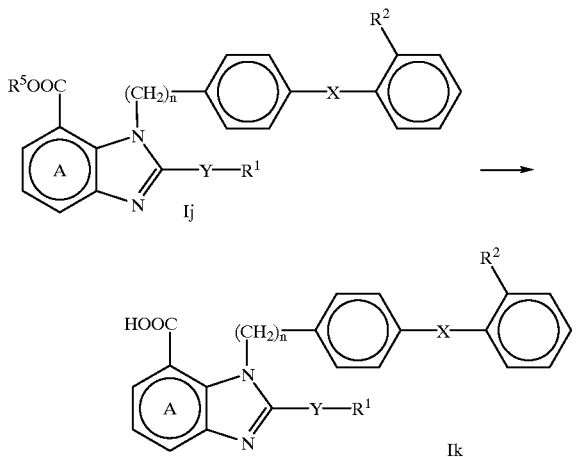
wherein each group has the above-defined meaning.
Scheme K
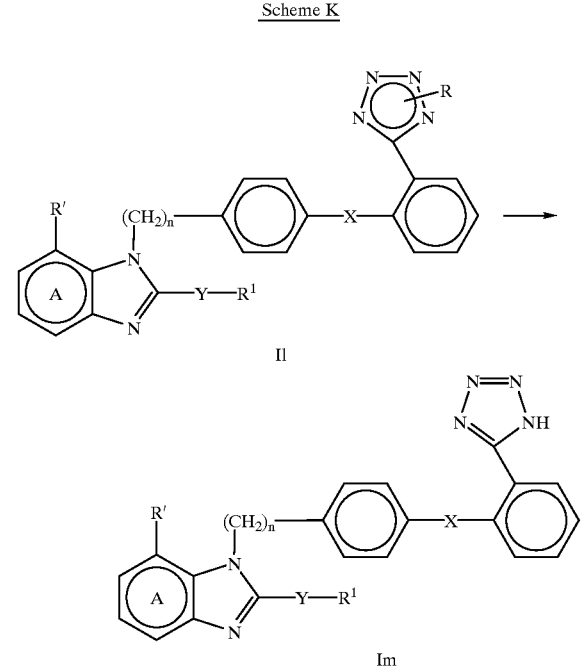
wherein each group has the above-defined meaning.
Scheme L
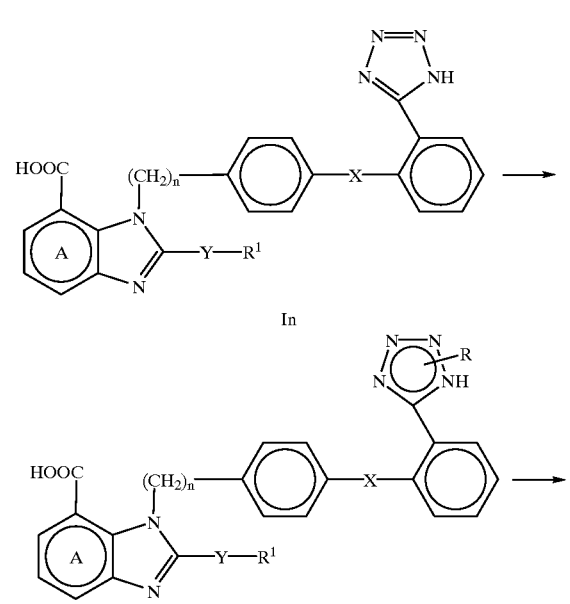

-continued

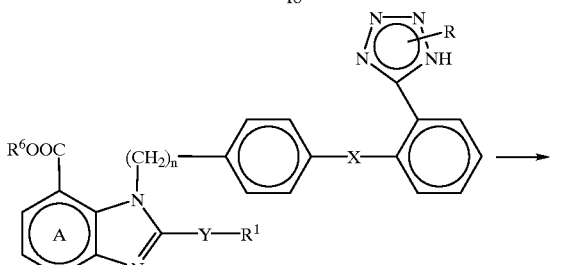

Io

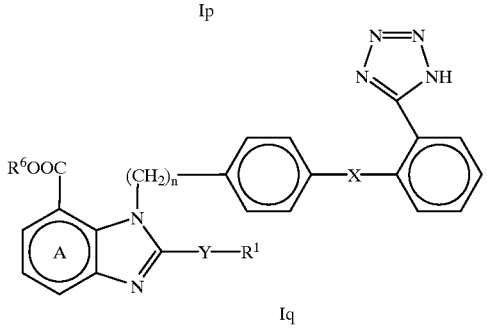

Iq wherein A, R, $R^1$, X, Y and n have the above-defined meanings, and $R^6$ is lower ($C_{1-6}$) alkyl optionally substituted with lower ($C_{2-6}$) alkanoyloxy, 1-lower ($C_{1-6}$) alkoxycarbonyloxy or the like as defined for R'.

The reaction as illustrated in Scheme A is an alkylation using an alkylating agent in the presence of a base. One molar portion of the compound (II) is employed with approximately 1 to 3 moles of the base and 1–3 moles of the alkylating agent. The reaction is conventionally conducted in solvents such as dimethylformamide, dimethylacetamide, dimethylsulfoxide, acetonitrile, tetrahydrofuran, acetone, ethylmethylketone, and the like. Examples of such bases include sodium hydride, potassium t-butoxide, potassium carbonate, sodium carbonate, and the like. Examples of such alkylating agents include substituted halides (e.g. chlorides, bromides, iodides, and the like), substituted sulfonate esters (e.g. p-toluenesulfonate esters, and the like), etc. The reaction conditions may vary depending on the combination of the base and the alkylating agent. Advantageously, the reaction is carried out at ice-cooling to room temperature for about 1–10 hours.

In the said alkylation, a mixture of two isomers, (I) and (I''') is usually obtained depending on the position of the N atom to be alkylated. While the production ratio of Compound (I) and Compound ('") varies with the reaction conditions employed and the substituents on the benzimidazole ring, these two compounds can be obtained easily as pure products respectively by conventional isolation and/or purification methods (e.g. recrystallization, column chromatography and the like).

The nitrile compound (Ia) is reacted with various azides to form the tetrazole compound (Ib) as illustrated in Scheme B. One molar portion of the compound (Ia) is employed with 1–5 moles of the azide. The reaction is conventionally conducted in solvents such as dimethylformamide, dimethylacetamide, toluene, benzene, and the like. Examples of such azides include trialkyltin azide (e.g. trimethyltin azide, tributyltin azide, triphenyltin azide, etc.), hydrogen azide and ammonium salts thereof, and the like. In the case where the organotin azide compound is employed, 1–4 moles of the azide are employed per compound (Ia) and the reaction is carried out in toluene or benzene by heating under reflux for a period of 1–4 days. When the hydrogen azide or its ammonium salt is used, 1–5 moles of sodium azide and ammonium chloride or tertiary amine (e.g. triethylamine, tributylamine, etc.) are employed per compound (Ia) and the reaction is conducted in dimethylformamide at about 100° C.–120° C. for about 1–4 days. During this reaction, it is preferable to facilitate the reaction by adding an appropriate amount of sodium azide and ammonium chloride. In this case, improvement may sometimes be observed in reaction time and yield by the addition of the azide compound in suitable fractions.

The ester (Ic) is hydrolyzed in the presence of alkali to give the carboxylic acid (Id) as illustrated in Scheme C. This reaction is conducted usually in a solvent such as aqueous alcohol (e.g. methanol, ethanol, methyl cellosolve, etc.) by using alkali in an amount of about 1 to 3 mol. relative to 1 mol. of Compound (Ic). Examples of such alkalis include sodium hydroxide, potassium hydroxide, etc. The reaction is conducted at temperatures ranging from room temperature to about 100° C. for about 1 to 10 hours, preferably around the boiling point of the solvent for about 2 to 5 hours.

The 2-alkoxy derivative (Ie) is obtained by reacting phenylenediamine (IV) with alkyl orthocarbonate as illustrated in Scheme D. The reaction is conducted in the presence of an acid by using alkyl orthocarbonate of about 1 to 3 mol. relative to Compound (IV). Examples of such alkyl orthocarbonates include orthocarbonats of, for example, methyl, ethyl, propyl, isopropyl, butyl, etc. And, by using ,for example, acetic acid or p-toluenesulfonic acid, the reaction is accelerated to afford a ring-closed compound in a good yield. As the reaction solvent, halogenated hydrocarbons and ethers can be employed but, usually, it is more convenient to conduct the reaction without a solvent. The reaction is usually conducted at about 70 to 100° C. for about 1 to 5 hours. In this reaction, a dialkoxyimino compound is produced as the reaction intermediate, which is then ring-closed into the 2-alkoxy compound (Ie) in the presence of the acid in the reaction system. It is also possible to isolate the reaction intermediate, which is then subjected to ring-closure reaction in the presence of an acid to form the 2-alkoxy compound (Ie).

The phenylenediamino compound (IV) is reacted with various reagents to give the 2-keto compound (or the 2-hydroxy compound, If) as illustrated in Scheme E. This reaction is conducted by using a carbonylating reagent (e.g. urea, diethyl carbonate, bis(1-imidazolyl)ketone, etc.) in an amount of about 1 to 5 mol. relative to 1 mol. of Compound (IV) and, usually, by using, among others, halogenated hydrocarbons (e.g. methylene chloride, chloroform, etc.), alcohols (e.g. methanol, ethanol, etc.) or amides (e.g. dimethylformamide, dimethylacetamide, etc.).

The 2-hydroxy compound (If) is selectively O-alkylated wilth a Meerwein reagent to give the 2-alkoxy compound (Ig) as illustrated in Scheme F. This reaction is conducted by using the Meerwein reagent in an amount of about 1 to 3 mol. relative to Compound (If), usually, employing, as the solvent, halogenated hydrocarbons (e.g. methylene chloride, chloroform, etc.) or ethers (e.g. methyl ether, ethyl ether, etc.). Examples of such Meerwein reagents include, among others, t-rimethyl oxonium fluoroborate ($Me_3O^+BF_4^-$), tri-ethyl oxonium fluoroborate ($Et_3O^+BF_4^-$), etc. These are preferably used by in situ preparation according to the method described in literature references [H. Meerwein, Org. Syn. 46. 113 and 120(1966)]. The reaction is preferably conducted at temperatures ranging from about room temperatures to the boiling point of the solvent used for about 2 to 20 hours.

The phenylene diamino compound (IV) is reacted with various reagents in an organic solvert to give the 2-mercapto compound (Ih) as illustrated in Scheme G. Relative to 1 mol. of the phenylene diamino compound (IV), about 1 to 3 mol. of a thiocarbonylating agent (e.g. carbon disulfide, thiourea, potassium xanthate, etc.) or isothiocyanate (e.g. methyl isothiocyanate, ethyl isothiocyanate, etc.) is used. As the reaction solvent, alcohols (e.g. methanol, ethanol, etc.), amides (e.g. dimetylformamide, dimethylacetamide, etc.) or the like can be used. The reaction is preferably conducted at temperatures ranging from room temperatures to the boiling point of the solvent used for about 5 to 20 hours.

The 2-mercapto compound (Ih) is alkylated in the presence of a base in an organic solvent to give the alkylthio compound (Ii) as illustrated in Scheme H. The reaction is conducted by using, relative to 1 mol. of Compound (Ih), about 1 to 3 mol. of the base and about 1 to 3 mol. of the alkylating agent usually in a solvent such as dimethylformamide, dimethylacetamide, dimethylsulfoxide, acetonitrile, acetone, ethyl methyl ketone, ethanol, methanol and water. As the base, there is used sodium hydroxide, potassium carbonate, sodium carbonate, sodium hydride, potassium t-butoxide, potassium hydroxide or the like. As the alkylating agent, there is used, for example, a halide (e.g. methyl iodide, ethyl iodide, propyl iodide, butyl iodide, and bromide or chloride thereof). The reaction is conducted usually at temperatures ranging from ice-cooling to the boiling point of the solvent used, while the reaction conditions vary with the base, the alkylating agent and the solvent employed.

The phenylenediamine (IV) is reacted with isothiocyanate to form the thiourea compound (V), which is then subjected to desulfurization-cyclization to give the 2-substituted amino compound (Ij) as illustrated in Scheme I. The reaction is conducted by using about 1 to 3 mol. of isothiocyanate relative to 1 mol. of Compound (IV) usually in halogenated hydrocarbons (e.g. chloroform, methylene chloride, etc.), ethers (e.g. tetrahydrofuran, dioxane, etc.), aromatic hydrocarbons (e.g. benzene, toluene, etc.), alcohols (e.g. methanol, ethanol, etc.), acetonitrile, dimethylformamide or the like. The reaction can also be conducted without these solvents. Examples of such isothiocyanates include isothiocyanates of methyl, ethyl, propyl, isopropyl, butyl, etc. The reaction is conducted preferably at temperatures ranging from room temperatures to about 50° C. for about 10 to 60 hours. The desulfurization-cyclization can be conducted in a manner as described below.

The reaction is conducted, in halogenated hdyrocarbons (e.g. HgCl$_2$), by using about 1 to 3 mol. of a metal halide (e.g. HgCl$_2$) relative to 1 mol. of the thiourea (V) obtained by the above-mentioned method. The reaction is conducted preferably at temperatures ranging from room temperature to the boiling point of a solvent employed for about 3 to 10 hours. The reaction can also be conducted by using about 1 to 3 mol. of methyl iodide relative to 1 mol. of thiourea (V) in alcohols (e.g. methanol or ethanol), preferably at temperatures ranging from room temperature to about the boiling point of the solvent for about 3 to 15 hours.

The 2-halogeno compound (V') readily prepared from the compound (If) is reacted with various nucleophilic reagents to form the compound (I) as illustrated in Scheme I'. The reaction can be carried out according to the procedures as described in known references (e.g. D. Harrison and J. J. Ralph, J. Chem. Soc., 1965, 236). The compound (If) is reacted with a halogenating reagent (e.g. phosphorus oxychloride, phosphorus trichloride, etc.) to form the 2-halogeno compound (V') which is reacted with various nucleophilic reagents (e.g. alcohols, mercaptans, amines, etc.) in a suitable organic solvent to give the compound (I). The reaction conditions may vary depending on the nucleophilic reagent employed. Upon the reaction with alcohols, alcoholates (e.g. sodium methoxide, sodium ethoxide, sodium propoxide, etc.) derived from alcohols and sodium metal are preferably used. As the reaction solvent, alcohols then used for nucleophilic reagents can be employed. Relative to 1 mol. of the compound (V'), there is used about 2 to 5 mol. of an alcoholate. Advantageously, the reaction is usually conducted at approximately the boiling point of the solvent used for about 1 to 3 hours. Upon the reaction with amines, about 3 to 10 mol. of an amine is used relative to 1 mol. of the compound (V'). As the reaction solvent, alcohols (e.g. ethanol, etc.) are employed but, an excess amount of amines can be used. Advantageously, the reaction is usually conducted at temperatures ranging from about the boiling point of the solvent to 150° C. for about 1 to 10 hours. Upon the reaction with mercaptans, about 2 to 5 mol. of a mercaptan is used relative to 1 mol. of the compound (V'). The reaction is preferably conducted in the presence of about 1 to 3 mol. of an base (e.g. sodium carbonate, potassium carbonate, etc.) relative to Compound (IV). Examples of solvents include acetonitrile, alcohols, halogenated hydrocarbons (e.g. chloroform, dichloroethane, etc.), ethers (e.g. tetrahydrofuran, dioxane, etc.) or amides (e.g. dimethylformamide, dimethylacetamide, etc.). The reaction can be conducted preferably at temperatures ranging from 50° C. to about the boiling point of the solvent for about 1 to 5 hours.

The compound (Ih) is reacted with an oxidizing reagent (e.g. m-chloroperbenzoic acid, etc.) to form the sulfoxide or sulfone compound (Ih') which is reacted with various nucleophilic reagents (e.g. alcohols, amines, mercaptans, etc.) to give the compound (I) as illustrated in Scheme I". The oxidation of the compound (Ih) to the sulfoxide or sulfone compound (Ih') is preferably conducted in solvents including halogenated hydrocarbons (e.g. dichloromethane, chloroform, dichloroethane, etc.), ethers (e.g. tetrahydrofuran, dioxane, etc.) and the like. Examples of such oxidizing reagents include organic peracids such as m-chloroperbenzoic acid, N-halosuccinimides such as N-bromosuccinimide, etc. Generally, the oxidizing reagent is employed in an equal or slightly excess amount when compared to the compound (Ih). The sulfoxide can be produced by one mole of the oxidizing reagent and the sulfone compound (Ih') by two moles. The reaction is preferably conducted at temperatures ranging from about ice-cooled temperature to room temperature for about 3 to 10 hours.

The reaction of the compound (Ih') into the compound (I) is conducted in essentially the same manner as mentioned in Scheme I'.

The carboxylic acid (Ik) is formed by the alkaline hydrolysis of the carboxylic acid ester compound (Ij) as illustrated in Scheme J. The reaction is conducted by using about 1 to 3 mol. of alkali relative to 1 mol. of Compound (Ij) usually in a solvent such as an aqueous alcohol (e.g. methanol, ethanol, methyl cellosolve, etc.). Examples of such alkalis include sodium hydroxide, potassium hydroxide or the like. The reaction is conducted at temperatures ranging from room temperature to about 100° C. for about 1 to 10 hours, preferably at about the boiling point of a solvent used for about 3 to 5 hours.

The protected tetrazole derivative (II) is deprotected to give Compound (Im) as depicted in Scheme K. Conditions of the deprotection depend on the protective group (R) then used. When R is triphenylmethyl, 2-tetrahydropyranyl, methoxymethyl, ethoxy methyl or the like, it is convenient to conduct the reaction in an aqueous alcohol (e.g. methanol, ethanol, etc.) containing about 0.5 N to 2 N hydrochloric acid or acetic acid at about room temperatures for about 1 to 10 hours.

The compound (Iq) is prepared by protecting the tetrazole group in the presence of a base, and then the carboxyl group to give the ester compound (Ip), followed by removing the protective group under acid conditions as illustrated in Scheme L. In the reaction to obtain Compound (Io) from Compound (In), an alkylating agent is useid in an amount of about 1 to 1.5 mol. relative to 1 mol. of Compound (In). Examples of the solvents to be used for the reaction include halogenated hydrocarbons such as chloroform, methylene chloride ancd ethylene chloride, ethers such as dioxane and tetrahydrofuran, acetonitrile, pyridine, etc. Examples of such bases include potassium carbonate, sodium carbonate, triethylamine, pyridine, etc. Examples of such alkylating agents include halides such as triphenylmethyl chloride and methoxy methyl chloride, etc. While reaction conditions vary with combinations of the base and the alkylating agent employed, it is preferable to conduct the reaction by using triphenylmethyl chloride at temperatures ranging from ice-cooling to room temperature for about 1 to 3 hours in methylene chloride in the presence of triethylamine. In the reaction for producing Compound (Ip) from Compound (Io) thus obtained, the alkylating agent is used in an amount of about 1 to 3 mol. relative to 1 mol. of Compound (Iq). Examples of the reaction solvent include amides such as dimethylformamide and dimethylacetamide, acetonitrile, dimethylsulfoxide, acetone, ethyl methyl ketone, etc. Examples of the bases include potassium carbonate, sodium carbonate, sodium hydride, potassium t-butoxide, etc. Examples of such alkylating agents include halides such as cyclohexyl 1-iodoethyl carbonate, ethyl 1-iodoethyl carbonate, pivaloyloxymethyl iodide, etc. While reaction conditions vary with combinations of the base and the alkylating agent employed, it is preferable to subject Compound (Io) to reaction in DMF, by adding the alkylating agent in the presence of potassium carbonate, at about room temperatures for about 30 minutes to one hour.

The reaction for deprotecting Compound (Ip) thus obtained is conducted preferably in a manner similar to the reaction (K). When trityl group is used as the protecting group of tetrazole group, it is preferable to conduct the reaction in methanol or ethanol, while adding 1N—HCl, at about room temperatures for about 30 minutes to one hour.

The reaction products obtained as above by the reaction processes (A) to (L), can be easily isolated and/or purified by or according to conventional methods such as, for example, evaporation of solvents, extraction by water or organic solvents, concentration, neutralization, recrystallization, distillation, column chromatography and the like. The compounds (I) thus produced via the reaction processes as depicted in Schemes A to L can be isolated and/or purified from the reaction mixture according to conventional methods such as, for example, recrystallization and column chromatography, to obtain a crystalline product.

The compounds obtained as above by the reaction processes (A) to (L), may be in the form of solvates or salts (including addition salts) derived from pharmaceutically or physiologically acceptable acids or bases. These salts include but are not limited to the following: salts with inorganic acids such as hydrochloric acid, hydrobromic acid, hydroiodic acid, sulphuric acid, nitric acid, phosphoric acid and, as the case may be, such organic acids as acetic acid, oxalic acid, succinic acid, citric acid, ascorbic acid, lact:Lc acid, p-toluenesulfonic acid, methanesulfonic acid, fumaric acid, tartaric acid and maleic acid. Other salts include salts with ammonium, alkali metals or alkaline earth metals, such as sodium, potassium, calcium or magnesium or with organic bases (e.g. trialkylaminles, dibenzylamine, ethanolamine, triethanolamine, N-methylmorpholine, etc).

And, by conventional means, the compounds (I) can be formed as salts with non-toxic, physiologically or pharmaceutically acceptable acids or bases, for example salts with an inorganic acid such as hydrochloride, sulfate or nitrate, and, depending on compounds, salts with an organic acid such as acetate, oxalate, succinate or maleate, salts with an alkali metal such as sodium salt or potassium salt, or salts with an alkaline earth metal such as calcium salt.

For the synthesis of these compounds (I), the starting compounds (II) and (IV) can be synthesized by or according to the methods described in, for example, the following literature references or methods analogous thereto, namely, by the reactions (M), (N), (O) and (P) as depicted below.

(1) P. N. Preston, The Chemistry of Heterocyclic Compounds, Vol. 40, ed. by P. N. Preston, John Wiley & Sons Inc., New York (1981), pp. 1–286, (2) E. S. Schipper and A. R. Day, Heterocyclic Compounds, Vol. 5, ed. by R. C. Elderfield, John Wiley & Sons Inc., New York (1965), pp. 194–297, (3) N. J. Leonard, D. Y. Curtin, & K. M. Beck, J. Am. Chem. Soc. 69, 2459 (1947), (4) S. Weiss, H. Michaud, H. Prietzel, & H. Kromer, Angew. Chem. 85, 866 (1973), (5) W. B. Wright, J. Heterocycl. Chem., 2, 41 (1965), (6) A. M. E. Omar, Synthesis, 1974, 41, (7) D. J. Brown & R. K. Lynn, J. Chem. Soc.(Perkin I), 1974, 349, (8) J. A. Van Allan & B. D. Deacon, Org. Syn., 30, 56 (1950), (9) S. P. Singh, S. S. Parmar & B. R. Pandey, J. Heterocycl. Chem., 14, 1093 (1977),

(10) S. Nakajima, I. Tanaka, T. Seki & T. Anmo, Yakugaku Zasshi, 78, 1378 (1959),

(11) K. Seno, S. Hagishita, T. Sato & K. Kuriyama, J. Chem. Soc., Perkin Trans. 1984, 2013,

(12) D. R. Buckle et al., J. Med. Chem., 30, 2216 (1987),

(13) R. P. Gupta, C. A. Larroquette & K. C. Agrawal, J. Med. Chem., 25, 1342 (1982), etc.

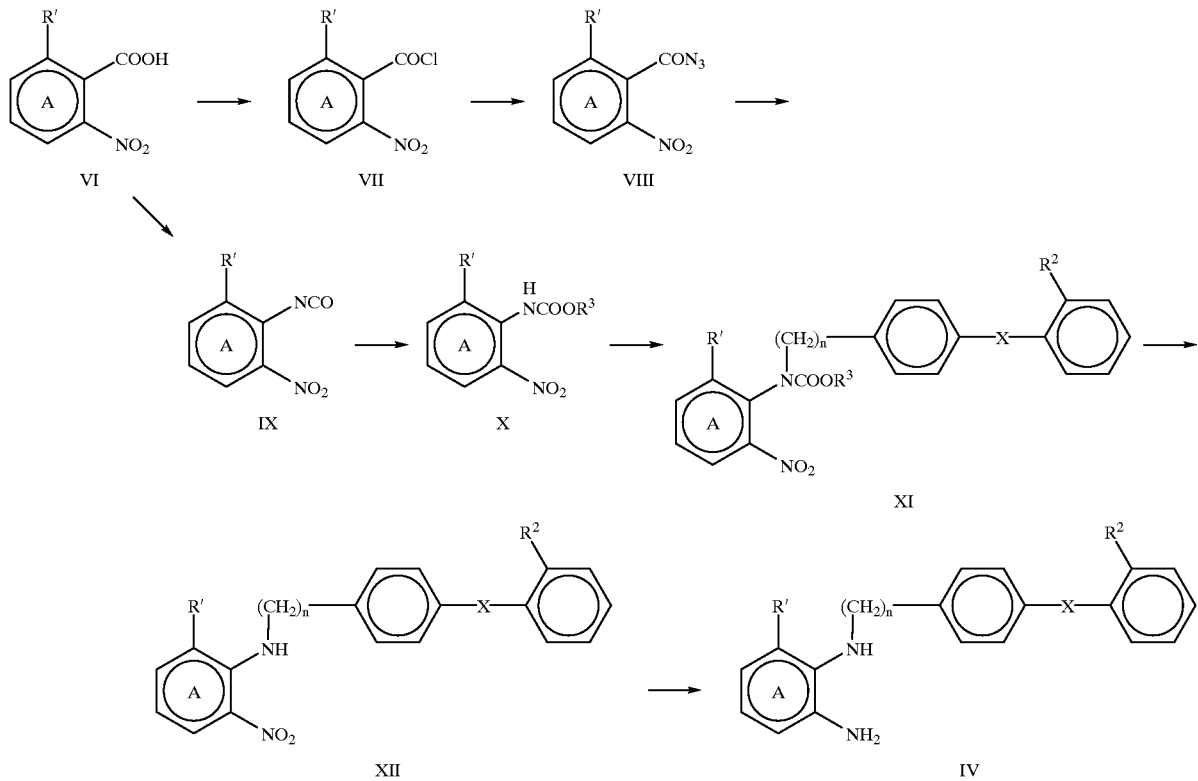
[wherein $R^2$, R', A, X and n are of the same meaning as defined above; and $R^3$ stands for a lower ($C_{1-4}$) alkyl group].
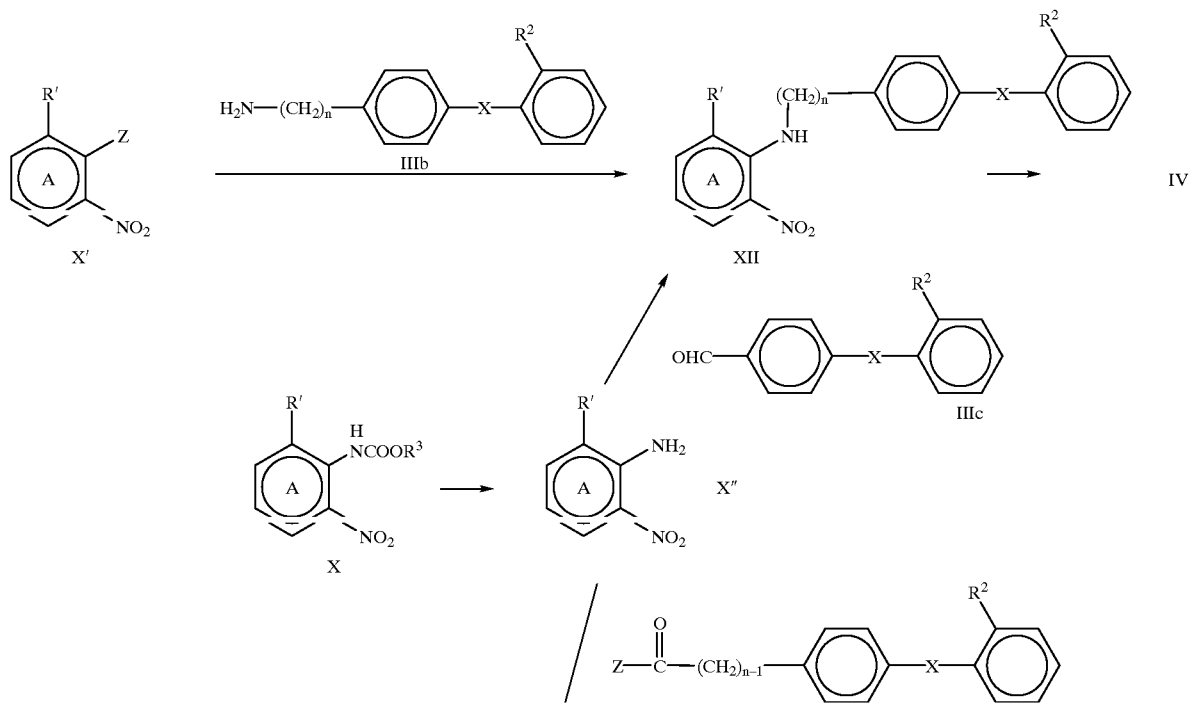

-continued

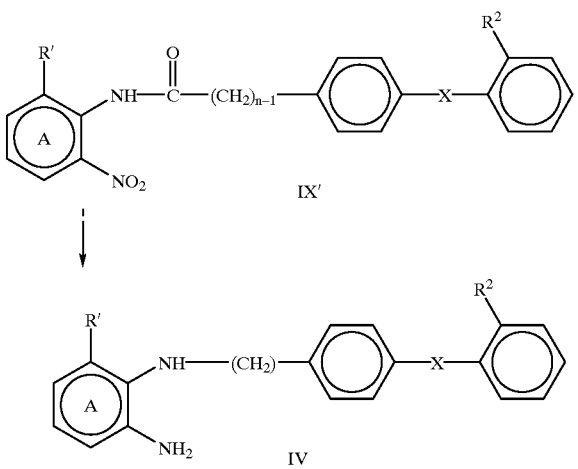

wherein $R^2$, $R^3$, R', A, Z, X and n are of the same meaning as defined above.

Schemes M and M' illustrate the process for preparing important intermediates which are useful in synthesizing the compound (I) of the present invention.

These compounds can be produced according to the above-mentioned references. The compound (VI) is converted by the Curtius reaction into the carbamic acid compound (X) followed by alkylation and subsequent reduction of nitro to form the diamino compound (IV). In the rearrangement of Compound (VI) to Compound (X), Compound (X) is produced in a high yield according to conventional procedures of the Curtius rearrangement: the acid chloride (VII)→the acid azide (VIII)→the isocyanate (IX) →Compound (X). The compound (VI) is conveniently heated with diphenylphosphoryl azide (DPPA) in the presence of triethylamine in DMF to form the isocyanate (IX) via the acid azide (VIII) followed by reaction of an alcohol to give the compound (X) in a high yield. The compound (X) thus obtained is alkylated in the same manner as in Scheme A to form the compound (XI). In the reaction, it is convenient to heat the reaction mixture under reflux for about 4–6 hours in the presence of potassium carbonate as a base in acetonitrile. The compound (XI) is heated under reflux in an alcohol containing a mineral acid (e.g. hydrochloric acid, sulphuric acid, etc.) or an organic acid (e.g. trifluoroacetic acid, etc.), for about 1–2 hours to give the compound (XII). Various reducing reagents (e.g. raney nickel, stannic chloride, etc.) can be employed in the reduction of the nitro compound (XII) to the diamino compound (IV). Among them, the combination of ferric chloride and hydrazine·hydrate in an alcohol is the most convenient. Further, the compound (IV) can be prepared by various techniques other than those mentioned above.

The compound (X') commercially available or readily obtained by known methods in the art is preferably reacted with the amine (IIIb) in the presence of a base (e.g. potassium carbonate, sodium carbonate, amines, etc.) in an organic solvent (e.g. alcohol, ethers, halogenated hydrocarbons, amides, etc.) at temperatures ranging from about the boiling point of the solvent to 100° C. for about 5 to 20 hours.

The compound (X") readily obtained by acid treatment of the compound (X) is subjected to condensation under dehydration conditions including azeotropic removal of water (or in the presence of a dehydrating agents) in an organic solvent (e.g. ethers, halogenated hydrocarbons, aromatic hydrocarbons, etc.) followed by reaction with a reducing reagent (e.g. $NaCNBH_3$, etc.) to form the compound (XII). The condensation under dehydration conditions can be accelerated byr using conventional acid or base catalysts.

The compound (X") is reacted with the acid chloride (IIId), preferably in the presence of a base (e.g. pyridine, triethylamine,, dimethylaminopyridine, etc.) in an organic solvent (e.g. halogenated hydrocarbons, pyridine, etc.) at temperatures ranging from room temperature to about the boiling point of the solvent for about 2 to 20 hours, to the amide (XI'). The resulting amide (XI') is reacted with a reducing reagent (e.g. sodium aluminum hydride, sodium bis(2-methoxyethoxy aluminum hydride, etc.) to form the diamino (IV).

Scheme N

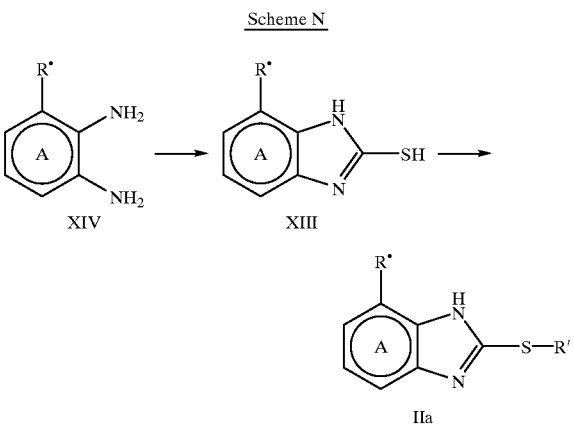

[wherein each group is of the same meaning as defined above].

Scheme O

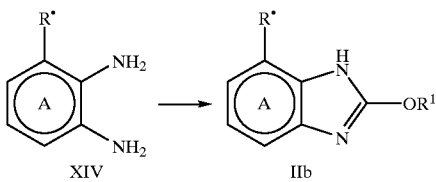

[wherein each group is of the same meaning as defined above].

Scheme P

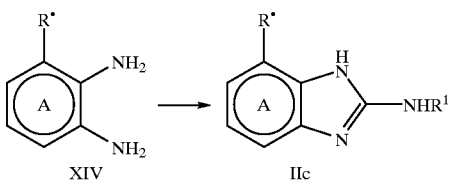

[wherein each group is of the same meaning as defined above].

And, among the starting compounds (ITT), the compound (III) wherein n denotes 1, i.e. the compound (IIIa) is commercially available, or can be readily obtained also by subjecting Compound (XV) to halogenomethylation in accordance with the methods described in literature references, for example;

1) J. R. E. Hoover, A. W. Chow, R. J. Stedman, N. M. Hall, H. S. Greenberg, M. M. Dolan and R. J. Feriauto, J. Med. Chem., 7, 245 (1964),
2) R. J. Stedman, J. R. E. Hoover, A. W. Chow, M. M. Dolan, N. M. Hall and R. J. Feriauto, J. Med. Chem., 7; 251 (1964),
3) H. Gilman and R. D. Gorsich, J. Am. Chem. Soc., 78, 2217 (1956),
4) M. Orchin and E. Oscar Woolfolk, J. Am. Chem. Soc., 67, 122 (1945), etc.

Scheme Q

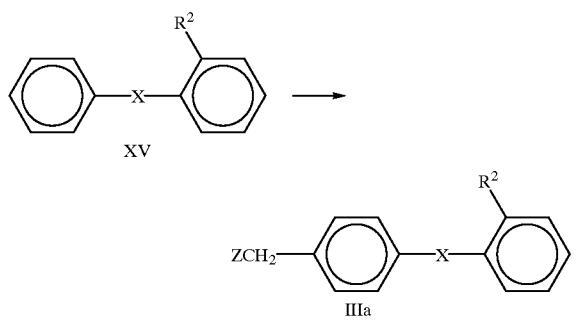

[wherein each group is of the same meaning as defined above].

The compound (IIIa') can also be readily prepared according to the methods described in L. N. Pridgen, L. Snyoler and J. Prol, Jr., J. Org. Chem., 54, 1523 (1989) as illustrated in Scheme R, followed by halogenation ($R^{12}$=Me) or halogenomethylation ($R^{12}$=H).

Scheme R

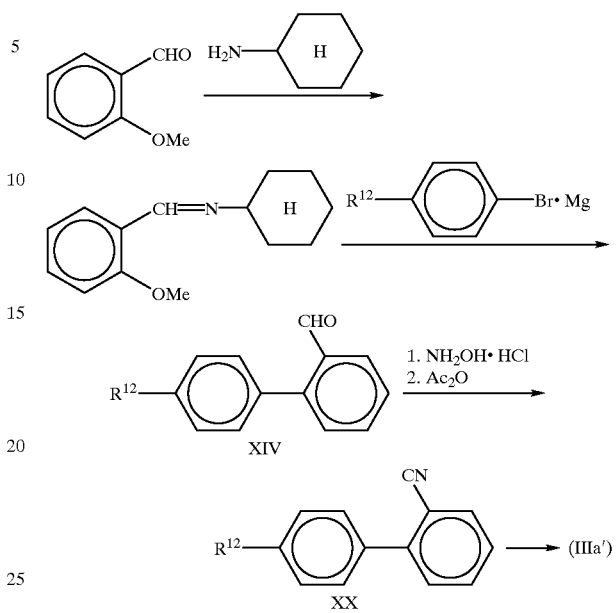

[wherein $R^{12}$ is hydrogen or methyl].

Further, among the starting compounds (III), the compound (III) wherein n denotes 2, i.e. the compound (IIIb) can be obtained from the compound (IIIa) in accordance with the reaction (S).

Scheme S

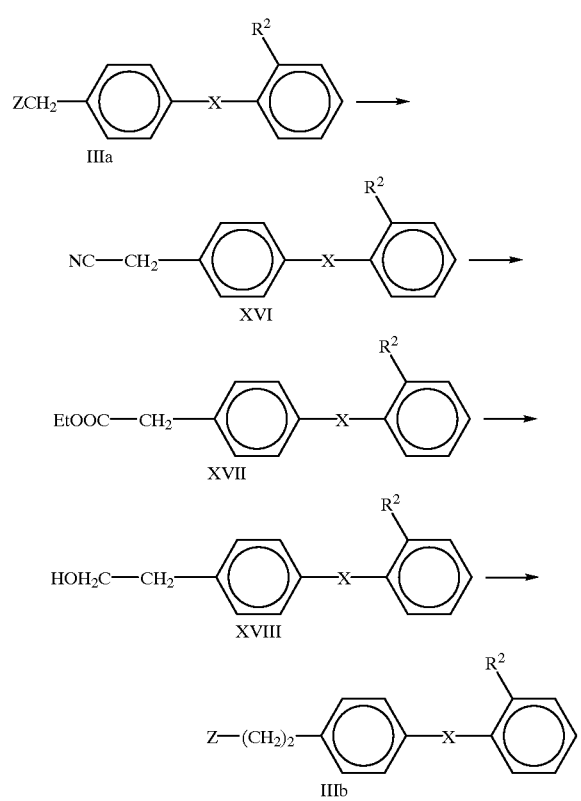

[wherein each group is of the same meaning as defined above].

The compounds and the salts thereof thus produced are less toxic, strongly inhibit the vasoconstrictive and hypertensive actions of angiotensin II, exert a hypotensive effect in animals, in particular mammals (e.g. human, dog, rabbit, rat, etc.), and therefore they are useful as therapeutics for not only hypertension but also circulatory diseases such as heart failure (hypertrophy of the heart, cardiac insufficiency, cardiac infarction or the like), strokes, cerebral apoplexy, nephropathy and nephritis. The compounds (I) and salts thereof according to the present invention strongly inhibit vasoconstriction and hypertension derived by angiotensin II and therefore possess potent anti-hypertensive activity in animals, more specifically mammal animals (e.g. humans, dogs, pigs, rabbits, rats, etc.). Further, the compounds (I) and salts thereof according to the present invention are of quite low toxicity and clinically useful in treating not only hypertension but also circulatory system diseases such as heart and brain diseases, strokes, renal failures, nephritiLE and the like.

For therapeutic use, the compounds (I) and salts thereof can be orally, parenterally, by inhalation spray, rectally, or topically administered as pharmaceutical compositions or formulations (e.g. powders, granules, tablets, pills, capsules, injections, syrups, emulsions, elixirs, suspensions, solutions and the like) comprising at least one such compound alone or in admixture with pharmaceutically acceptable carriers, adjuvants, vehicles, excipients and/or diluents. The pharmaceutical compositions can be formulated in accordance with conventional methods. The term parenteral as used herein includes subcutaneous injections, intravenous, intramuscular, intraperitoneal injections, or infusion techniques. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a non-toxic parenterally acceptable diluent or solvent, for example, as a solution in water. Among the acceptable vehicles or solvents that may be employed are water, Ringer's solution, and isotonic sodium chloride solution. In addition, sterile, fixed oils are conventionally employed as a solvent or suspending medium. For this purpose any bland fixed oil or fatty acid may be employed including natural, synthetic, or semi-synthetic fatty oils or acids, and natural, synthetic, or semi-synthetic mono-, di-, or triglycerides.

Suppositories for rectal administration of the drug can be prepared by mixing the drug with a suitable non-irritating excipient such as cocoa butter and polyethylene glycols which are solid at ordinary temperatures but liquid at the rectal temperature and will therefore melt in the rectum and release the drug. Solid dosage forms for oral administration may include powders, granules, tablets, pills, and capsules as mentioned above. In such solid dosage forms, the active compound may be admixed with at least one additive such as sucrose, lactose, celluloses, mannitol, maltitol, dextran, starches, agars, alginates, chitins, chitosans, pectins, tragacanth gums, araibic gums, gelatins, collagens, casein, albumin, and synthetic or semi-synthetic polymers or glycerides. Such dosage forms may also comprise, as is normal practice, additional substances other than inert diluents, e.g., lubricating agents as magnesium stearate, preservatives such as parabens and sorbic acid, antioxidants such as ascorbic acid, α-tocopherol and cysteine, disintegrants, binders, thickening, buffering, sweetening, flavoring, and perfuming agents. Tablets and pills can additionally be prepared with enteric coatings. Liquid dosage forms for oral administration may include pharmaceutically acceptable emulsions, syrups, elixirs, suspensions, solutions containing inert diluents commonly used in the art, such as water.

Specific dose levels for any particular patient will be employed depending upon a variety of factors including the activity of specific compounds employed, the age, body weight, general health, sex, diet, time of administration, route of administration, rate of excretion, drug combination, and the severity of the particular disease undergoing therapy. The dose varies with the diseases to be treated, symptoms, subjects and administration routes, and it is desirable that a daily dose of 1 to 50 mg for oral administration or 1 to 30 mg for intravenous injection is divided into 2 to 3 administrations when used as an agent for the therapy in adults. For example, when used for treating adult essential hypertension, the active ingredient will preferably be administered in an appropriate amount, for example, about 10 mg to 100 mg a day orally and about 5 mg to 50 mg a day intravenously. The active ingredient will preferably be administered in equal doses two or three times a day.

The foregoing is merely illustrative of the invention and is not intended to limit the invention to the disclosed compounds.

EXAMPLES

By the following formulation examples, working examples, experimental examples and reference examples, the present invention will be explained more concretely, but they should not be interpreted as limiting the invention in any manner.

Examples of abbreviations in this specification are as follows:

Me: methyl, Et: ethyl, Tet: tetrazolyl, cycl: cyclo-, Pr: propyl, Bu: butyl, Pen: pentyl, Bu: butyl, Hex: hexyl, Hep: heptyl, Ph: phenyl, DMF: dimethylformamide, and THF: tetrahydrofuran.

Formulation Examples

When the compound (I) of the present invention is used as a therapeutic agent for circulatory failures such as hypertension, heart diseases, strokes, kidney diseases, etc., it can be used in accordance with, for example, the following formulations.

1. Capsules

| | |
|---|---|
| (1) 2-ethoxy-1-[[2'-(1H-tetrazol-5-yl)biphenyl-4-yl]-methyl]benzimidazole-7-carboxylic acid | 10 mg |
| (2) lactose | 90 mg |
| (3) fine crystalline cellulose | 70 mg |
| (4) magnesium stearate | 10 mg |
| one capsule | 180 mg |

(1), (2), (3) and a half of (4) are mixed and granulated., To the granules is added the remainder of (4), and the whole is filled into gelatin capsules.

2. Tablets

| | |
|---|---|
| (1) 2-ethoxy-1-[[2'-(1H-tetrazol-5-yl)biphenyl-4-yl]-methyl]benzimidazole-7-carboxylic acid | 10 mg |

-continued

| | | |
|---|---|---|
| (2) lactose | 35 mg | |
| (3) corn starch | 150 mg | |
| (4) fine crystalline cellulose | 30 mg | |
| (5) magnesium stearate | 5 mg | |
| one tablet | 230 mg | |

(1), (2), (3), two thirds of (4) and a half of (5) are mixed and granulated. To the granules are added the remainders of (4) and (5), followed by subjecting the granules to compression molding.

3. Injections

| | |
|---|---|
| (1) 2-methylthio-1-[[2'-(1H-tetrazol-5-yl)biphenyl-4-yl]-methyl]benzimidazole-7-carboxylic acid disodium salt | 10 mg |
| (2) inositol | 100 mg |
| (3) benzyl alcohol | 20 mg |
| one ampoule | 130 mg |

(1), (2) and (3) are dissolved in distilled water for injection to make the whole volume 2 ml, which is filled into an ampoule. The whole process is conducted under sterile conditions.

4. Capsules

| | |
|---|---|
| (1) 1-(cyclohexyloxycarbonyloxy)ethyl 2-ethoxy-1-[[2'-(1H-tetrazol-5-yl)biphenyl-4-yl]-methyl]benzimidazole-7-carboxylate | 10 mg |
| (2) lactose | 90 mg |
| (3) fine crystalline cellulose | 70 mg |
| (4) magnesium stearate | 10 mg |
| one capsule | 180 mg |

(1), (2), (3) and a half of (4) are mixed and granulated. To the granules is added the remainder of (4), and the whole is filled into gelatin capsules.

5. Tablets

| | |
|---|---|
| (1) 1-(cyclohexyloxycarbonyloxy)ethyl 2-ethoxy-1-[[2'-(1H-tetrazol-5-yl)biphenyl-4-yl]-methyl]benzimidazole-7-carboxylate | 10 mg |
| (2) lactose | 35 mg |
| (3) corn starch | 150 mg |
| (4) fine crystalline cellulose | 30 mg |
| (5) magnesium stearate | 5 mg |
| one tablet | 230 mg |

(1), (2), (3), two thirds of (4) and a half of (5) are mixed and granulated. To the granules are added the remainders of (4) and (5), followed by subjecting the granules to compression molding.

6. Injections

| | |
|---|---|
| (1) 2-ethoxy-1-[[2'-(1H-tetrazol-5-yl)biphenyl-4-yl]-methyl]benzimidazole-7-carboxylic acid disodium salt | 10 mg |
| (2) inositol | 100 mg |
| (3) benzyl alcohol | 20 mg |
| one ampoule | 130 mg |

(1), (2) and (3) are dissolved in distilled water for injection to make the whole volume 2 ml, which is filled into an ampoule. The whole process is conducted under sterile conditions.

Reference Example 1

2-Propoxybenzimidazole

To a solution of o-phenylenediamine (2 g) in propyl orthocarbonate (5 ml) was added acetic acid (1.1 ml) and the solution was stirred at 80° C. for 3 hours. To the reaction mixture was added ethyl acetate, and the solution was washed with an aqueous solution of sodium hydrogen carbonate and water, then dried ($Na_2SO_4$), followed by concentration to dryness. The concentrate was purified by column chromatography on silica gel to give crystals. Recrystallization from ethyl acetate-benzene afforded colorless crystals (1.54 g, 47%), m.p. 163–164° C.

Reference Example 2

Ethyl 2-carboxy-3-nitrobenzoate

A mixture of 3-nitrophthalic acid (35 g) in ethanol (300 ml) containing conc. sulfuric acid (20 ml) was heated under reflux for 24 hours. The solvent was evaporated in vacuo and the residue was poured into cold water (700 ml). The mixture was extracted with ethyl acetate. The organic layer was washed with water and shaken with an aqueous solution of potassium carbonate. The aqueous layer was made acidic with hydrochloric acid and the mixture was extracted with methylene chloride. The organic layer was washed with water, then dried, followed by evaporation of the solvent. The resultant solid (29 g, 74%) was used for the subsequent reaction without purification.
$^1$H-NMR(90 MHz, $CDCl_3$) δ: 1.43(3H,t), 4.47(2H,q), 7.70 (1H,t), 8.40(2H,d), 9.87(1H,br s)
IR(Nujol) $cm^{-1}$: 1725, 1535, 1350, 1300, 1270

Reference Example 3

Ethyl 2-t-butoxycarbonylamino-3-nitrobenzoate

A mixture of ethyl 2-carboxy-3-nitrobenzoate (23.9 g) and thionyl chloride (12 ml) in benzene (150 ml) were heated under reflux for 3 hours. The reaction mixture was concentrated to dryness. The resultant acid chloride (26 g, quantitative) was dissolved in methylene chloride (20 ml). The solution was added dropwise to a mixture of sodium azide (9.75 g) in dimethylformamide(DMF) (20 ml) with stirring vigorously. The reaction mixture was poured into a mixture of ether-hexane (3: 1, 200 ml) and water (250 ml) to separate into two layers. The organic layer was washed with water, then dried, followed by evaporation of the solvent. The residue was dissolved in t-butanol (200 ml) and the solution was heated gradually with stirring, followed by heating under reflux for 2 hours. The reaction mixture was concentrated in vacuo to give an oily product (30 g).
$^1$H-NMR(90 MHz, $CDCl_3$) δ: 1.40(3H,t), 1.53(9H,s), 4.43 (2H,q), 7.23(1H,t), 8.03–8.27(2H,m), 9.70(1H,br s)
IR(Neat) $cm^{-1}$: 3320, 2980, 1740, 1585, 1535, 1500, 1440, 1375, 1265, 1155

Working Example 1

Ethyl-2-[(2'-cyanophenyl-4-yl)methyl]amino-3-nitrobenzoate

To solution of ethyl 2-t-butoxycarbonylamino-3-nitrobenzoate (20 g) in tetrahydrofuran (50 ml) was added, while stirring under ice-cooling, sodium hydride (60% dispersion in mineral oil, 2.8 g). The mixture was stirred at room temperature for 20 minutes and to the mixture were then added 4-(2-cyanophenyl)benzyl bromide (18 g) and potassium iodide (360 mg), followed by heating for 10 hours under reflux. The solvent was evaporated to dryness and the residue was partitioned between water (250 ml) and ether (200 ml). The organic layer was washed with water, dried and concentrated to give a yellow syrup. The syrup was dissolved in a mixture of trifluoroacetic acid (60 ml) and methylene chloride (40 ml) and the solution was stirred for one hour at room temperature. The reaction mixture was concentrated to dryness and to the residue was added ethyl ether (200 ml) to give crystals. The crystals were collected by filtration, washed with ether to give pale yellow crystals (22.1 g, 85%), m.p. 118–119° C.
$^1$H-NMR(90 MHz,CDCl$_3$) δ: 1.37(3H,t), 4.23(2H,s), 4.37 (2H,q), 6.37(1H,t), 7.33–7.83(9H,m), 7.97–8.20(2H,m)
IR(Nujol)cm-1: 3280, 2220, 1690, 1575, 1530, 1480, 1450, 1255, 1105, 755

Working Example 2

Ethyl 3-amino-2-[(2'-cyanobiphenyl-4-yl)methyl] aminobenzoate

Dichloride dihydrate (28.1 g) and the mixture was stirred at 80° C. for two hours. The solvent was evaporated to dryness. To the ice-cooling mixture of the residue in ethyl acetate (300 ml) was added dropwise 2N NaOH (500 ml) with stirring. The aqueous layer was extracted with ethyl acetate (200 ml×2). The organic layers were combined, washed with water, and dried. The solvent was evaporated to dryness and the residue was purified by column chromatography on silica gel to give crystals. Recrystallization from ethyl acetate-hexane gave colorless crystals (7.3 g, 79%), m.p. 104–105° C.
$^1$H-NMR(200 MHz, CDCl$_3$) δ: 1.33(3H,t), 4.23(2H,s), 4.27 (2H,q), 6.83–6.93(2H,m), 7.35–7.55(7H,m), 7.64(1H,dt), 7.76(dd)
IR(KBr) cm$^{-1}$: 3445, 3350, 2220, 1680, 1470, 1280, 1240, 1185, 1160, 1070, 1050, 1020, 805, 750

Working Example 3

Ethyl 1-[(2'-cyanobiphenyl-4-yl)methyl]-2-methoxybenzimidazole-7-carboxylate

Acetic acid (0.2 g) was added to a solution of ethyl 3-amino-2-[(2'-cyanobiphenyl-4-yl)methyl]aminobenzoate (1.1 g) in methyl orthocarbonate (5 ml). The mixture was stirred at 80° C. for one hour. The reaction mixture was concentrated, and the concentrate was extracted with ethyl acetate. The organic layer was then washed with an aqueous solution of sodium hydrogen carbonate and water. The solvent was evaporated in vacuo to give crystals. Recrystallization from ethyl acetate-benzene afforded colorless crystals (1.09 g, 90%), m.p. 160–161° C.
$^1$H-NMR(200 MHz, CDCl$_3$) δ: 1.23(3H,t), 4.23(2H,q), 4.26 (3H,s), 5.72(2H,s), 7.09(2H,d), 7.20(1H,t), 7.38–7.48(4H, m), 7.58–7.66(2H,m), 7.73–7.79(2H,m)
IR(KBr) cm$^{-1}$ : 3000, 2220, 1725, 1560, 1465, 1440, 1415, 1285, 1250, 1220, 1040, 760, 750, 740

Working Example 4

Ethyl 1-[(2'-cyanobiphenyl-4-yl)methyl]-2-ethoxybenzimidazole-7-carboxylate

Acetic acid (0.2 g) was added to a solution of ethyl 3-amino-2[(2'-cyanobiphenyl-4-yl)methyl]aminobenzoate (1.0 g) in ethyl orthocarbonate (5 ml).. The mixture was stirred at 80° C. for one hour. The reaction mixture was concentrated, and the concentrate was dissolved in ethyl acetate. The solution was washed with an aqueous solution of sodium hydrogen carbonate and water. The solvent was evaporated to give crystals. Recrystallization from ethyl acetate-benzene afforded colorless crystals (0.79 g, 69%), m.p. 131–132° C. Elemental Analysis for $C_{26}H_{23}N_3O_3$:

|  | C (%) | H (%) | N (%) |
|---|---|---|---|
| Calcd.: | 73.39; | 5.45; | 9.88 |
| Found: | 73.36; | 5.42; | 9.83 |

$^1$H-NMR(20 MHz, CDCl$_3$) δ: 1.24(3H,t), 1.49(3H,t), 4.24 (2H,q), 4.68(2H,q), 5.72(2H,s), 7.10(2H,d), 7.19(1H,t), 7.38–7.46(4H,m), 7.56–7.66(2H,m), 7.73–7.77(2H,m)
IR(KBr) cm$^{-1}$: 2220, 1720, 1550, 1480, 1430, 1280, 1245, 1215, 1040, 760, 740

Working Example 5

Ethyl 1-[(2'-cyanobiphenyl-4-yl)methyl]-2-propoxybenzimidazole-7-carboxylate

Acetic acid (0.2 g) was added to a solution of ethyl 3-amino-2-[(2'-cyanobiphenyl-4-yl)methyl]aminobenzoate (0.9 g) in propyl orthocarbonate (5 ml). The mixture was stirred at 80° C. for one hour. The reaction mixture was concentrated, and the concentrate was dissolved in ethyl acetate. The solution was washed with an aqueoues solution of sodium hydrogen carbonate. The solvent was evaporated to give crystals. Recrystallization from ethyl acetate-benzene afforded colorless crystals (0.72 g, 68%), m.p. 90–92° C. Elemental Analysis for $C_{27}H_{25}N_3O_3$:

|  | C (%) | H (%) | N (%) |
|---|---|---|---|
| Calcd.: | 73.79; | 5.73; | 9.56 |
| Found: | 73.84; | 5.79; | 9.54 |

$^1$H-NMR(200 MHz, CDCl$_3$) δ: 1.01(3H,t), 1.25(3H,t), 1.80–1.97 (2H,m), 4.24(2H,q), 4.57(2H,q), 5.72(2H,s), 7.11 (2H,d), 7.19(1H,t), 7.38–7.46(4H,m), 7.56–7.66(2H,m), 7.73–7.77(2H,m)
IR(KBr) cm$^{-1}$: 2220, 1725, 1550, 1480, 1460, 1430, 1370, 1280, 1245, 1210, 1115, 1040, 760, 750, 740

Working Example 6

Ethyl 1-[(2'-cyanobiphenyl-4-yl)methyl]-2-mercaptobenzimidazole-7-carboxylate

A mixture of ethyl 3-amino-2-[(2'-cyanobiphenyl-4-yl)-methyl]aminobenzoate (5.6 g) and sodium O-ethyl dithiocarbonate (7.3 g) in ethanol (50 ml) was heated for 8 hours under reflux. The reaction mixture was concentrated and the residue was dissolved in water. The solution was adjusted to pH 3–4 with hydrochloric acid. Precipitating crystals were collected by filtration, followed by recrystallization from ethanol to afford yellow crystals (5.0 g, 80%), m.p. 225–227° C.

¹H-NMR(200 MHz, DMSO-d₆) δ: 1.08(3H,t), 4.12(2H,q), 5.90(2H,brs), 7.08(2H,d), 7.27(1H,t), 7.38–7.59(6H,m), 7.76(1H,dt), 7.92(1H,dd)
IR(KBr) cm⁻¹: 2210, 1720, 1460, 1440, 1420, 1375, 1335, 1265, 1180, 1135, 1115, 1100, 985, 760, 740

Reference Example 4

Methyl 2-[[(2'-cyanobiphenyl)methyl]amino]-3-nitrobenzoate

A mixture of ethyl 2-[[(2'-cyanobiphenyl)methyl]amino]-3-nitrobenzoate (5 g) and sodium hydride (60% dispersion in mineral oil, 1.62 g) in methanol (50 ml) was stirred at room temperature for one day. The reaction mixture was concentrated and the residue was poured into a saturated aqueous solution of sodium hydrogen carbonate (100 ml), followed by extraction with chloroform. The organic layer was washed with water, dried and concentrated to dryness to give crystals. Recrystallization from ethyl acetate-hexane afforded pale yellow crystals (3.98 g, 83%), m.p. 106–108° C.

¹H-NMR(200 MHz, CDCl₃) δ: 3.81(3H,s), 3.97(2H,br s), 4.23(2H,s), 6.40(1H,br s), 6.88–6.91(2H,m), 7.34–7.55 (7H,m), 7.65(1H,dt,J=1.2, 7.7 Hz), 7.77(1H,dd,J=1.4, 8.0 Hz)
IR(KBr) cm⁻¹: 3410, 3350, 2225, 1695, 1485, 1470, 1290, 1200, 780, 760

Working Example 7

Methyl 1-[(2'-cyanobiphenyl-4-yl)methyl]-2-ethoxybenzimidazole-7-carboxylate Acetic acid (0.37 g) was added to a solution of methyl 3-amino-2-[[(2'-cyanobiphenyl-4-yl)methyl]amino] benzoate (2.03 g) in ethyl orthocarbonate (5 ml), and the mixture was stirred at 80° C. for one hour. The reaction mixture was concentrated to dryness and the residue was dissolved in ethyl acetate. The solution was washed with an aqueous solution of sodium hydrogen carbonate and water. The solvent was evaporated in vacuo to give crystals. Recrystallization from ethyl acetate-hexane afforded colorless crystals (2.01 g, 86%), m.p. 168.5–169.5° C.
Elemental Analysis:

|  | C (%) | H (%) | N (%) |
| --- | --- | --- | --- |
| Calcd.: | 72.98; | 5.14; | 10.21 |
| Found: | 72.71; | 5.12; | 9.97 |

¹H-NMR(200 MHz,CDCl₃) δ: 1.42(3H,t,J=7.1 Hz), 3.71 (3H,s), 4.63(2H,q,J=7.1 Hz), 5.59(2H,s), 7.09(2H,d,J=8.4 Hz), 7.20(1H,t,J=7.9 Hz), 7.45–7.59(5H,m), 7.69–7.80(2H, m), 7.92(1H,dd,J=1.4,7.8 Hz)
IR(KBr) cm⁻¹: 2225, 1725, 1550, 1480, 1430, 1350, 1280, 1250, 1040, 760, 750

Reference Example 5

Ethyl 2-[[(2'-cyanobiphenyl-4-yl)methyl]amino]-3-(3-ethylthioureido)benzoate A mixture of ethyl 3-amino-2-[[(2'-cyanobiphenyl-4-yl)-methyl]amino]benzoate (1.61 g), ethyl isothiocyanate (1.5 ml) and ethanol (1 ml) was stirred at room temperature for 3 days. The reaction mixture was dissolved in ethyl acetate and the solution was washed with water, dried and concentrated to dryness to give crystals. Recrystallization from ethyl acetate-hexane afforded pale yellow crystals (1.92 g, 91%), m.p. 108–110° C.
¹H-NMR(200 MHz,CDCl₃) δ: 1.15(3H,t), 1.40(3H,t), 3.50–3.70(2H,brs), 4.37(2H,q), 4.56(2H,d), 6.07(1H,t), 6.78 (1H,t), 7.19–7.24(1H,m), 7.38–7.53(6H,m), 7.63(1H,dt), 7.72–7.76(1H,m), 7.99(1H,dd), 8.29(1H,br s)
IR(KBr) cm⁻¹: 3375, 3320, 3150, 2975, 2220, 1740, 1680, 1540, 1510, 1450, 1300, 1225, 1180, 1150, 760, 750

Reference Example 6

Ethyl 2-[[(2'-cyanobiphenyl-4-yl)methyl]amino]-3-(3-propylthioureido)benzoate In substantially the same manner as Reference Example 5, desired pale yellow syrup (2.0 g, 98%) was obtained from ethyl 3-amino-2-[[(2'-cyanobiphenyl-4-yl)methyl]amino] benzoate (1.6 g), propyl isothiocyanate (1.5 ml) and ethanol (1 ml).
¹H-NMR(200 MHz,CDCl₃) δ: 0.88(3H,t), 1.40(3H,t), 1.48–1.67(2H,m), 3.42–3.68(2H,br s), 4.37(2H,q), 4.56(2H, d), 6.13(1H,t), 6.78(1H,t), 7.21–7.25(1H,m), 7.36–7.53(6H, m), 7.64(1H,dt), 7.73–7.77(1H,m), 7.99(1H,dd), 8.20–8.40 (1H,br s)
IR(Neat)cm⁻¹: 3325, 3175, 2960, 2930, 2875, 2220, 1710, 1690, 1590, 1475, 1360, 1175, 1140, 1090, 1020, 760

Working Example 8

Ethyl 1-[(2'-cyanobiphenyl-4-yl)methyl]-2-ethylaminobenzimidazole-7-carboxylate Methyl iodide (4.5 g) was added to a solution of ethyl 2-[[(2'-cyanobiphenyl-4-yl)methyl]amino]-3-(ethylthioureido)benzoate (1.8 g) in ethanol (50 ml), and the mixture was heated under reflux for 12 hours. To the reaction mixture was added 1N-HCl (60 ml) and the mixture was stirred at room temperature for 30 minutes. The reaction mixture was concentrated to dryness and the concentrate was dissolved in ethyl acetate. The solution was washed with an aqueous solution of sodium hydrogen carbonate and water and dried. The solvent was evaporated to dryness and the residue was purified by column chromatography on silica gel to afford yellow syrup (0.96 g, 58%).
¹H-NMR(200 MHz,CDCl₃) δ: 1.23(6H,t), 3.48–3.62(2H, m), 4.09(1H,t), 4.23(2H,q), 5.57(2H,s), 7.15(1H,t), 7.25(2H, d), 7.40–7.77(8H,m)
IR(Neat)cm⁻¹: 3400, 3225, 2975, 2930, 2210, 1710, 1610, 1570, 1480, 1425, 1365, 1320, 1270, 1250, 1210, 1130, 1100, 1060, 770, 750

Working Example 9

Ethyl 1-[(2'-cyanobiphenyl-4-yl)methyl]-2-propylaminobenzimidazole-7-carboxylate In substantially the same manner as Working Example 8, desired yellow syrup (1.2 g, 65%) was obtained from a solution of ethyl 2-[[(2'-cyanobiphenyl-4-yl)methyl]amino]-3-(3-propylthioureida)-benzoate (2.0 g) and methyl iodide (4.8 g) in ethanol (50 ml).
¹H-NMR(200 MHz,CDCl₃) δ: 0.87(3H,t), 1.25(6H,t), 1.52–1.70(2H,m), 3.42–3.52(2H,m), 4.12(1H,t), 4.25(2H,q), 5.58(2H,s), 7.16(1H,t), 7.29(2H,d), 7.41–7.78(8H,m)
IR(Neat)cm⁻¹: 3400, 3250, 2975, 2950, 2890, 2225, 1715, 1620, 1590, 1570, 1480, 1430, 1370, 1285, 1220, 1135, 1070, 760

Working Example 10

Methyl 1-[(2'-cyanobiphenyl-4-yl)methyl]-2-methoxybenzimidazole-7-carboxylate A solution of 5.2 M sodium methoxide in methanol (0.5 ml) was added to a solution of ethyl 1-[(2'-cyanobiphenyl- 4-yl)methyl]2-methoxybenzimidazole-7-carboxylate (1.3 g) in methanol (50 ml). The mixture was heated for 4 hours under reflux. The reaction mixture was concentrated, and the precipitated crystals were collected by filtration. Recrystallization from methanol afforded colorless prisms (1.1 g, 85%), m.p. 149–150° C.
Elemental Analysis for $C_{24}H_{19}N_3O_3$:

|  | C (%) | H (%) | N (%) |
|---|---|---|---|
| Calcd.: | 72.53; | 4.82; | 10.57 |
| Found: | 72.38; | 4.93; | 10.44 |

$^1$H-NMR(200 MHz,CDCl$_3$) δ: 3.75(3H,s), 4.26(3H,s), 5.69 (2H,s), 7.09(2H,d), 7.23(1H,t), 7.37–7.46(3H,m), 7.55–7.65 (2H,m), 7.72–7.78(2H,m)

Reference Example 7

Methyl 2-[[(2'-cyanobiphenyl-4-yl)]methyl]amino-3-(3-methylthioureido)benzoate

The above compound was synthesized (86% yield) in substantially the same manner as Reference Example 5. m.p. 152–155° C.
$^1$H-NMR(200 MHz,CDCl$_3$) δ: 3.05–3.07(3H,br s), 3.92(3H, s), 4.58(2H,d), 6.04–6.08(1H,br s), 6.77(1H,t), 7.22–7.26 (1H,m), 7.39–7.52(6H,m), 7.63(1H,dt), 7.75(1H,dd), 7.97 (1H,dd), 8.28(1H,br s)
IR(KBr) cm$^{-1}$: 3375, 3325, 3175, 2220, 1680, 1590, 1540, 1500, 1480, 1450, 1435, 1265, 1230, 1190, 1145, 1050, 830, 760, 740

Working Example 11

Methyl 1-[(2'-cyanobiphenyl-4-yl)methyl]-2-methylaminobenzimidazole-7-carboxylate The above compound was synthesized as a syrup (42% yield) in substantially the same manner as Working Example 8.
$^1$H-NMR(200 MHz,CDCl$_3$) δ: 3.11(3H,d), 3.73(3H,s), 4.22 (1H,q), 5.54(2H,s), 7.17(1H,t), 7.27(2H,d), 7.41–7.79(8H, m)
IR(Neat)cm$^{-1}$: 3400, 3250, 3025, 2950, 2220, 1720, 1625, 1610, 1580, 1480, 14110, 13340, 1280, 1240, 1210, 1130, 1060, 750

Reference Example 8

2-Propoxy-1-[[2'-(1H-tetrazol-5-yl)biphenyl-4-yl] methyl]-benzimidazole

Sodium hydride (60% dispersion in mineral oil, 0.24 g) was added to a stirred solution of 2-propoxybenzimidazole (0.71 g) in DMF (10 ml) under ice-cooling. The mixture was stirred for 20 minutes, to which was added N-triphenylmethyl-5-[2-(4-bromomethylbiphenyl]-tetrazole (2.3 g), followed by stirring at room temperature for 5 hours. To the reaction mixture was added ice-water, the mixture was extracted with ethyl acetate. The organic layer was washed with water, dried and concentrated to dryness. The concentrate was dissolved in methanol (50 ml), to which was added 1N-HCl (15 ml), followed by stirring at 60° C. for 2 hours. The reaction mixture was concentrated, to which were added water (15 ml) and ethyl acetate (15 ml). The mixture was made alkaline with 1N NaOH and shaken. The aqueous layer was adjusted to pH 3–4 with 1N-HCl and then extracted with chloroform. The organic layer was washed with water, dried and concentrated to dryness. The concentrate was purified by column chromatography on silica gel to yield crystals. Recrystallization from ethyl acetate-methanol gave colorless crystals (0.58 g, 35%), m.p. 177–179° C. (decomp.).
Elemental Analysis for $C_{24}H_{22}N_6O$:

|  | C (%) | H (%) | N (%) |
|---|---|---|---|
| Calcd.: | 70.23; | 5.40; | 20.47 |
| Found: | 69.93; | 5.43; | 20.22 |

$^1$H-NMR(200 MHz,DMSO-d$_6$) δ: 0.95(3H,t), 1.70–1.88 (2H,m), 4.46(2H,t), 5.23(2H,s), 7.04–7.10(4H,m), 7.20(2H, d), 7.38–7.43(2H,m), 7.48–7.70(4H,m)
IR(KBr) cm$^{-1}$: 1540, 1535, 1485, 1475, 1450, 1425, 1385, 1285, 1270, 1040, 980, 755, 745

Working Example 12

Methyl 2-butylamino-1-[(2'-cyanobiphenyl-4-yl) methyl]-benzimidazole-7-carboxylate The title compound was prepared from methyl 2-[[(2'-cyanobiphenyl-4-yl)methyl]amino]-3-(butylureido) benzoate in substantially the same manner as Working Example 8. The yield was quantitative.
$^1$H-NMR(200 MHz,CDCl$_3$) δ: 0.89(3H,t), 1.21–1.39(2H, m), 1.45–1.60(2H,m), 3.50–3.65(3H,brs), 3.92(3H,s), 4.56 (2H,d), 6.08(1H,t), 6.78(1H,t), 7.21–7.30(1H,m), 7.39–7.54 (6H,m), 7.64(1H,dt), 7.75(1H,dd), 7.98(1H,dd), 8.26(1H, brs)

Working Example 13

Methyl 2-(N-ethylmethylamino)-1-[(2'-cyanobiphenyl-4-yl)-methyl]benzimidazole-7-carboxylate A mixture of sodium hydride (60% dispersion in mineral oil, 0.13 g) in DMF (5 ml) was stirred under ice-cooling for 5 min. and methyl 2-ethylamino-1-[(2'-cyanobiphenyl-4-yl) methyl]benzimidazole-7-carboxylate (0.95 g) was added to the mixture, followed by stirring for 10 min. To the mixture was added methyl iodide (0.2 ml) and the mixture was stirred for 20 min. To the reaction mixture was added water and the mixture was extracted with ethyl acetate. The extract was washed with water, dried and evaporated to dryness. The residue was purified by column chromatography on silica gel to give crude cristals, which were recrystallized from ethyl acetate-hexane to afford colorless needles (0.88 g, 82%), m.p. 66–69° C.
$^1$H-NMR(200 MHz,CDCl$_3$) δ: 1.25(3H,tI, 3.03(3H,s), 3.36 (2H,q), 3.73(3H,s), 5.60(2H,s), 6.88(2H,d), 7.16(1H,t), 7.34–7.49(5H,m), 7.59(1H,dt), 7.73(1H,dd), 7.78(1H,dd)
IR(KBr) cm$^{-1}$: 2210, 1710, 1540, 1530, 1435, 1420, 1385, 1300, 1275, 1250, 1005, 760

Reference Example 9

Methyl 1-[(2'-cyanobiphenyl-4-yl)methyl]-2-oxo-2, 3-dihydrobenzimidazole-7-carboxvlate To a solution of methyl 2-[(2'-cyanobiphenyl-4-yl)-methylamino]-3-methoxycarbonylaminobenzoate (10.5 g) in methanol (100 ml) was added NaOMe (10 g), and the mixture was heated under reflux for 20 hours. The reaction mixture was neutralized with 1N-HCl and concentrated to dryness. The residue was extracted with chloroform-water. The organic layer was washed with water, dried and evaporated to dryness. The resulting crystals were recrystallized from chloroform-methanol to afford colorless needles (8.67 g, 89%), m.p. 250–253° C.
$^1$H-NMR(200 MHz,DMSO-$d_6$) δ: 3.65(3H,s), 5.35(2H,s), 7.04–7.16(3H.m), 7.24–7.28(2H,m), 7.48–7.59(4H,m), 7.76 (1H,dt), 7.92(1H,dd)
IR(KBr) cm$^{-1}$: 2210, 1720, 1690, 1635, 1430, 1390, 1270, 1255, 760, 750, 730, 690

Reference Example 10

Methyl 2-chloro-1-[(2'-cyanobiphenyl-4-yl)methyl]-benzimidazole-7-carboxylate

A mixture of methyl 1-[(2'-cyanobiphenyl-4-yl)methyl]-2-oxo-2,3-dihydrobenzimidazole-7-carboxylate (8.02 g) in phosphorus oxychloride (30 ml) was heated under reflux for 8 hours. The reaction mixture was concentrated and the resulting residue wag poured into ice-water. The mixture was extracted with chloroform. The extract was washed with water, dried and evaporated. The residue was purified by column chromatography on silica gel to give crystals, which were recrystallized from chloroform-methanol to afford colorless needles (2.2 g, 28%), m.p. 154–157° C.
$^1$H-NMR(200 MHz,CDCl$_3$) δ: 3.78(3H,s), 5.95(2H,s), 7.06 (2H,d), 7.31(1H,t), 7.39–7.48(4H,m), 7.58–7.66(1H,m), 7.71–7.77(2H,m), 7.93(1H,dd)
IR(KBr) cm$^{-1}$: 2240, 1720, 1480, 1450, 1440, 1425, 1370, 1350, 1290, 1270, 1200, 1150, 1120, 1000, 775, 760, 750

Reference Example 11

Methyl 2-[(2'-cyanobiphenyl-4-yl)methylamino]-3-methoxycarbonylaminobenzoate

To a stirred solution of methyl 3-amino-2-[(2'-cyanobiphenyl-4-yl)methylamino]benzoate (10 g) in pyridine (50 ml) was added dropwise methyl chloroformate (9.0 ml) under ice-cooling. The mixture was stirred at room temperature for 3 hours and concentrated. The residue was extracted with ethyl acetate. The extract was washed with water, dried and evaporated. The residue was recrystallized from ethyl acetate-hexane to afford pale yellow needles (10.5 g, 90%), m.p. 113–115° C.
$^1$H-NMR(200 MHz,CDC$_3$) δ: 3.80(3H,s), 3.83(3H,s), 4.11 (2H,d), 6.29(1H,brs), 7.09(1H,t), 7.40–7.80(10H,m), 8.19 (1H,d)

Working Example 14

Methyl 1-[(2'-cyanobiphenyl-4-yl)methyl]-2-morpholinobenzimidazole-7-carboxylate A mixture of methyl 2-chloro-1-[(2'-cyanobiphenyl-4-yl)-methyl]benzimidazole-7-carboxylate (0.8 g) in morpholine (15 ml) was stirred at 100° C. for 2 hours and the reaction mixture was concentrated to dryness. The residue was extracted with ethyl acetate. The extract was washed with water, dried and evaporated. The resulting crystals were recrystallized from ethyl acetate-hexane to afford colorless prisms (0.69 g, 77%).
$^1$H-NMR(200 MHz,CDCl$_3$) δ: 3.38(4H,t), 3.72(3H,s), 3.90 (4H,t), 5.63(2H,s), 6.89(2H,d), 7.20(1H,t), 7.37–7.65(6H, m), 7.74(1H,dd), 7.82(1H,dd)
IR(KBr) cm$^{-1}$: 2225, 1715, 1520, 1440, 1415, 1280, 1260, 1220, 1130, 1120, 1010, 860, 770, 760, 750

Working Example 15

Methyl 1-[(2'-cyanobiphenyl-4-yl)methyl]-2-piperidinobenzimidazole-7-carboxylate The title compound was prepared in substantially the same manner as Working Example 14. Yield: 81%, m.p. 119–121° C.
$^1$H-NMR(200 MHz,CDCl$_3$) δ: 1.62–1.77(6H,m), 3.31–3.36 (4H,m), 3.73(3H,s), 5.58(2H,s), 6.88(2H,d), 7.15(1H,t), 7.35–7.49(5H,m), 7.56–7.64(1H,m), 7.73(1H,dd), 7.79(1H, dd)
IR(KBr) cm$^{-1}$: 2225, 1720, 1530, 1445, 1410, 1385, 1305, 1285, 1265, 1250, 1130, 1110, 770, 750

Reference Example 12

Methyl 2-[(2'-methoxycarbonylbiphenyl-4-yl) methylamino]-3-nitrobenzoate

To a solution of methyl 2-tert-butoxycarbonylamino-3-nitrobenzoate (1.84 g) in acetonitrile (10 ml) was added a solution of 4-(2'-methoxycarbonylbiphenyl-4-yl)methyl bromide (1.9 g) in acetonitrile (5 ml) and potassium carbonate (0.86 g) and the reaction mixture was heated under reflux for 20 hours. The reaction mixture was concentrated to dryness and the resulting residue was extracted with ethyl acetate and water. The organic layer was washed with water, dried and evaporated. The residue was purified by column chromatography on silica gel to give pale yellow syrup. The syrup was dissolved in ethanol (10 ml) and 20% hydrochloric acid in ethanol (4 ml) was added to the solution. The reaction mixture was stirred at room temperature for 22 hours and concentrated to dryness. The residue was dissolved in ethyl acetate and the solution was washed with saturated aqueous sodium bicarbonate and water, dried and evaporated to afford yellow syrup (1.39 g, 53%).
$^1$H-NMR(200 MHz,CHCl$_3$) δ: 3.61(3H,s), 3.89(3H,s), 4.21 (2H,d), 6.72(1H,t), 7.30(4H,d), 7.36(1H,dd), 7.42(1H,dd), 7.53(1H,dd), 7.82(1H,dd), 8.00(1H,dd), 8.10(1H,dd)

Reference Example 13

Methyl 3-amino-2-[(2'-methoxycarbonylbiphenyl-4-yl)methylamino]benzoate

The title compound was prepared as pale yellow syrup from methyl 2-[(2'-methcxycarbonylbiphenyl-4-yl) methylamino]-3-nitrobenzoate in substantially the same manner as Working Example 2. Yield: 79%.
$^1$H-NMR(200 MHz,CHCl$_3$) δ: 3.63(3H,s), 3.80(3H,s), 3.97 (2H,brs), 4.22(2H,d), 6.40(1H,brs), 6.82–6.92(2H,m), 7.23–7.44(7H,m), 7.53(1H,dt), 7.79–7.83(1H,m)
IR(Neat) cm$^{-1}$: 3450, 3360, 2970, 1730, 1700, 1470, 1460, 1450, 1440, 1290, 1250, 1200, 770, 750

Working Example 16

Methyl 2-ethoxy-1- [(2'-methoxycarbonylbiphenyl-4-yl) methyl]benzimidazole-7-carboxylate The title compound was prepared as colorless plates from methyl 3-amino-2-[(2'-methoxycarbonylbiphenyl-4-yl) methylamino]-benzoate in substantially the same manner as Working Example 4. Yield: 72%, m.p. 112–113° C.
$^1$H-NMR(200 MHz,CHCl$_3$) δ: 1.50(3H,t), 3.55(3H,s), 3.77 (3H,s), 4.68(2H,q), 5.65(2H,s), 6.99(2H,d), 7.17(2H,d), 7.17 (1H,t), 7.31–7.55(4H,m), 7.73(1H,dd), 7.77(1H,dd)
IR(Neat)cm$^{-1}$: 1730, 1710, 1545, 1470, 1430, 1380, 1340, 1320, 1270, 1250, 1235, 1210, 1120, 1080, 1030, 750, 740, 710

Working Example 17

Methyl 2-butoxy-1-[(2'-cyanobiphenyl-4-yl)methyl]benzimidazole7-carboxylate

The title compound was prepared as colorless needles in substantially the same manner as Working Example 7.
Yield: 75%, m.p. 74–75° C.
$^1$H-NMR(200 MHz,CDCl$_3$) δ: 0.95(3H,t), 1.35–1.54(2H,m), 1.77–1.90(2H,m), 3.76(3H,s), 4.60(2H,t), 5.69(2H,s), 7.10(2H,d), 7.17(1H,t), 7.43(4H,d), 7.54–7.65(2H,m), 7.74(2H,dd)
IR(KBr) cm$^{-1}$: 2220, 1725, 1560, 1490, 1470, 1440, 1395, 1320, 1295, 1265, 1245, 1120, 1050, 1020, 770

Working Example 18

Methyl 2-allyloxy-1-[(2'-cyanobiohenyl-4-yl)methyl]benzimidazole-7-carboxylate The title compound was prepared as colorless plates in substantially the same manner as Working Example 7.
Yield: 73%, m.p. 118–119° C.
$^1$H-NMR(200 MHz,CDCl$_3$) δ: 3.76(3H,s), 5.12(2H,m), 5.33(1H,m), 5.43(1H,m), 5.72(2H,s), 6.02–6.21(1H,m), 7.11(2H,d), 7.19(1H,t), 7.44(4H,d), 7.56–7.66(2H,m), 7.75(2H,dd)
IR(KBr) cm$^{-1}$: 2220, 1705, 1540, 1470, 1460, 1425, 1410, 1400, 1330, 1300, 1270, 1 250, 1225, 1205, 1100, 1015, 995, 760, 750, 740, 730

Working Example 19

Methyl 2-ethylamino-1-[(2'-cyanobiphenyl-4-yl)methyl]-benzimidazole-7-carboxylate The title compound was prepared as colorless crystals (3.2 g, 32%) according to the procedure for Working Example 8 from methyl 2-[[(2'-cyanobiphenyl-4-yl)methyl]amino]-3-(3-ethylthioureido)benzoate (10.5 g), which was synthesized from methyl 3-amino-2-[[(2'-cyanobiphenyl-4-yl)methyl]amino]benzoate in substantially the same manner as Reference Example 5.
$^1$H-NMR(200 MHz,CDCl$_3$) δ: 1.24(3H,t), 3.49–3.63(2H,m), 4.06(1H,t), 5.55(2H,s), 7.16(1H,t), 7.27(2H,d), 7.41–7.79(8H,m)
IR(KBr) cm$^{-1}$: 3275, 2225, 1720, 1620, 1610, 1580, 1570, 1480, 1350, 1275, 1240, 1215, 1100, .1070, 770, 760

Working Example 20

2-Cyano-4'-methylbiphenyl

20a) N-(2-Methoxyphenyl)methylidenecyclohexylamine

A solution of anisaldehyde (21 g) and cyclohexylamine (15 g) in chloroform. (100 ml) was stirred at room temperature for 2 hours and evaporated to afford brown syrup (35 g, quantitative).
$^1$H-NMR(200 MHz,CDCl$_3$) δ: 1.21–1.87(10H,m), 3.14–3.28(1H,m), 3.86(3H,s), 6.88–7.00(2H,m), 7.36(1H,m), 7.95(2H,dd), 8.75(1H,s)

20b) 4'-Methyl-2-biphenylcarbaldehyde

To a suspension of magnesium metal (1.1 g) in THF (3 ml) was added dropwise a solution of 4-bromotoluene (7.5 g) in THF (10 ml) under gentle reflux. The resulting solution of the Grignard reagent was added dropwise to an ice-cooled, stirred solution of N-(2-methoxyphenyl)methylidenecyclohexylamine (4.3 g) in THF (30 ml). The reaction mixture was stirred at room temperature for 1.5 hours, followed by heating under reflux for 7 hours. After addition of ice-water, the reaction mixture was acidified with conc. hydrochloric acid. The reaction mixture was extracted with ethyl acetate and the extract was washed with 1N-hydrochloric acid and water, dried and evaporated to dryness. The residue was purified by column chromatography on silica gel to give pale yellow syrup (2.0 g, 51%).
$^1$H-NMR(200 MHz,CDCl$_3$) δ: 2.43(3H,s), 7.28(4H,s), 7.42–7.51(2H,m), 7.63(1H,t), 8.02(1H,d), 10.00(1H,s)

20c) 2-Cyano-4'-methyibiphenyl

A mixture of 4'-methyl-2-biphenylcarbaldehyde (2.0 g) and hydroxyamine hydrochloride (1.0 g) in pyridine (10 ml) was stirred at room temperature for 15 min., followed by addition of acetic anhydride (4.1 g). The reaction mixture was stirred at 90–100° C. for 1 hr. and concentrated to dryness. After addition of water to the residue, the precipitated crystals were collected by filtration. Recrystallization from hexane gave colorless needles (1.5 g, 79%).
$^1$H-NMR(90 MHz,CDCl$_3$) δ: 2.40(3H,s), 7.2–7.8(8H,m)
The title compound can be readily converted into Compoud (IIIa') according to the known references as mentioned above.

Working Example 21

Methyl 2-carboxy-3-nitrobenzoate

To a suspension of 3-nitrophthalic acid (211 g) and methyl orthoformate (127 g) in methanol (420 ml) was added conc. sulfuric acid (20 ml) dropwise with stirring. The reaction mixture was heated under reflux for 18 hours and concentrated to dryness. After addition of water (30 ml) to the residue, the mixture was stirred at 3–10° C. for one hour. The precipitated crystals were recrystallized from ethyl acetate-hexane to give pale yellow prisms (185 g, 82%), m.p. 166–168° C.
$^1$H-NMR(200 MHz, CDCl$_3$) δ: 4.03(3H,s), 7.74(1H,t), 8.39(1H,dd), 8.42(1H,dd)

Working Example 22

Methyl 2-tert-butoxycarbonylamino-3-nitrobenzoate

To a solution of methyl 2-carboxy-3-nitrobenzoate (7.23 g) in DMF (50 ml) was added diphenylphosphoryl azide (11.3 g) at room temperature and then triethylamine (6.7 ml) was added dropwise to the stirred reaction mixture. After stirring at room temperature for 3 hours, tert-butanol (54 ml) was added to the stirred reaction mixture. After stirring at room temperature for 30 min., the reaction mixture was gradually warmed, then heated under reflux for 1 hour and evaporated to dryness. The resultant residue was dissolved in ethyl acetate, washed with dilute hydrochloric acid, aqueous sodium bicarbonate, and water, and then dried. After evaporation of the solvent, methanol was added to the resultant residue and the mixture was cooled to give colorless crystals (6.7 g, 70%).
$^1$H-NMR(200 MHz, CDCl$_3$) δ: 1.50(9H,s), 3.96(3H,s), 7.23(1H,t), 8.10(1H,dd), 8.17(1H,dd)
IR(KBr) cm$^{-1}$: 3360, 1730, 1705, 1580, 1520, 1490, 1440, 1365, 1355, 1310, 1270, 1240, 1150, 870, 835, 770, 725, 705

Working Example 23

Methyl 2-[[N-tert-butoxycarbonyl-N-(2'-cyanobiphenyl-4-yl)methyl]amino]-3-nitrobenzoate A solution of methyl 2-tert-butoxycarbonylamino-3-nitrobenzoate (0.6 g), 2-(4-bromomethylphenyl)benzonitrile (0.54 g) and K$_2$CO$_3$ (0.28 g) in acetonitrile (10 ml) was heated under reflux for 4 hours and concentrated to dryness. Water was added to the resultant residue and the mixture was extracted with ethyl acetate. The extract was washed with water, dried and evaporated to dryness. The residue was purified by column chromatography on silica gel to give crystals. Recrystallization from ethyl acetate-hexane afforded colorless prisms (0.83 g, 85%), m.p. 153–154° C.
$^1$H-NMR(200 MHz,CDCl$_3$) δ: 1.35(9H,s), 3.70(3H,s), 4.63 (1H,d), 4.80(1H,d), 7.23–7.29(3H,m), 7.39–7.53(6H,m), 7.59–7.67(1H,m), 7.75(1H,dd), 7.93(1H,dd), 7.99(1H,dd), 8.05(1H,dd), 8.11(1H,dd)
IR(KBr) cm$^{-1}$: 2220, 1700, 1530, 1390, 1360, 1315, 1290, 1160, 765

Working Example 24

Methyl 2-[[2'-cyanobiphenyl-4-yl)methyl]amino]-3-nitrobenzoate

A mixture of methyl 2-[[N-tert-butoxycarbonyl-N-(2'-cyanobiphenyl-4-yl)methyl]amino]-3-nitrobenzoate (0.49 g) in 20% HCl-ethanol (3 ml) and ethyl acetate (3 ml) was stirred at room temperature for 1 hour. After evaporation of the solvent, to the residue was added methanol and saturated aqueous sodium bicarbonate to give crystals. The crystals were collected by filtration and recrystallized from chloroform-methanol to give pale yellow crystals (0.3 g, 77%), m.p. 140–141° C.
$^1$H-NMR(200 MHz, DMSO-d$_6$) δ: 3.84(3H,s), 4.26(2H,m), 6.86(1H,t), 7.46(2H,d), 7.54–7.65(4H,m), 7.79(1H,d), 7.95 (dd), 8.05–8.11(2H,m), 8.67(1H,t)

Working Example 25

Methyl 3-amino-2-[[(2'-cyanobiphenyl-4-yl)methyl] amino]benzoate

A mixture of methyl 2-[[(2'-cyanobiphenyl-4-yl)methyl] amino]-3-nitrobenzoate (10 g), FeCl$_3$.6H$_2$O (0.1 g), activated charcoal (1 g) in a mixture of methanol (100 ml) and THF (50 ml) was heated under reflux for 30 min. Hydrazine hydrate (7.2 ml) was added dropwise to the reaction mixture and the mixture was then heated under reflux for 14 hours. The insoluble material was removed from the reaction mixture by filtration and the filtrate was concentrated to dryness. Aqueous sodium bicarbonate was added to the resulting residue and the mixture was extracted with ethyl acetate. The extract was washed with water, dried and evaporated to dryness. The residue was purified by column chromatography on silica gel to give crystals. Recrystallization from isopropyl ether afforded pale yellow needles (6.0 g, 64%), m.p. 110–111° C.
$^1$H-NMR(200 MHz,CDCl$_3$) δ: 3.81(3H,s), 3.97(2H,brs), 4.23(2H,d), 6.39(1H,t), 6.84–6.93(2H,m), 7.26–7.55(8H,m), 7.64(1H,dt), 7.77(1H,dd)

Working Example 26

Methyl 1-[(2'-cyanobiphenyl-4-yl)methyl]-2-(2,2,2-trifluoroethoxy)benzimidazole-7-carboxylate The title compound was prepared as pale yellow crystals from methyl 3-amino-2-[[(2'-cyanobiphenyl-4-yl)methyl] amino]benzoate and 2,2,2-trifluoroethyl orthocarbonate according to the procedure for Working Example 3. Yield: 25%, m.p. 143–145° C.
Elemental Analysis for C$_{25}$H$_{18}$F$_3$N$_3$O$_3$:

|  | C (%) | H (%) | N (%) |
|---|---|---|---|
| Calcd.: | 64.52; | 3.90; | 9.03 |
| Found: | 64.35; | 3.95; | 8.98 |

$^1$H-NMR(200 MHz,CDCl$_3$) δ: 3.80(3H,s), 5.01(2H,q), 5.74 (2H,s), 7.13(2H,d), 7.23(1H,t), 7.38–7.47(4H,m), 7.58–7.66 (2H,m), 7.72–7.78(2H,m)
IR(KBr) cm$^{-1}$: 2225, 1735, 1550, 1465, 1430, 1305, 1280, 1270, 1250, 1170, 1060, 770, 750, 745

Working Example 27

Ethyl 1-[(2'-cyanobiphenyl-4-yl)methyl]-2-ethoxybenzimidazole7-carboxylate

To a solution of ethyl 2-chloro-1-[(2'-cyanobiphenyl-4-yl)-methyl]benzimidazole-7-carboxylate (1.0 g) in ethanol (30 ml) was added NaOEt (0.17 g) and the mixture was heated under reflux for 1 hour. The reaction mixture was concentrated to dryness. The resultant residue was dissolved in ethyl acetate and the solution was washed with water, and then dried. After evaporation of the solvent, the residue was purified by column chromatography on silica gel to give the title compound as colorless crystals(0.37 g, 70%). $^1$H-NMR and IR spectra indicate that the product according to this working Example is completely identical with that obtained in Working Example 4.

Reference Example 14

2-(4-Formylphenyl)benzonitrile

A mixture of 2-(4-bromomethylphenyl)benzonitrile (12 g) and sodium bicarbonate (26 g) in dimethyl sulfoxide (150 ml) was heated at 120° C. for 5 hours with stirring. After addition of water, the mixture was extracted with ethyl acetate. The extract was washed with water, dried and concentrated to dryness. The residue was purified by column chromatography on silica gel to give crystals. Recrystallization from chloroform-isopropyl ether gave colorless needles (5.77 g, 63%).
$^1$H-NMR(200 MHz,CDCl$_3$) δ: 7.49–7.58(2H,m), 7.67–7.84 (4H,m), 8.00–8.05(2H,m), 10.10(1H,s)

Reference Example 15

2-(4-Aminomethylphenyl)benzonitrile

A mixture of 2-(4-bromomethylphenyl)benzonitrile (12 g) and potassium phtalimide (15 g) in DMF (200 ml) was stirred at 70° C. for 5 hours. After addition of water, the mixture was extracted with methylene chloride. The extract was washed with water, dried and concentrated to dryness to give crystals. Recrystallization from ethyl acetate-isopropyl ether gave colorless crystals. To a suspension of the crystals in methanol (500 ml) was added hydrazine hydrate (10 ml) and the mixture was refluxed for 12 hours. After evaporation of the solvent, the residue was dissolved in ethyl acetate and the solution was washed with 1N-NaOH and water. The organic layer was dried and concentrated to dryness to give crystals (14.2 g, 93%).
$^1$H-NMR(200 MHz,CDCl$_3$) δ: 1.56(2H,brs), 3.88(2H,s), 7.27–7.78(8H,m)

Working Example 28

Ethyl 2-ethoxy-1-[[2'-(1H-tetrazol-5-yl)biphenyl-4-yl]methyl]benzimidazole-7-carboxylate A mixture of ethyl 1-[(2'-cyanobiphenyl-4-yl)methyl]-2ethoxybenzimidazole-7-carboxylate (0.7 g) and trimethyltin azide (0.7 g) in toluene (15 ml) was heated under reflux for 4 days. The reaction mixture was concentrated to dryness and to the residue were added methanol (20 ml) and 1N-HCl (10 ml). The mixture was stirred at room temperature for 30 minutes and adjusted to pH 3 to 4 with 1N NaOH. After removal of the solvent, the residue was partitioned between chloroform and water. The organic layer was washed with water and dried, and the solvent was evaporated to dryness to give a syrup. The syrup was purified by column chromatography on silica gel to give crystals. Recrystallization from ethyl acetate-benzene afforded colorless crystals (0.35 g, 45%), m.p. 158–159° C.

Elemental Analysis for $C_{26}H_{24}N_6O_3$:

|  | C (%) | H (%) | N (%) |
|---|---|---|---|
| Calcd.: | 66.65; | 5.16; | 17.94 |
| Found: | 66.61; | 5.05; | 17.84 |

$^1$H-NMR(200 MHz,CDCl$_3$) δ: 1.09(3H,t), 1.43(3H,t), 4.02 (2H,q), 4.30(2H,q), 5.57(2H,s), 6.71(2H,d), 6.83–6.96(4H, m), 7.27–7.31(1H,m), 7.40(1H,dd), 7.55–7.66(2H,m), 8.04–8.09(1H,m)
IR(KBr) cm$^{-1}$: 1720, 1605, 1540, 1470, 1430, 1250, 1040, 750

Working Example 29

2-Ethoxy-1-[[2'-(1H-tetrazol-5-yl)biphenyl-4-yl] methyl]-benzimidazole-7-carboxylic acid A solution of ethyl 2-ethoxy-1-[[2'-(1H-tetrazol-5-yl) biphenyl-4-yl]methyl]benzimidazole-7-carboxylate (0.24 g) and 1N NaOH (1.5 ml) in ethanol (4 ml) was stirred at 80° C. for one hour. The reaction mixture was concentrated, and the concentrate was extracted with water and ethyl acetate. The aqueous layer was adjusted to pH 3–4 with 1N-HCl to give crystals. Recrystallization of the crystals from ethyl acetate-methanol afforded colorless crystals (0.15 g, 67%), m.p. 183–185° C.

Elemental Analysis for $C_{24}H_{20}N_6O_3 \cdot 1/5H_2O$:

|  | C (%) | H (%) | N (%) |
|---|---|---|---|
| Calcd.: | 64.91; | 4.63; | 18.93 |
| Found: | 65.04; | 4.51; | 18.77 |

$^1$H-NMR(200 MHz,DMSO-d$_6$) δ: 1.38(3H,t), 4.58(2H,q), 5.63(2H,s), 6.97(4H,q), 7.17(1H,t), 7.47–7.68(6H,m)
IR(KBr) cm$^{-1}$: 1710, 1550, 1480, 1430, 1280, 1240, 1040, 760

Working Example 30

Ethyl 2-pronoxy-1-[[2'-(1H-tetrazol-5-yl)biphenyl-4-yl]-methyl]benzimidazole-7-carboxylate A mixture of ethyl 1-[(2'-cyanobiphenyl-4-yl)methyl]-2-propoxybenzimidazole-7-carboxylate (0.69 g) and trimethyltin azide (0.7 g) in toluene (15 ml) was heated for 4 days under reflux. The reaction mixture was concentrated to dryness and to the mixture was added methanol (20 ml) and 1N-HCl (10 ml). After stirring at room temperature for 30 minutes, the mixture was adjusted to pH 3–4 with 1N NaOH. After removal of the solvent, the residue was extracted with chloroform-water. The organic layer was washed with water and dried, and the solvent was evaporated to dryness to give a syrup. The syrup was purified by column chromatography on silica gel to give crystals. Recrystallization from ethyl acetate-benzene afforded colorless crystals (0.31 g, 43%), m.p. 157–159° C.

Elemental Analysis for $C_{27}H_{26}N_6O_3$:

|  | C (%) | H (%) | N (%) |
|---|---|---|---|
| Calcd.: | 67.21; | 5.43; | 17.42 |
| Found: | 67.26; | 5.45; | 17.28 |

$^1$H-NMR(200 MHz,CDCl$_3$) δ: 1.03(3H,t), 1.13(3H,t), 1.75–1.92(2H,m), 4.05(2H,q), 4.23(2H,q), 5.57(2H,s), 6.75 (2H,d), 6.90(2H,d), 6.96(2H,d), 7.28–7.33(1H,m), 7.39–7.44(2H,m), 7.57–7.62(2H,m), 8.07–8.11 (1H,m)
IR(KBr) cm$^{-1}$: 1720, 1540, 1470, 1430, 1280, 1250, 1130, 1020, 750

Working Example 31

2-Propoxy-1-[[2'-(1H-tetrazol-5-yl)biphenyl-4-yl] methyl]-benzimidazole-7-carboxylic acid A solution of ethyl 2-propoxy-1-[[2'-(1H-tetrazol-5-yl)-biphenyl-4-yl]methyl]benzimidazole-7-carboxylate (0.23 g) in ethanol (4 ml) containing 1N-NaOH (1.5 ml) was heated at 80° C. for 2 hours. The reaction mixture was concentrated to dryness and the residue was extracted with water and ethyl acetate. The aqueous layer was adjusted to pH 3–4 with 1N-HCl to give crystals. Recrystallization from ethyl acetate-methanol afforded colorless crystals (0.15 g, 69%), m.p. 174–175° C.

Elemental Analysis for $C_{25}H_{22}N_6O_3 \cdot 0.3H_2O$:

|  | C (%) | H (%) | N (%) |
|---|---|---|---|
| Calcd.: | 65.29; | 4.95; | 18.27 |
| Found: | 65.41; | 4.92; | 18.20 |

$^1$H-NMR(200 MHz,DMSO-d$_6$) δ: 0.92(3H,t), 1.70–1.87 (2H,m), 4.47(2H,q), 5.63(2H,s), 6.96(4H,dd), 7.16(1H,t), 7.42–7.67(6H,m)
IR(KBr) cm$^{-1}$: 1700, 1550, 1430, 1290, 1240, 765

Working Example 32

Ethyl 2-mercapto-1-[[2'-(1H-tetrazol-5-yl)biphenyl-4-yl]-methyl]benzimidazole-7-carboxylate A mixture of ethyl [1-(2'-cyanobiphenyl-4-yl)methyl]-2-mercaptobenzimidazole-7-carboxylate (4.1 g) and trimethyltin azide (8.0 g) in toluene (100 ml) was heated for 4 days under reflux. The solvent was evaporated to dryness and the residue was stirred in a mixture of conc. hydrochloric acid (2 ml) and methanol (20 ml) at room temperature for 20 minutes. To the reaction mixture was added 1N-NaOH to adjust to about pH 4 and then the mixture was extracted with ethyl acetate. The organic layer was washed with water, dried, and concentrated to dryness to give crystals. Recrystallization from chloroform gave colorless crystals (5.0 g, 89%), m.p. 263–264° C. (decomp.).

Elemental Analysis for $C_{24}H_{20}N_6O_2S \cdot 1/2H_2O$:

|        | C (%) | H (%) | N (%) |
|--------|-------|-------|-------|
| Calcd.: | 61.92; | 4.55; | 18.05 |
| Found: | 61.99; | 4.30; | 17.86 |

¹H-NMR(200 MHz,DMSO-d₆) δ: 1.10(3H;t), 4.09(2H,q), 5.82(2H,br s), 6.87(2H,d), 7.00(2H,d), 7.26(1H,t), 7.37–7.69(6H,m)
IR(KBr) cm⁻¹: 1720, 1460, 1440, 1365, 1340, 1260, 1180, 1145, 1150, 1110, 990, 745

Working Example 33

Ethyl 2-methylthio-1-[[2'-(1H-tetrazol-5-yl) biphenyl-4-yl]-methyl]benzimidazole-7-carboxylate To a solution of ethyl 2-mercapto-1-[[2'-(1H-tetrazol-5-yl)biphenyl-4-yl]benzimidazole-7-carboxylate (0.68 g) in ethanol (10 ml) containing 1N-NaOH (3.0 ml) was added methyl iodide (0.24 g), and the mixture was stirred at room temperature for 2 hours. The reaction mixture was neutralized with dilute hydrochloric acid to give crystals. The crystals were purified by column chromatography on silica gel. Recrystallization from ethyl acetate afforded colorless prisms (0.31 g, 44%), m.p. 207–208° C. (decomp.).
Elemental Analysis for $C_{25}H_{22}N_6O_2S$:

|        | C (%) | H (%) | N (%) |
|--------|-------|-------|-------|
| Calcd.: | 63.81; | 4.71; | 17.86 |
| Found: | 63.55; | 4.81; | 17.50 |

¹-NMR(200 MHz,DMSO-d₆) δ: 1.13(3H,t), 2.77(3H,s), 4.14(2H,q), 5.62(2H,s), 6.84(2H,d), 7.26(1H,t), 7.46–7.70 (5H,m)
IR(KBR) cm⁻¹: 1705, 1480, 1450, 1420, 1360, 1340, 1275, 1255, 1190, 1140, 1100, 1025, 990, 770, 750

Working Example 34

Ethyl 2ethylthio-1-[[2'-(1H-tetrazol-5-yl)biphenyl-4-yl]methyl]benzimidazole-7-carboxylate To a solution of ethyl 2-mercapto-1-[[2'-(1H-tetrazol-5-yl)biphenyl-4-yl]methyl]benzimidazole-7-carboxylate (0.91 g) in ethanol (13 ml) containing 1N-NaOH (4 ml) was added ethyl iodide (0.34 g), and the mixture was stirred at room temperature for 4 hours. The reaction mixture was adjusted to pH 4 with dilute hydrochloric acid to give crystals. The crystals were collected by filtration and purified by column chromatography on silica gel. Recrystallization from ethyl acetate gave colorless prisms (0.55 g, 57%), m.p. 153–154° C. (decomp.).
Elemental Analysis for $C_{26}H_{24}N_6O_2S$:

|        | C (%) | H (%) | N (%) |
|--------|-------|-------|-------|
| Calcd.: | 64.44; | 4.99; | 17.34 |
| Found: | 64.37; | 5.05; | 17.20 |

¹H-NMR(200 MHz,,CDCl₃) δ: 1.19(3H,t), 1.37(3H,t), 3.20 (2H,q), 4.12(2H,q), 5.67(2H,s), 6.75(2H,d), 6.92(2H,d), 7.05(1H,t), 7.26–7.34(2H,m), 7.50(1H,dd), 7.53–7.63(2,m), 8.05–8.11(1H,m)
IR(KBr) cm⁻¹: 1715, 1450, 1420, 1365, 1345, 1280, 1195, 1145, 1110, 1035, 1015, 990, 760, 745

Working Example 35

Ethyl 2-propylthio-1-[[2'-(1H-tetrazol-5-yl) biphenyl-4-yl]methyl]benzimidazole-7-carboxylate Propyl iodide (0.37 g) was added to a solution of ethyl 2-mercapto-1-[[2'-(1H-tetrazol-5-yl)biphenyl-4-yl]methyl]-benzimidazole-7-carboxylate (0.91 g) in ethanol (13 ml) containing 1N NaOH (4.0 ml) and the mixture was stirred at room temperature for 5 hours. The reaction mixture was adjusted to about pH 4 with dilute hydrochloric acid to give crystals. The crystals were collected by filtration and purified by column chromatography on silica gel. Recrystallization from ethyl acetate-hexane gave colorless prisms (0.4 g, 40%), m.p. 177–178° C. (decomp.).
Elemental Analysis for $C_{27}H_{26}N_6O_2S$:

|        | C (%) | H (%) | N (%) |
|--------|-------|-------|-------|
| Calcd.: | 65.04; | 5.26; | 16.85 |
| Found: | 64.88; | 5.25; | 16.78 |

¹H-NMR(200 MHz,CDCl₃) δ: 1.04(3H,t), 1.19(3H,t), 1.76 (2H,m), 3.18(2H,t), 4.12(2H,q), 5.69(2H,s), 6.75(2H,d), 6.93(2H,d), 7.05(1H,t), 7.27–7.34(2H,m), 7.50(1H,dd), 7.54–7.63(2H,m), 8.07–8.12(1H,m)
IR(KBr) cm⁻¹: 1715, 1450, 1420, 1380, 1365, 1350, 1280, 1260, 1190, 1145, 1035, 1020, 990, 760, 745

Working Example 36

2-Methylthio-1-[[2'-(1H-tetrazol-5-yl)biphenyl-4-yl]-methyl]benzimidazole-7-carboxylic acid A solution of ethyl 2-methylthio-1-[[2'-(1H-tetrazol-5yl) biphenyl-4-yl]-methyl]benzimidazole-7-carboxylate (0.2 g) in a methanol (5 ml) solution containing 1N NaOH (1.3 ml) was heated under reflux for 2 hours. The reaction mixture was adjusted to about pH 4 with dilute hydrochloric acid to give crystals. The crystals were collected by filtration, and recrystallized from ethyl acetate-hexane to give colorless crystals (0.17 g, 81%), m.p. 223–225° C. (decomp.).
Elemental Analysis for $C_{23}H_{18}N_6O_2S \cdot 1/2 C_4H_8O_2$

|        | C (%) | H (%) | N (%) |
|--------|-------|-------|-------|
| Calcd.: | 61.72; | 4.56; | 17.27 |
| Found: | 61.59; | 4.54; | 17.54 |

¹H-NMR(200 MHz,DMSO-d₆) δ: 2.75(3H,s), 5.76(2H,r.), 6.88(2H,d), 7.01(2H,d), 7.25(1H,t), 7.47–7.66(5H,m), 7.82 (1H,d)
IR(KBR) cm⁻¹: 1710, 1485, 1450, 1420, 1370, 1345, 1320, 1280, 1245, 1195, 1150, 990, 780, 760

Working Example 37

2-Ethylthio-1-[[2'-(1H-tetrazol-5-yl)biphenyl-4-yl]-methyl]benzimidazole-7-carboxylic acid A solution of ethyl 2-ethylthio-1-[[2'-(1H-tetrazol-5-yl) biphenyl-4-yl]methyl]benzimidazole-7-carboxylate (0.35 g)

in a methanol (7 ml) solution containing 1N NaOH (2.2 ml) was heated under reflex for 2 hours. After evaporation of the solvent, the aqueous residue was adjusted to about pH 3–4 with 1N-HCl to give crystals. The crystals were collected by filtration. Recrystallization from ethyl acetate-methanol gave colorless crystals (0.21 g, 64%), m.p. 209–210° C. (decomp.).

Elemental Analysis for $C_{24}H_{20}N_6O_2S$:

|        | C (%)  | H (%) | N (%) |
|--------|--------|-------|-------|
| Calcd.:| 63.14; | 4.42; | 18.41 |
| Found: | 62.89; | 4.35; | 18.15 |

$^1$H-NMR(200 MHz,DMSO-$d_6$) δ: 1.39(3H,t), 3.36(2H,q), 5.76(2H,s), 6.87(2H,d), 7.01(2H,d), 7.25(1H,t), 7.47–7.69 (5H,m), 7.82(1H,dd)
IR(KBr) cm$^{-1}$: 1695, 1450, 1415, 1350, 1275, 1225, 1190, 1180, 1145, 755, 740

Working Example 38

2-Propylthio-1-[[2'-(1H-tetrazol-5-yl)biphenyl-4-yl]-methyl]benzimidazole-7-carboxylic acid A solution of ethyl 2-propylthio-1-[[2'-(1H-tetrazol-5-yl)biphenyl-4-yl]methyl]benzimidazole-7-carboxylate (0.25 g) in methanol (5 ml) containing 1N-NaOH (1.5 ml) was heated under reflux for 2 hours. After removal of the solvent, the aqueous residue was adjusted to about pH 3–4 with 1N-HCl to give crystals. The crystals were collected by filtration. Recrystallization from ethyl acetate-hexane gave colorless crystals (0.21 g, 91%), m.p. 222–223° C. (decomp.).

Elemental Analysis for $C_{25}H_{21}N_6O_2S$:

|        | C (%)  | H (%) | N (%) |
|--------|--------|-------|-------|
| Calcd.:| 63.95; | 4.51; | 17.90 |
| Found: | 63.78; | 4.85; | 17.59 |

$^1$H-NMR(200 MHz,DMSO-$d_6$) δ: 0.99(3H,t), 1.67–1.85 (2H,m), 3.35(2H,t), 5.77(2H,s), 6.87(2H,d), 7.01(2H,d), 7.25(1H,t), 7.46–7.70(5H,m), 7.82(1H,dd)
IR(KBr) cm$^{-1}$: 1700, 1450, 1280, 1240, 1195, 1145, 755, 740

Working Example 39

Methyl 2-ethoxy-1-[[2'-(1H-tetrazol-5-yl)biphenyl-4-yl]methyl]benzimidazole-7-carboxylate A mixture of methyl 1-[(2'-cyanobiphenyl-4-yl)methyl]-2-ethoxybenzimidazole-7-carboxylate (1.85 g) and trimethyltin azide (2.80 g) in toluene (15 ml) were heated under reflux for one day. The reaction mixture was concentrated to dryness. To the residue were added methanol (50 ml) and 1N-HCl (20 ml) and the mixture was stirred at room temperature for 30 minutes. The reaction mixture was adjusted to about pH 3–4 with 1N-NaOH. After removal of the solvent, the residual syrup was purified by column chromatography on silica gel to give crystals. Recrystallization from ethyl acetate-benzene gave colorless crystals (1.16 g, 56%), m.p. 191–193° C. (decomp.).

Elemental Analysis for $C_{25}H_{22}N_6O_3.1/5H_2O$:

|        | C (%)  | H (%) | N (%) |
|--------|--------|-------|-------|
| Calcd.:| 65.58; | 4.75; | 18.53 |
| Found: | 65.55; | 4.93; | 18.35 |

$^1$H-NMR(200 MHz,CDCl$_3$) δ: 1.43(3H,t,J=7.0 Hz)), 3.57 (3H,s), 4.30(2H,q,J=7.00 Hz), 5.54(2H,s), 6.72(2H,d,J=8.2), 6.84–6.97(4H,m), 7.28–7.33(1H,m), 7.40(1H,dd,J=1.8,7.0 Hz), 7.57–7.62(2H,m), 8.03–8.07(1H,m)
IR(KBr) cm$^{-1}$: 1720, 1550, 1475, 1430, 1280, 1250, 1040, 755, 735

Working Example 40

Ethyl 2-ethylamino-1-[[2'-(1H-tetrazol-5-yl)biphenyl-4-yl]methyl]benzimidazole-carboxylate A mixture of ethyl 1-[(2'-cyanobiphenyl-4-yl)methyl]-2-ethylaminobenzimidazole-7-carboxylate (1.23 g) and trimethyltin azide (2.80 g) in toluene (15 ml) was heated for 40 hours under reflux. Precipitates were collected by filtration and suspended in methanol (50 ml). To the suspension was added 1N-HCl (15 ml), and the mixture was stirred at room temperature for 10 minutes. The reaction mixture was adjusted to about pH 5 with 1N-NaOH, followed by extraction with chloroform. The organic layer was washed with water, dried and concentrated to dryness. The residue was purified by column chromatography on silica gel to give crystals. Recrystallization from methanol-ethyl acetate gave colorless crystals (0.83 g, 61%), m.p. 166–168° C.
$^1$H-NMR(200 MHz,CDCl$_3$) δ: 1.13(3H,t), 1.21(3H,t), 343 (2H,q), 4.13(2H,q), 5.48(2H,s), 6.78(2H,d), 6.99(2H,d), 7.07(1H,t), 7.22(1H,dd), 7.42–7.49(2H,m), 7.54–7.69(3H,m)
IR(KBr) cm$^{-1}$: 1720, 1650, 1310, 1285, 765, 755, 750

Working Example 41

Ethyl 2-propylamino-1-[[2'-(1H-tetrazol-5-yl)biphenyl-4-yl]methyl]benzimidazole-7-carboxylate A solution of ethyl 1-[(2'-cyanobiphenyl-4-yl)methyl]-2-propylaminobenzimidazole-7-carboxylate (1.20 g) and trimethyltin azide (2.7 g) in toluene (15 ml) was heated for 50 hours under reflux. Precipitates were collected by filtration and suspended in methanol (20 ml). After addition of 1N-HCl (15 ml), the reaction mixture was stirred at room temperature for 10 minutes. The mixture was adjusted to about pH 5 with 1N-NaOH, followed by extraction with chloroform. The organic layer was washed with water, dried and concentrated to dryness. The concentrate was purified by column chromatography on silica gel to give crystals. Recrystallization from methanol-ethyl acetate gave colorless crystals (10 g, 77%), m.p. 170–172° C.
$^1$H-NMR(200 MHz,CDCl$_3$) δ: 0.89(3H,t), 1.14(3H,t), 1.52–1.70(2H,m), 3.35(2H,t), 4.14(2H,q), 5.49(2H,s), 6.77 (2H,d), 6.99(2H,d), 7.05(1H,t), 7.21(1H,dd), 7.39–7.47(2H,m), 7.50–7.65(3H,m)
IR(KBr) cm$^{-1}$: 1720, 1670, 1660, 1290, 1270, 760

Working Example 42

2-Ethoxy-1-[[2'-(N-triphenylmethyltetrazol-5-yl)-biphenyl-4-yl]methyl]benzimidazole-7-carboxylic acid To a solution of 2-ethoxy-[[2'-(1H-tetrazol-5-yl)biphenyl-4-yl]methyl]benzimidazole-7-carboxylic acid (2.07 g) in methylene chloride (10 ml) were added trityl chloride (1.59 g) and triethylamine (0.8 ml). The mixture was stirred at room temperature for one hour. The reaction mixture was washed with water, dried and concentrated to dryness. The residue was purified by column chromatography on silica gel to give crystals. Recrystallization of crude crystals thus obtained from ethyl acetate-benzene gave colorless crystals (2.12 g, 66%), m.p. 168–170° C.

Elemental Analysis for $C_{43}H_{34}N_6O_3$:

|  | C (%) | H (%) | N (%) |
|---|---|---|---|
| Calcd.: | 75.64; | 5.02; | 12.31 |
| Found: | 75.37; | 4.96; | 12.20 |

$^1$H-NMR(200 MHz,CDCl$_3$) δ: 1.40(3H,t), 4.61(2H,q), 5.58 (2H,s), 6.76(2H,d), 6.91–6.96(8H,m), 7.12(1H,t), 7.17–7.41 (12H,m), 7.60(1H,dd), 7.73–7.82(2H,m)

Working Example 43

Pivaloyloxymethyl 2-ethoxy-1-[[2'-(1H-tetrazol-5-yl)-biphenyl-4-yl]benzimidazole-7-carboxylate To a solution of 2-ethoxy-1-[[2'-(N-triphenylmethyltetrazol-5-yl)biphenyl-4-yl]methyl]benzimidazole-7-carboxylic acid (2.2 g) in DMF (10 ml) were added potassium carbonate (0.53 g) and pivaloyloxymethyl iodide (0.94 g), and the mixture was stirred for 30 minutes at room temperature. To the reaction mixture was added water and the mixture was extracted with ethyl acetate. The organic layer was washed with water and dried. After removal of the solvent, the residue was dissolved in methanol (30 ml) and 1N-HCl (6 ml). The mixture was stirred for one hour at room temperature. The reaction mixture was concentrated to dryness and the residue was partitioned between water and ethyl acetate. The organic layer was washed with water and dried. After removal of the solvent, the residue was purified by column chromatography on silica gel to give crystals. The crystals were recrystallized from ethyl acetate-hexane to give colorless crystals (1.13 g, 63%), m.p. 104–106° C.

Elemental Analysis for $C_{30}H_{30}N_6O_5 \cdot 1/5C_4H_8O_2 \cdot 1/5C_6H_{14}$:

|  | C (%) | H (%) | N (%) |
|---|---|---|---|
| Calcd.: | 65.06; | 5.90; | 14.32 |
| Found: | 64.79; | 5.85; | 14.43 |

$^1$H-NMR(200 MHz,CDCl$_3$) δ: 1.13(9H,s), 1.44(3H,t), 4.37 (2H,q), 5.61(2H,s), 5.68(2H,s), 6.80(2H,d), 6.93(2H,d), 6.99–7.11(2H,m), 7.33–7.37(1H,m), 7.49–7.54(1H,m), 7.59–7.62(2H,m), 8.03–8.07(1H,m)

Working Example 44

1-(Cyclohexyloxycarbonyloxy)ethyl 2-ethoxy-1-[[2'-(1H-tetrazol-5-yl)biphenyl-4-yl]methyl]benzimidazole-7-carboxylate To a solution of 2-ethoxy-1-[[2'-(N-triphenylmethyltetrazol-5-yl)biphenyl-4-yl]methyl]benzimidazole-7-carboxylic acid (0.5 g) in DMF (5 ml) were added potassium carbonate (0.12 g) and cyclohexyl 1-iodoethyl carbonate (0.26 g). The mixture was stirred for one hour at room temperature. To the reaction mixture was added water and the mixture was extracted with ethyl acetate. The organic layer was washed with water and dried. After removal of the solvent, the residue was dissolved in methanol (10 ml) and to the solution was added 1N-HCl (2 ml). The mixture was stirred for one hour at room temperature. The reaction mixture was concentrated to dryness and the residue was partitioned between ethyl acetate and water. The organic layer was washed with water and dried. After removal of the solvent, the residue was purified by column chromatography on silica gel to give colorless powder (0.21 g, 47%), m.p. 103–106° C.

Elemental Analysis for $C_{33}N_{34}N_6O_6$:

|  | C (%) | H (%) | N (%) |
|---|---|---|---|
| Calcd.: | 64.91; | 5.61; | 13.76 |
| Found: | 64.94; | 5.71; | 13.66 |

To the powder (1 g) obtained as above was added ethanol (6 ml). The mixture was stirred for 3 hours at room temperature and allowed to stand under ice-cooling. The mixture was then stirred for one hour at temperatures not higher than 10° C. Resultant crystals were collected by filtration and washed with cold ethanol. The crystals were dried at 25° C. for 9 hours under reduced pressure, then at 35° C. for further 18 hours to obtain white powdery crystals (0.94 g), m.p. 158–166° C. (decomp.).

Elemental Analysis for $C_{32}H_{34}N_6O_6$:

|  | C (%) | H (%) | N (%) |
|---|---|---|---|
| Calcd.: | 64.91; | 5.61; | 13.76 |
| Found: | 64.73; | 5.66; | 13.64 |

$^1$H-NMR (200 MHz) δ: 1.13–1.84(16H,m), 4.28–4.55(3H, m), 5.65(2H,d), 6.72(1H,q), 6.81(2H,d), 6.93(2H,d), 7.03 (1H,t), 7.22–7.23(1H,m), 7.31–7.36(1H,m), 7.52–7.60(3H, m), 8.02–8.07(1H,m)

IR(KBR) cm$^{-1}$: 2942, 1754, 1717, 1549, 1476, 1431, 1076, 1034, 750

MS(m/z) : 611 [M+H]$^+$

Working Example 45

Methyl 2-methoxy-1-[[2'-(1H-tetrazol-5-yl-4-yl]methyl]benzimidazole-7-carboxylate Methyl [1-(2'-cyanobiphenyl-4-yl)methyl]-2-methoxybenzimidazole-7-carboxylate (0.60 g) and trimethyltin azide (1.5 g) in toluene (15 ml) were heated for 40 hours under reflux. Precipitated crystals were dissolved in methanol (10 ml) and to the solution was added 1N-HCL (3 ml). The mixture was stirred for 10 minutes at room temperature and the methanol was evaporated. The aqueous residue was adjusted to pH 3–4 with 1N-NaOH, followed by extraction with ethyl acetate. The organic layer was washed with water and dried. After removal of the solvent, the residue was purified by column chromatography on silica gel to give crystals. The crystals were recrystallized from ethyl acetate to give colorless prisms (0.65 g, 65%), m.p. 165–166° C.

Elemental Analysis for $C_{24}H_{20}N_6O_3 \cdot 1/10H_2O$:

|  | C (%) | H (%) | N (%) |
|---|---|---|---|
| Calcd.: | 65.18; | 4.60; | 19.00 |
| Found: | 64.91; | 4.49; | 18.99 |

$^1$H-NMR(200 MHz,CDCl$_3$) δ: 3.64(3H,s), 3.93(3H,s), 5.55 (2H,s), 6.75(2H,d), 6.90–7.01(4H,m), 7.31–7.36(1H,m), 7.49(1H,dd), 7.55–7.64(2H,m), 8.03–8.07(1H,m)

Working Example 46

2-Methoxy-1-[[2'-(1H-tetrazol-5-yl)biphenyl-4-yl]-methyl]benzimidazole-7-carboxylic acid To a solution of methyl 2-methoxy-1-[[2'-(1H-tetrazol-5-yl)-biphenyl-4-yl]methyl]benzimidazole-7-carboxylate (0.22 g) in methanol (10 ml) was added 1N-NaOH (1.5 ml). The mixture was heated for 6 hours under reflux. The reaction mixture was concentrated to dryness and to the residue was added water. The mixture was adjusted to pH 3–4 with 1N-HCl to give crystals. Recrystallization from methanol-chloroform gave colorless needles (0.17 g, 77%), m.p. 208–209° C.

Elemental Analysis for $C_{23}H_{18}N_6O_3 \cdot 0.7H_2O$:

|  | C (%) | H (%) | N (%) |
|---|---|---|---|
| Calcd.: | 62.92; | 4.45; | 19.14 |
| Found: | 62.81; | 4.08; | 19.19 |

$^1$H-NMR(200 MHZ,DMSO-d$_6$) δ: 4.15(3H,s), 5.63(2H,s), 6.90(2H,d), 7.00(2H,d), 7.18(1H,t), 7.46–7.70(6H,m)

Working Example 47

2-Ethylamino-1-[[2'-(1H-tetrazol-5-yl)biphenyl-4-yl]methyl]-benzimidazole-7-carboxylic acid To a solution of ethyl 2-ethylamino-1-[[2'-(1H-tetrazol-5yl)biphenyl-4-yl]benzimidazole-7-carboxylate (0.52 g) in ethanol (5 ml) was added 1N-NaOH (4 ml), and the mixture was stirred for 2 hours at 80° C. The reaction mixture was concentrated to dryness and the aqueous residue was adjusted to pH 4–5 with 1N-HCl to give crystals. The crystals were collected by filtration and recrystallized from methanol-chloroform to give colorless crystals (0.3 g, 63.4%), m.p. 240–242° C.

Elemental Analysis for $C_{24}H_{21}N_7O_2 \cdot 1.1H_2O$:

|  | C (%) | H (%) | N (%) |
|---|---|---|---|
| Calcd.: | 62.76; | 5.09; | 21.35 |
| Found: | 62.65; | 5.15; | 21.23 |

$^1$H-NMR(200 MHz,DMSO-d$_6$) δ: 1.20(3H,t), 3.43(2H,q), 5.62(2H,s), 6.85(2H,d), 6.99(2H,d), 7.10(1H,t), 7.34(1H,d), 7.44–7.68(5H,m)

Working Example 48

2-Propylamino-1-[[2'-(1H-tetrazol-5-yl)biphenyl-4-yl]methyl]benzimidazole-7-carboxylic acid In substantially the same manner as Working Example 47, the above compound was obtained in a yield of 73%, m.p. 244–246° C.

Elemental Analysis for $C_{25}H_{23}N_7O_2 \cdot 1/2H_2O$:

|  | C (%) | H (%) | N (%) |
|---|---|---|---|
| Calcd.: | 64.92; | 5.23; | 21.20 |
| Found: | 64.79; | 5.27; | 21.08 |

In substantially the same manner as Working Example 43, the following compounds (Working Examples 49–53) were synthesized.

Working Example 49

(5-Methyl-2-oxo-1,3-dioxolen-4-yl)methyl 2-ethoxy-1-[[2'-(1H-tetrazol-5-yl)biphenyl-4-yl]methyl]benzimidazole-7-carboxylate Yield: 55%, m.p.: 122–125° C. (decomp.)

Elemental Analysis for $C_{22}H_{24}N_6O_6 \cdot CHCl_3$:

|  | C (%) | H (%) | N (%) |
|---|---|---|---|
| Calcd.: | 53.63; | 3.75; | 12.51 |
| Found: | 53.32; | 3.58; | 12.24 |

$^1$H-NMR(200 MHz,CDCl$_3$) δ: 1.43(3H,t), 2.11(3H,s), 4.40 (2H,q), 4.80(2H,s), 5.58(2H,s), 6.79(2H,d), 6.94(2H,d), 7.02 (1H,t), 7.15(1H,dd), 7.35–7.39(1H,m), 7.49–7.63(3H,m), 8.00–8.04(1H,m)

Working Example 50

Acetoxymethyl 2-ethoxy-1-[[2'-(1H-tetrazol-5-yl) biphenyl-4-yl]methyl]benzimidazole-7-carboxylate Yield: 38%, m.p.: 152–154° C. (decomp.)

Elemental Analysis for $C_{27}H_{24}N_6O_5$:

|  | C (%) | H (%) | N (%) |
|---|---|---|---|
| Calcd.: | 63.27; | 4.72; | 16.40 |
| Found: | 63.55; | 4.70; | 16.18 |

$^1$H-NMR(200 MHz,CDCl$_3$) δ: 1.43(3H,t), 2.01(3H,s), 4.33 (2H,q), 5.61(2H,s), 5.69(2H,s), 6.81(2H,d), 6.93(2H,d), 7.01 (tH,t), 7.13(1H,d), 7.33–7.38(1H,m), 7.53–7.62(3H,m), 8.03–8.07(1H,m)

Working Example 51

Propionyloxymethyl 2-ethoxy-1-[[2'-(1H-tetrazol-5-yl)-biphenyl-4-yl]methyl]benzimidazole-7-carboxylate Yield: 60%, m.p.: 145–150° C. (decomp.)

Elemental Analysis for $C_{28}H_{26}N_6O_5 \cdot 0.2C_7H_8$:

|  | C (%) | H (%) | N (%) |
|---|---|---|---|
| Calcd.: | 64.79; | 5.10; | 15.42 |
| Found: | 64.70; | 5.10; | 15.44 |

$^1$H-NMR(200 MHz,CDCl$_3$) δ: 1.04(3H,t), 1.44(3H,t), 2.29 (2H,q), 4.40(2H,q), 5.61(2H,s), 5.71(2H,s), 6.82(2H,d), 6.92–7.14(3H,m), 7.20(1H,m), 7.33–7.38(1H,m), 7.53–7.61 (3H,m), 8.03–8.08(1H,m)

Working Example 52

Butyryloxymethyl 2-ethoxy-1-[[2'-(1H-tetrazol-5-yl)biphenyl-4-yl]methyl]benzimidazole-7-carboxylate Yield: 36%, m.p.: 96–100° C.
Elemental Analysis for $C_{28}H_{28}N_6O_5 \cdot 0.4C_7H_8$:

|  | C (%) | H (%) | N (%) |
|---|---|---|---|
| Calcd.: | 66.15; | 5.45; | 14.55 |
| Found: | 66.11; | 5.44; | 14.65 |

$^1$H-NMR(200 MHz,CDCl$_3$) δ: 0.85(3H,t), 1.44(3H,t), 1.55 (2H,m), 2.24(2H,q), 4.38(2H,q), 5.61(2H,s), 5.70(2H,s), 6.81(2H,d), 6.93(2H,d), 7.00(1H,t), 7.20(1H,m), 7.33–7.38 (1H,m), 7.52–7.61(3H,m), 8.01–8.10(1H,m)

Working Example 53

Isobutyryloxymethyl 2-ethoxy-1-[[2'-(1H-tetrazol-5-yl)biphenyl-4-yl]methyl]benzimidazole-7-carboxylate Yield: 53%, m.p.: 143–145° C.
Elemental Analysis for $C_{28}H_{28}N_6O_5 \cdot 0.1C_7H_8$:

|  | C (%) | H (%) | N (%) |
|---|---|---|---|
| Calcd.: | 64.88; | 5.28; | 15.29 |
| Found: | 65.04; | 5.25; | 15.18 |

$^1$H-NMR(200 MHz, CDCl$_3$) δ: 1.09(6H,d), 1.44(3H,t), 2.50 (1H,m), 4.38(2H,q), 5.61(2H,s), 5.70(2H,s), 6.81(2H,d), 6.91–7.00(3H,m), 7.19(1H,m), 7.33–7.37(1H,m), 7.51–7.63 (3H,m), 8.02–8.07(1H,m)

In substantially the same manner as Working Example 44, the following compounds (Working Examples 54–56) were synthesized.

Working Example 54

1-(Ethoxycarbonyloxy)ethyl 2-ethoxy-1-[[2'-(1H-tetrazol-5-yl)-biphenyl-4-yl]methyl]benzimidazole-7-carboxylate Yield: 44%, m.p.: 85–87° C.
Elemental Analysis for $C_{29}H_{28}N_6O_6 \cdot 0.3H_2$):

|  | C (%) | H (%) | N (%) |
|---|---|---|---|
| Calcd.: | 61.98; | 5.13; | 14.95 |
| Found: | 62.11; | 5.02; | 14.69 |

$^1$H-NMR(200 MHz,CDCl$_3$) δ: 1.20(3H,t), 1.30(3H,d), 1.41 (3H,t), 4.03–4.22(3H,m), 4.31–4.47(1H,m), 5.61(2H,s), 6.62–6.72(3H,m), 6.80–6.95(4H,m), 7.29–7.32(1H,m), 7.47 (1H,dd), 7.54–7.64(2H,m), 7.97–8.01 (1H,m)

Working Example 55

1-Acetoxyethyl 2-ethoxy-1-[[2'-1-(1H-tetrazol-5-yl)biphenyl-4-yl]methyl]benzimidazole-7-carboxylate Yield: 31%, m.p.: 105–107° C.
Elemental Analysis for $C_{28}H_{26}N_6O_5 \cdot 0.5H_2O$:

|  | C (%) | H (%) | N (%) |
|---|---|---|---|
| Calcd.: | 62.80; | 5.08; | 15.69 |
| Found: | 62.77; | 4.69; | 15.85 |

$^1$H-NMR(200 MHz,CDCl$_3$) δ: 1.46(3H,t), 1.49(3H,d), 4.47–4.62 (2H,m), 5.59(1H,d), 5.83(1H,d), 6.84(1H,q), 6.90 (2H,d), 7.03(2H,d), 7.11(1H,t), 7.34–7.39(1H,m), 7.49(1H, d), 7.53–7.61(3H,m), 8.07–8.11(1H,m)

Working Example 56

1-(Isopropoxycarbonyloxy)ethyl 2-ethoxy-1-[[2'-(1H-tetrazol-5-yl)biphenyl-4-yl]methyl]benzimidazole-7-carboxylate Yield: 33%, m.p.: 74–76° C.
Elemental Analysis for $C_{30}H_{30}N_6O_5 \cdot 1.5H_2O$:

|  | C (%) | H (%) | N (%) |
|---|---|---|---|
| Calcd.: | 61.95; | 5.72; | 14.45 |
| Found: | 62.02; | 5.43; | 14.20 |

$^1$H-NMR(200 MHz,CDCl$_3$) δ: 1.20(3H,d), 1.21(3H,d), 1.30 (3H,d), 1.42(3H,t), 4.08–4.24(1H,m), 4.34–4.50(1H,m), 4.79(1H,m), 5.61(2H,s), 6.62–6.75(3H,m), 7.27–7.32(1H, m), 7.48(1H,dd), 7.54–7.64(2H,m), 7.98–8.03(1H,m)

Working Example 57

2-Methylamino-1-[[2'-(1H-tetrazol-5-yl)biphenyl-4-yl]methyl]-benzimidazole-7-carboxylic acid The above compound was synthesized by substantially the same manner as Working Examples 40 and 47.

Yield: 40%, m.p.: 247–250° C. (decomp.)
Elemental Analysis for $C_{23}H_{19}N_7O_2 \cdot 2.0H_2O$:

|  | C (%) | H (%) | N (%) |
|---|---|---|---|
| Calcd.: | 59.86; | 5.02; | 21.25 |
| Found: | 59.99; | 4.89; | 21.36 |

$^1$H-NMR(200 MHz,CDCl$_3$) δ: 2.94(3H,s), 5.64(2H,s), 6.82 (2H,d), 6.99(2H,d), 7.02(1H,t), 7.31(1H,d), 7.42–7.63(5H, m)

In substantially the same manner as Working Example 43, the following compounds (Working Examples 58–60) were synthesized.

Working Example 58

Cyclohexylcarbonyloxymethyl 2-ethoxy-1-[[2'-(1H-tetrazol-5-yl)biphenyl-4-yl]methyl]benzimidazole-7-carboxylate Yield: 54%, m.p.: 140–142° C.
Elemental Analysis for $C_{32}H_{32}N_6O_5$:

|        | C (%)  | H (%) | N (%) |
|--------|--------|-------|-------|
| Calcd.: | 66.19; | 5.55; | 14.47 |
| Found:  | 65.93; | 5.46; | 14.39 |

$^1$H-NMR(200 MHz,CDCl$_3$) δ: 1.21–1.87(13H,m), 2.20–2.32(1H,m), 4.47(2H,q), 5.60(2H,s), 5.73(2H,s), 6.86 (2H,d), 7.07(1H,t), 7.27–7.40(3H,m), 7.54–7.61(2H,m), 8.05–8.09(1H,m)

Working Example 59

Benzoyloxymethyl 2-ethoxy-1-[[2'-1H-tetrazol-5-yl) biphenyl-4yl]methyl]benzimidazole-7-carboxylate Yield: 47%, m.p.: 138–142° C.

Elemental Analysis for C$_{32}$H$_{26}$N$_6$O$_5$.0.5H$_2$O.0.1C$_4$H$_8$O$_2$:

|        | C (%)  | H (%) | N (%) |
|--------|--------|-------|-------|
| Calcd.: | 65.67; | 4.76; | 14.18 |
| Found:  | 65.71; | 4.66; | 13.96 |

$^1$H-NMR(200 MHz,CDCl$_3$) δ: 1.43(3H,t), 4.36(2H,q), 5.60 (2H,s), 5.98(2H,s), 6.74(4H,s), 6.99(1H,t), 7.09–7.14(1H, m), 7.21–7.36(3H,m), 7.50–7.59(4H,m), 7.90(2H,d), 8.02–8.06(1H,m)

Working Example 60

(E)-cinnamoyloxymethyl 2-ethoxy-1-[[2'-(1H-tetrazol-5-yl)biphenyl-4-yl]methyl]benzimidazole-7-carboxylate Yield: 56%, m.p.: 146–147° C.

Elemental Analysis for C$_{34}$H$_{28}$N$_6$O$_5$.0.4C$_8$H$_8$O$_2$:

|        | C (%)  | H (%) | N (%) |
|--------|--------|-------|-------|
| Calcd.: | 67.16; | 5.07; | 13.20 |
| Found:  | 66.97; | 4.86; | 13.28 |

$^1$H-NMR(200 MHz,CDCl$_3$) δ: 1.44(3H,t), 4.45(2H,q), 5.61 (2H,s), 5.87(2H,s), 6.33(1H,d), 6.84(2H,d), 6.96(2H,d), 7.05 (1H,t) 7.31–7.57(10H,m), 7.65(1H,d), 8.00–8.04(1H,m)

In substantially the same manner as Working Examples 43 and 44, the following compounds (Working Examples 61–63) were synthesized.

Working Example 61

Cyclopentylcarbonyloxymethyl 2-ethoxy-1-[[2'-(1 H-tetrazol-5-yl)biphenyl-4-yl]methyl] benzimidazole-7-carboxylate Yield: 54%, m.p.: 136–138° C.

Elemental Analysis for C$_{31}$H$_{30}$N$_6$O$_5$:

|        | C (%)  | H (%) | N (%) |
|--------|--------|-------|-------|
| Calcd.: | 65.71; | 5.34; | 14.83 |
| Found:  | 65.59; | 5.33; | 14.67 |

$^1$H-NMR(200 MHz,CDCl$_3$) δ: 1.41–1.84(11H,m), 2.61–2.76(1H,m), 4.43(2H,q), 5.61(2H,s), 5.72(2H,s), 6.84 (2H,d), 6.96(2H,d), 7.05(1H,t), 7.22–7.26(1H,m), 7.35–7.39 (1H,m), 7.53–7.61(3H,m), 8.03–8.08(1H,m)

Working Example 62

Pivaloyloxymethyl 2-ethylamino-1-[[2'-(1H-tetrazol-5-yl)biphenyl-4-yl]methyl]benzimidazole-7-carboxylate Yield: 59%, m.p.: 130–135° C.

Elemental Analysis for C$_{30}$H$_{31}$N$_7$O$_4$.0.4CHCl$_3$.02H$_2$O:

|        | C (%)  | H (%) | N (%) |
|--------|--------|-------|-------|
| Calcd.: | 60.36; | 5.30; | 16.21 |
| Found:  | 60.20; | 5.20; | 16.08 |

$^1$-NMR(200 MHz,CDCl$_3$) δ: 1.12(9H,s), 1.20(3H,t), 3.43 (2H,q), 5.52(2H,s), 5.81(2H,s), 6.80(2H,d), 6.99(2H,d), 7.08 (1H,t), 7.24(1H,dd), 7.43–7.68(5H,m)

Working Example 63

1-(Cyclohexyloxycarbonyloxy)ethyl 2-ethylamino-1-[[2'-(1H-tetrazol-5-yl)biphenyl-4-yl]methyl] benzimidazole-7-carboxylate Yield: 76%, m.p.: 149–152° C.

Elemental Analysis for C$_{33}$H$_{35}$N$_7$O$_5$.0.5H$_2$O:

|        | C (%)  | H (%) | N (%) |
|--------|--------|-------|-------|
| Calcd.: | 64.06; | 5.86; | 15.85 |
| Found:  | 64.27; | 6.02; | 15.86 |

$^1$H-NMR(200 MHz,CDCl$_3$) δ: 1.12–1.88(16H,m), 3.38–3.47(2H,m), 4.48–4.59(1H,m), 5.51(2H,s), 6.75–6.88 (5H,m), 7.04(1H,t), 7.29–7.40(2H,m), 7.47–7.51(3H,m), 7.91–7.95(1H,m)

Working Example 64

Methyl 2-allyloxy-1-[[2'-(1H-tetrazol-5-yl)biphenyl-4-yl]-methyl]benzimidazole-7-carboxylate The title compound was prepared as colorless crystals from methyl 2-allyloxy-1- [[2'-cyanobiphenyl-4-yl)methyl] benzimidazole-7-carboxylate according to the procedure for Working Example 28.

Yield: 30%, m.p.: 154–156° C.

Elemental Analysis for $C_{26}H_{22}N_6O_3 \cdot 0.5H_2O$:

|        | C (%)  | H (%) | N (%) |
|--------|--------|-------|-------|
| Calcd.:| 65.67; | 4.88; | 17.67 |
| Found: | 65.63; | 4.71; | 17.68 |

$^1$H-NMR(200 MHz,CDCl$_3$) δ: 3.75(3H,d), 4.58–4.61(1H,m), 4.92–4.95(1H,m), 5.18–5.48(2H,m), 5.52(2H,d), 5.83–6.15(1H,m), 6.98–7.05(2H,m), 7.09–7.17(2H,m), 7.35–7.44(2H,m), 7.47–7.60(3H,m), 8.09–8.19(1H,m)
IR(KBr) cm$^{-1}$: 1720, 1670, 1550, 1470, 1430, 1260, 1250, 1025, 760, 735

Working Example 65

Methyl 2-butoxy-1-[[2'-(1H-tetrazol-5-yl)biphenyl-4-yl]-methyl]benzimidazole-7-carboxylate The title compound was prepared as colorless needles from methyl 2-butoxy-1-[(2'-cyanobiphenyl-4-yl)methyl]benzimidazole-7-carboxylate according to the procedure for Working Example 28.
Yield: 91%, m.p.: 146–148° C.
Elemental Analysis for $C_{27}H_{26}N_6O_3O$:

|        | C (%)  | H (%) | N (%) |
|--------|--------|-------|-------|
| Calcd.:| 67.21; | 5.43; | 17.42 |
| Found: | 67.00; | 5.45; | 17.49 |

$^1$H-NMR(200 HHz,CDCl$_3$) δ: 0.99(3H,t), 1.37–1.55(2H,m), 1.74–1.88(2H,m), 3.61(3H,s), 4.27(2H,t), 5.53(2H,s), 6.75(2H,d), 6.90(2H,d), 6.97(2H,d), 7.30–7.34(1H,m), 7.41(2H,dd), 7.57–7.61(2H,m), 8.04–8.09(1H,m)
IR(KBr) cm$^{-1}$: 1720, 1600, 1540, 1470, 1430, 1270, 1250, 1020, 750

Working Example 66

Methyl 2-butylamino-1-[[2'-(1H-tetrazol-5-yl)biphenyl-4-yl]-methyl]benzimidazole-7-carboxylate The title compound was prepared as colorless crystals from methyl 2-butylamino-1-[(2'-cyanobiphenyl-4-yl)methyl]benzimidazole-7-carboxylate according to the procedure for Working Example 41.
Yield: 42%, m.p.: 216–218° C.
Elemental Analysis for $C_{27}H_{27}N_7O_2 \cdot H_2O$:

|        | C (%)  | H (%) | N (%) |
|--------|--------|-------|-------|
| Calcd.:| 64.91; | 5.85; | 19.63 |
| Found: | 64.86; | 5.68; | 19.41 |

$^1$H-NMR (200 MHz, DMSO-d$_6$) δ: 0.91(3H,t), 1.25–1.43(2H,m), 1.52–1.67(2H,m), 3.65(3H,s), 5.47(2H,s), 6.79(2H,d), 6.98–7.05(3H,m), 7.18(1H,dd), 7.42–7.64(5H,m)
IR(KBr) cm$^{-1}$: 1720, 1665, 1660, 1650, 1430, 1260, 745

Working Example 67

Methyl 1-[[2'-(1H-tetrazol-5-yl)biphenyl-4-yl]methyl]-2morpholinobenzimidazole-7-carboxylate The title compound was prepared as colorless crystals from methyl 1-[(2'-cyanobiphenyl-4-yl)methyl]-2-morpholinobenzimidazole-7-carboxylate according to the procedure for Working Example 41.
Yield: 62%, m.p.: 163–167° C.
Elemental Analysis for $C_{27}H_{25}N_7O_3 \cdot O6CHCl_3$:

|        | C (%)  | H (%) | N (%) |
|--------|--------|-------|-------|
| Calcd.:| 58.45; | 4.55; | 17.29 |
| Found: | 58.66; | 4.36; | 17.54 |

$^1$H-NMR(200 MHz,CDCl$_3$) δ: 3.33(4H,t), 3.73(3H,s), 3.90(4H,t), 5.44(2H,s), 6.62(2H,d), 6.97(2H,d), 7.17(1H,t), 7.33–7.38(1H,m), 7.43–7.50(2H,m), 7.55–7.61(2H,m), 8.08–8.13(1H,m)
IR(KBr) cm$^{-1}$: 1730, 1600, 1530, 1455, 1420, 1405, 1280, 1260, 1120, 1110, 1000, 760, 750, 740

Working Example 68

Methyl 1-[[2'-(1H-tetrazol-5-yl)biphenyl-4-yl)]methyl]-2-piperidinobenzimidazole-7-carboxylate The title compound was prepared as colorless crystals from methyl 1-[[2'-cyanobiphenyl-4-yl)methyl]-2-piperidinobenzimidazole-7carboxylate according to the procedure for Working Example 41.
Yield: 47%, m.p.: 146–150° C.
Elemental Analysis for $C_{28}H_{27}N_7O_2 \cdot 0.8CHCl_3$:

|        | C (%)  | H (%) | N (%) |
|--------|--------|-------|-------|
| Calcd.:| 58.72; | 4.76; | 16.64 |
| Found: | 58.69; | 4.66; | 16.75 |

$^1$H-NMR(200 MHz,CDCl$_3$) δ: 1.72(6H,brs), 3.11(4H,m), 3.61(3H,s), 5.38(2H,s), 6.45(2H,d), 6.80(2H,d), 6.89–6.96(2H,m), 7.28–7.37(2H,m), 7.56–7.64(2H,m), 8.01–8.06(1H,m)
IR(KBr) cm$^{-1}$: 1715, 1600, 1530, 1450, 1420, 1415, 1405, 1300, 1280, 1260, 1240, 1215, 1130, 770, 760, 750

Working Example 69

Methyl 2-ethylmethylamino-1-[[2'-(1H-tetrazol-5-yl)biphenyl-4-yl]methyl]benzimidazole-7-carboxylate The title compound was prepared as colorless crystals from methyl 2-ethylmethylamino-1-[(2'-cyanobiphenyl-4-yl]-methyl]benzimidazole-7-carboxylate according to the procedure for Working Example 41.
Yield: 54%, m.p.: 130–136° C. (decomp.).
Elemental Analysis for $C_{28}H_{25}N_7O_2 \cdot 0.6H_2O$:

|        | C (%)  | H (%) | N (%) |
|--------|--------|-------|-------|
| Calcd.:| 59.26; | 4.79; | 18.19 |
| Found: | 59.04; | 4.95; | 18.05 |

$^1$H-NMR(200 MHz,CDCl$_3$) δ: 1.19(3H,t), 2.57(3H,s), 3.22(2H,m), 3.62(3H,s), 5.40(2H,s), 6.43(2H,d), 6.78–6.94(4H,m), 7.30–7.34(1H,m), 7.57(1H,dd), 7.59–7.63(2H,m), 7.99–8.04(1H,m)
IR(KBr) cm$^{-1}$: 1720, 1600, 1540, 1435, 1400, 1300, 1280, 1255, 1015, 750, 740

Working Example 70

2-Piperidino-1-[[2'-(1H-tetrazol-5-yl)biphenyl-4-yl]methyl]benzimidazole-7-carboxylic acid The title compound was prepared as colorless crystals from methyl 1-[[2'-(1H-tetrazol-5-yl)biphenyl-4-yl]methyl]-2-piperidinobenzimidazole-7-carboxylate according to the procedure for Working Example 29.

Yield: 91%, m.p.: 215–218° C. (decomp.).

Elemental Analysis for $C_{27}H_{25}N_7O_2 \cdot O5CHCl_3$:

|  | C (%) | H (%) | N (%) |
|---|---|---|---|
| Calcd.: | 61.25; | 4.77; | 18.18 |
| Found: | 60.95; | 4.70; | 17.90 |

$^1$H-NMR(200 MHz,DMSO-d$_6$) δ: 1.65(6H,brs), 3.24(4H,brs), 5.48(2H,s), 6.71(2H,d), 6.92(2H,d), 7.17(1H,t), 7.42–7.48(2H,m), 7.54–7.67(2H,m)
IR(KBr) cm$^{-1}$: 1685, 1530, 1450, 1440, 1420, 1400, 1285, 1270, 1245, 750, 730

Working Example 71

2-Morpholino-1-[[2'-(1H-tetrazol-5-yl)biphenyl-4-yl]methyl]benzimidazole-7-carboxylic acid The title compound was prepared as colorless crystals from methyl 2-morpholino-1-[[2'-(1H-tetrazol-5-yl)biphenyl-4-yl]methyl]benzimidazole-7-carboxylate according to the procedure for Working Example 29.

Yield: 59%, m.p.: 202–206° C. (decomp.).

Elemental Analysis for $C_{26}H_{23}N_7O_3 \cdot O.6CHCl_3$:

|  | C (%) | H (%) | N (%) |
|---|---|---|---|
| Calcd.: | 57.76; | 4.30; | 17.73 |
| Found: | 57.55; | 4.25; | 17.66 |

$^1$H-NMR(200 MHz,DMSO-d$_6$) δ: 3.24(4H,brs), 3.76(4H,brs), 5.56(2H,s), 6.72(2H,d), 6.93(2H,d), 7.16(1H,t), 7.41–7.70(6H,m)
IR(KBr) cm$^{-1}$: 1690, 1535, 1460, 1450, 1420, 1410, 1290, 1260, 1245, 1120, 760, 740

Working Example 72

2-(N-Ethylmethylamino)-1-[[2'-(1H-tetrazol-5-yl)biphenyl-4-yl]methyl]benzimidazole-7-carboxylic acid The title compound was prepared as colorless crystals from methyl 2-(N-ethylmethylamino)-1-[[2'-(1H-tetrazol-5-yl)biphenyl-4-yl]-methyl]benzimidazole-7-carboxylate according to the procedure for Working Example 47.

Yield: 66%, m.p.: 204–206° C. (decomp.).

Elemental Analysis for $C_{25}H_{23}N_7O_2 \cdot O5H_2O$:

|  | C (%) | H (%) | N (%) |
|---|---|---|---|
| Calcd.: | 64.92; | 5.23; | 21.20 |
| Found: | 65.22; | 5.31; | 21.11 |

$^1$H-NMR(200 MHz,CDCl$_3$) δ: 1.13(3H,t), 2.93(3H,s), 3.27(2H,m), 5.54(2H,s), 6.68(2H,d), 6.92(2H,d), 7.13(1H,t), 7.43–7.48(2H,m), 7.53–7.67(2H,m)
IR(KBr) cm$^{-1}$: 1725, 1620, 1550, 1540, 1460, 1440, 1420, 1300, 1250, 775

Working Example 73

2-Butylamino-1-[[2'-(1H-tetrazol-5-yl)biphenyl-4-yl]methyl]-benzimidazole-7-carboxylic acid The title compound was prepared as colorless crystals from methyl 2-butylamino-1-[[2'-(1H-tetrazol-5-yl)biphenyl-4-yl]-methyl]benzimidazole-7-carboxylate according to the procedure for Working Example 47.

Yield: 67%, m.p.: 213–216° C. (decomp.).

Elemental Analysis for $C_{25}H_{25}N_7O_2 \cdot H_2O$:

|  | C (%) | H (%) | N (%) |
|---|---|---|---|
| Calcd.: | 64.32; | 5.60; | 20.19 |
| Found: | 64.07; | 5.77; | 20.16 |

$^1$H-NMR(200 MHz,DMSO-d$_6$) δ: 0.89(3H,t), 1.22–1.41(2H,m), 1.51–1.66(2H,m), 3.34–3.43(2H,m), 5.65(2H,s), 6.83(2H,d), 6.97–7.05(3H,m), 7.29(1H,dd), 7.40–7.67(5H,m)
IR(KBr) cm$^{-1}$: 1660, 1580, 1540, 1485, 1440, 1380, 1340, 1215, 850, 810, 780, 760, 750

Working Example 74

2-Ethoxy-1-[[2'-carboxybiphenyl-4-yl]methyl]benzimidazole-7-carboxylic acid

To a solution of methyl 2-ethoxy-1-[[2'-methoxycarbonylbiphenyl-4-yl]methyl]benzimidazole-7-carboxylate (0.7 g) in methanol (10 ml) was added 1N NaOH (5 ml) and the mixture was stirred at 80° C. for 3 hours. After evaporation of the methanol, the aqueous residue was neutralized with 1N hydrochloric acid to give crystals. The crystals were recrystallized from methanol-chloroform to afford colorless crystals (0.54 g, 83%), m.p. 213–215° C.

Elemental Analysis for $C_{24}H_{20}N_2O_5$:

|  | C (%) | H (%) | N (%) |
|---|---|---|---|
| Calcd.: | 69.22; | 4.84; | 6.73 |
| Found: | 68.98; | 4.89; | 6.71 |

$^1$H-NMR(200 MHz,DMSO-d$_6$) δ: 1.42(3H,t), 4.61(2H,q), 5.68(2H,s), 7.01(2H,d), 7.13–7.56(7H,m), 7.64–7.71(2H,m)
IR(Neat)cm$^{-1}$: 1725, 1545, 1460, 1420, 1380, 7280, 1260, 1230, 1205, 1120, 1030, 750

Working Example 75

Methyl 2-ethylamino-1-[[2'-(1H-tetrazol-5-yl)binhenyl-4-yl]methyl]benzimidazole-7-carboxylate The title compound was prepared as colorless crystals from methyl 2-ethylamino-1-[[2'-cyanobiphenyl-4-yl]

methyl]benzimidazole-7carboxylate according to the procedure for Working Example 41.

Yield: 63%, m.p.: 256–258° C.

Elemental Analysis for $C_{25}H_{23}N_7O_2H_2O$:

|  | C (%) | H (%) | N (%) |
|---|---|---|---|
| Calcd.: | 63.68; | 5.34; | 20.79 |
| Found: | 63.99; | 5.09; | 20.68 |

$^1$H-NMR(200 MHz,DMSO-$d_6$) δ: 1.21(3H,t), 3.40–3.60 (2H,m), 3.63(3H,s), 5.47(2H,s), 6.78(2H,d), 6.98–7.05(3H, m), 7.18(1H,dd), 7.42–7.66(5H,m)
IR(Neat)cm$^{-1}$: 1710, 1660, 1650, 1645, 1430, 1340, 1300, 1280, 1250, 1050, 740

Working Example 76

Methyl 1-[[2'-(1H-tetrazol-5-yl)biphenyl-4-yl] methyl]-2-(2,2,2-trifluoroethoxy)benzimidazole-7-carboxylate The title compound was prepared as colorless needles (0.37 g, 77%) from methyl 1-[[2'-cyanobiphenyl-4-yl] methyl]-2-(2,2,2-trifluoroethoxy)benzimidazole-7-carboxylate (0.48 g) according to the procedure for Working Example 28.

m.p.: 210–212° C.

Elemental Analysis for $C_{25}H_{19}F_3N_6O_3$:

|  | C (%) | H (%) | N (%) |
|---|---|---|---|
| Calcd.: | 59.06; | 3.77; | 16.53 |
| Found: | 59.02; | 3.71; | 16.36 |

$^1$H-NMR(200 MHz,CDCl$_3$) δ: 3.82(3H,s), 5.01(2H,q), 5.64 (2H,s), 6.99(2H,d), 7.14(2H,d), 7.25(1H,t), 7.37–7.41(1H, m), 7.51–7.63(3H,m), 7.71(1H,dd), 8.17–8.22(1H,m)

IR(KBr) cm$^{-1}$: 1710, 1550, 1425, 1275, 1240, 1180, 1160, 1055, 750

Working Example 77

1-[[2'-(1H-tetrazol-5-yl)biphenyl-4-yl]methyl]-2-(2, 2,2-trifluoroethoxy)benzimidazole-7-carboxylic acid The title compound was prepared as colorless crystals (0.23 g, 88%) from methyl 1-[[2'-(1H-tetrazol-5-yl) biphenyl-4-yl]-methyl]-2-(2,2,2-trifluoroethoxy) benzimidazole-7-carboxylate (0.27 g) according to the procedure for Working Example 47.

m.p.: 204–206° C.

Elemental Analysis for $C_{24}H_{17}F_3N_6O_3 \cdot H_2O$:

|  | C (%) | H (%) | N (%) |
|---|---|---|---|
| Calcd.: | 57.26; | 3.60; | 16.69 |
| Found: | 57.09; | 3.59; | 16.72 |

$^1$H-NMR(200 MHz,DMSO-$d_6$) δ: 5.28(2H,q), 5.66(2H,s), 6.98(4H,d), 7.23(1H,t), 7.44–7.68(5H,m), 7.72(1H,dd)

IR(KBr) cm$^{-1}$: 1690, 1540, 1470, 1430, 1270, 1225, 1210, 1160, 1050, 740

The following compounds as listed in Table 1 are prepared according to the procedures for Reference Examples and Working Examples disclosed herein.

TABLE 1

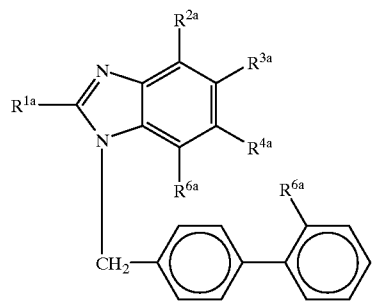

| Compound No. | $R^{1a}$ | $R^{2a}$ | $R^{3a}$ | $R^{4a}$ | $R^{5a}$ | $R^{6a}$ |
|---|---|---|---|---|---|---|
| 78 | OEt | Me | H | H | Tet | COOH |
| 79 | OEt | OMe | H | H | Tet | COOH |
| 80 | OEt | NHMe | H | H | Tet | COOH |
| 81 | OEt | F | H | H | Tet | COOH |
| 82 | OEt | Cl | H | H | Tet | COOH |
| 83 | OEt | Br | H | H | Tet | COOH |
| 84 | OEt | CF$_3$ | H | H | Tet | COOH |
| 85 | OEt | H | Me | H | Tet | COOH |
| 86 | OEt | H | OMe | H | Tet | COOH |
| 87 | OEt | H | NHMe | H | Tet | COOH |
| 88 | OEt | H | F | H | Tet | COOH |

TABLE 1-continued

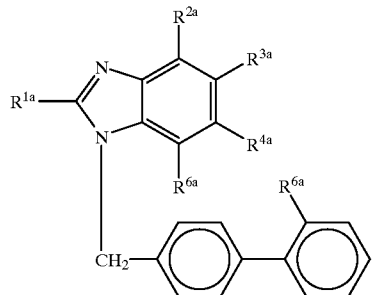

| Compound No. | $R^{1a}$ | $R^{2a}$ | $R^{3a}$ | $R^{4a}$ | $R^{5a}$ | $R^{6a}$ |
|---|---|---|---|---|---|---|
| 89 | OEt | H | Cl | H | Tet | COOH |
| 90 | OEt | H | Br | H | Tet | COOH |
| 91 | OEt | H | CF$_3$ | H | Tet | COOH |
| 92 | OEt | H | H | Me | Tet | COOH |
| 93 | OEt | H | H | OMe | Tet | COOH |
| 94 | OEt | H | H | NHMe | Tet | COOH |
| 95 | OEt | H | H | F | Tet | COOH |
| 96 | OEt | H | H | Cl | Tet | COOH |
| 97 | OEt | H | H | Br | Tet | COOH |
| 98 | OEt | H | H | CF$_3$ | Tet | COOH |
| 99 | OEt | Me | H | H | COOH | COOH |
| 100 | OEt | H | Me | H | COOH | COOH |
| 101 | OEt | H | H | Me | COOH | COOH |
| 102 | OEt | H | H | H | COOH | COOH |
| 103 | OEt | Cl | H | H | COOH | COOH |
| 104 | OEt | H | Cl | H | COOH | COOH |
| 105 | OEt | H | Cl | H | COOH | COOH |
| 106 | SEt | Me | H | H | Tet | COOH |
| 107 | NHMe | H | Me | H | Tet | COOH |
| 108 | OMe | H | H | Me | Tet | COOH |
| 109 | OPr | H | H | Me | Tet | COOH |
| 110 | SMe | Me | H | H | Tet | COOH |
| 111 | OMe | H | H | H | Tet | Tet |
| 112 | OEt | H | H | H | Tet | Tet |
| 113 | OEt | Me | H | H | Tet | Tet |
| 114 | OEt | H |  | | Tet | COOH |
| 115 | OEt | 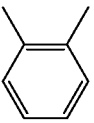 | | H | Tet | COOH |
| 116 | OEt | H | H | H | Tet | COOCH$_2$COO-cyclo-Pr |
| 117 | OEt | H | H | H | Tet | COOCH$_2$COO-sec-Bu |
| 118 | OEt | H | H | H | Tet | COOCH$_2$COO-n-Bu |
| 119 | OEt | H | H | H | Tet | COOCH$_2$COO-cyclo-Bu |
| 120 | OEt | H | H | H | Tet | COOCH$_2$COO-n-Pen |
| 121 | OEt | H | H | H | Tet | COOCH$_2$COO-i-Pen |
| 122 | OEt | H | H | H | Tet | COOCH$_2$COO-sec-Pen |
| 123 | OEt | H | H | H | Tet | COOCH$_2$COO-n-Hex |
| 124 | OEt | H | H | H | Tet | COOCH$_2$COO-sec-Hex |
| 125 | OEt | H | H | H | Tet | COOCH$_2$COO-n-Hep |
| 126 | OEt | H | H | H | Tet | COOCH$_2$OCOCH$_2$Ph |
| 127 | OEt | H | H | H | Tet | COOCH(Me)—OCOEt |
| 128 | OEt | H | H | H | Tet | COOCH(Me)—OCO-n-Pr |
| 129 | OEt | H | H | H | Tet | COOCH(Me)—OCO-i-Pr |
| 130 | OEt | H | H | H | Tet | COOCH(Me)—OCO-cyclo-Pr |
| 131 | OEt | H | H | H | Tet | COOCH(Me)—OCO-n-Bu |
| 132 | OEt | H | H | H | Tet | COOCH(Me)—OCO-i-Bu |
| 133 | OEt | H | H | H | Tet | COOCH(Me)—OCO-sec-Bu |
| 134 | OEt | H | H | H | Tet | COOCH(Me)—OCO-tert-Bu |
| 135 | OEt | H | H | H | Tet | COOCH(Me)—OCO-cyclo-Bu |

TABLE 1-continued

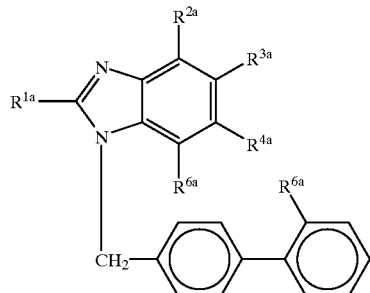

| Compound No. | $R^{1a}$ | $R^{2a}$ | $R^{3a}$ | $R^{4a}$ | $R^{5a}$ | $R^{6a}$ |
|---|---|---|---|---|---|---|
| 136 | OEt | H | H | H | Tet | COOCH(Me)—OCO-n-Pen |
| 137 | OEt | H | H | H | Tet | COOCH(Me)—OCO-i-Pen |
| 138 | OEt | H | H | H | Tet | COOCH(Me)—OCO-sec-Pen |
| 139 | OEt | H | H | H | Tet | COOCH(Me)—OCO-cyclo-Pen |
| 140 | OEt | H | H | H | Tet | COOCH(Me)—OCO-n-Hex |
| 141 | OEt | H | H | H | Tet | COOCH(Me)—OCO-i-Hex |
| 142 | OEt | H | H | H | Tet | COOCH(Me)—OCO-sec-Hex |
| 143 | OEt | H | H | H | Tet | COOCH(Me)—OCO-cyclo-Hex |
| 144 | OEt | H | H | H | Tet | COOCH(Me)—OCO-n-Hep |
| 145 | OEt | H | H | H | Tet | COOCH(Et)—OCO-n-Pr |
| 146 | OEt | H | H | H | Tet | COOCH(Pr)—OCO-n-Bu |
| 147 | OEt | H | H | H | Tet | COOCH(iPr)—OCO-n-Pr |
| 148 | OEt | H | H | H | Tet | COOCH(Me)—OCO—OMe |
| 149 | OEt | H | H | H | Tet | COOCH(Me)—OCO—O-n-Pr |
| 150 | OEt | H | H | H | Tet | COOCH(Me)—OCO—O-i-Bu |
| 151 | OEt | H | H | H | Tet | COOCH(Me)—OCO—O-sec-Bu |
| 152 | OEt | H | H | H | Tet | COOCH(Me)—OCO—O-n-Pen |
| 153 | OEt | H | H | H | Tet | COOCH(Me)—OCO—O-i-Pen |
| 154 | OEt | H | H | H | Tet | COOCH(Me)—OCO—O-cyclo-Pen |
| 155 | OEt | H | H | H | Tet | COOCH(Me)—OCO—O-n-Hex |
| 156 | OEt | H | H | H | Tet | COOCH(Me)—OCO—O-cyclo-Hex |
| 157 | OEt | H | H | H | Tet | COOCH(Me)—OCO—O-cyclo-Hex |
| 158 | OMe | H | H | H | Tet | COOCH$_2$OCO-tert-Bu |
| 159 | OPr | H | H | H | Tet | COOCH$_2$OCO-tert-Bu |
| 160 | OMe | H | H | H | Tet | COOCH(Me)—OCO—O-cyclo-Hex |
| 161 | OPr | H | H | H | Tet | COOCH(Me)—OCO—O-cyclo-Hex |
| 162 | NHEt | H | H | H | Tet | COOCH$_2$OCO-tert-Bu |
| 163 | NHEt | H | H | H | Tet | COOCH$_2$OCO—O-cyclo-Hex |

Experimental Example 1

Figure 2:
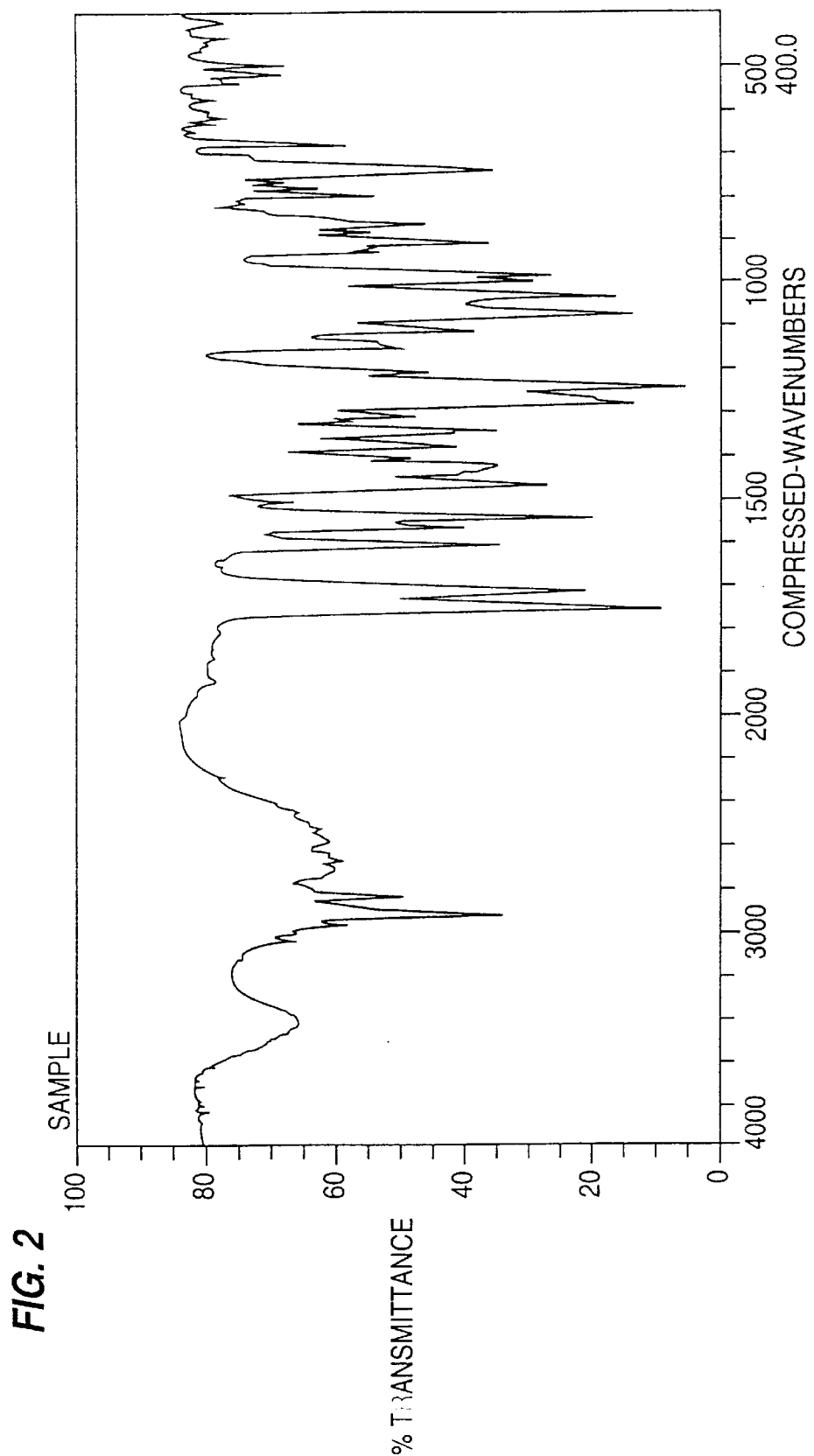
FIG. 2 depicts an IR spectrum pattern obtained in Experimental Example 1.
Figure 3:
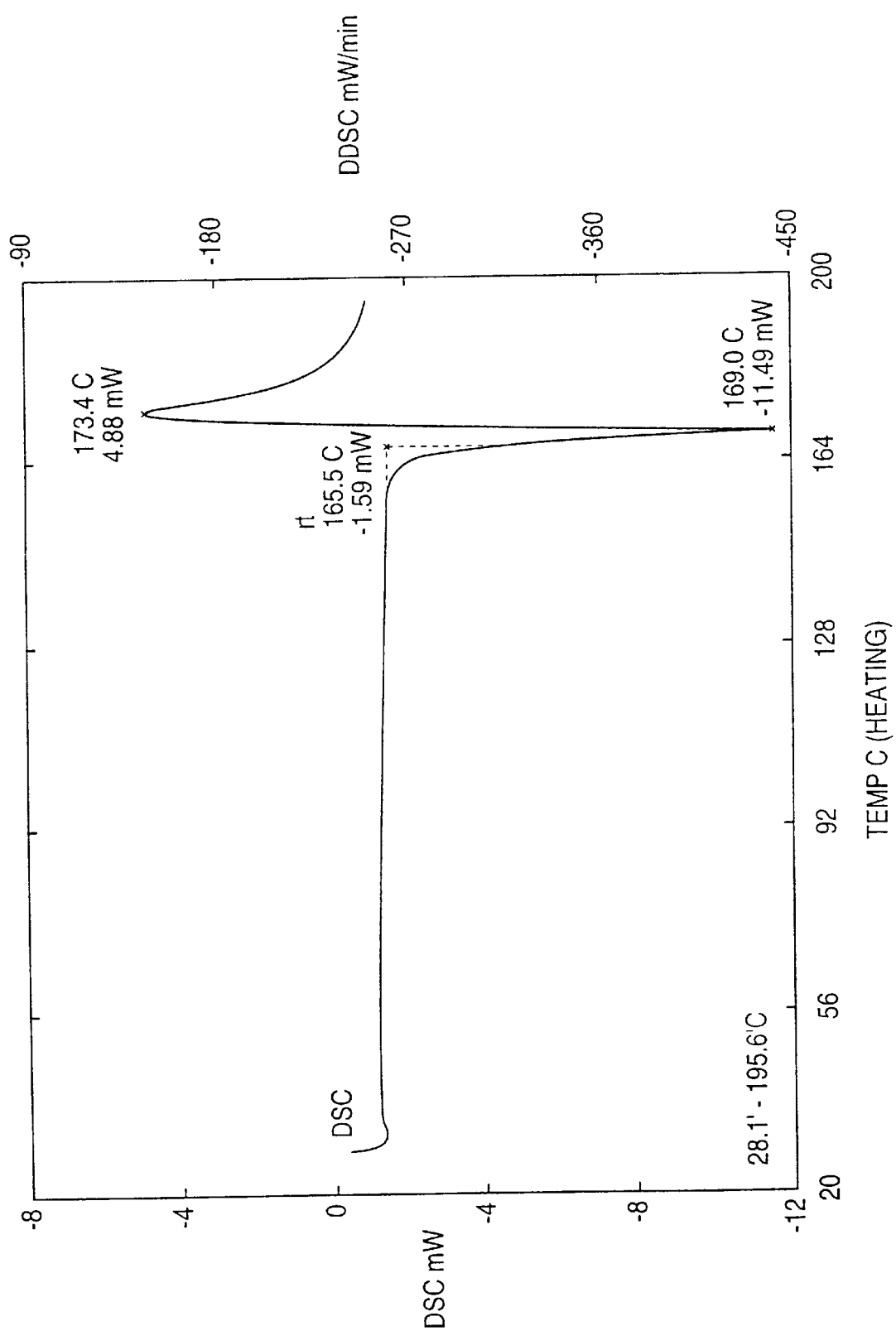
FIG. 3 depicts a differential scanning calorimeter pattern obtained in Experimental Example 1.

Stable C-type crystalline 1-(cyclohexyloxycarbonyloxy)ethyl 2-ethoxy-1-[[2'-(1H-tetrazol-5-yl)biphenyl-4-yl]methyl]-benzimidazole-7-carboxylate and preparation thereof 1-(Cyclohexyloxycarbonyloxy)ethyl 2-ethoxy-1-[[2'-(1H-tetrazol-5-yl)biphenyl-4-yl]methyl]benzimidazole-7-carboxylate is usually purified by column chromatography on silica gel and the eluted fraction is concentrated to dryness to give amorphous powders. The powder is unstable by heat and impractical in production. For solving this problem, the present inventors made extensive experiments on crystallization of the subject compound and discovered C-type crystalline form. The C-type crystal is unexpectedly stable by heat and quite useful for production. The C-type crystal of the title compound has approximately the following lattice spacings:

3.5 angstrom; middle
3.7 angstrom; weak
3.8 angstrom; middle
4.0 angstrom; middle
4.1 angstrom; weak
4.3 angstrom; weak
4.4 angstrom; middle
4.6 angstrom; middle
4.8 angstrom; middle
5.1 angstrom; middle
5.2 angstrom; weak
6.9 angstrom; weak
7.6 angstrom; weak
8.8 angstrom; middle
9.0 angstrom; strong
15.9 angstrom; weak IR spectrum (KBr tablet) of the C-type crystal is shown in FIG. 2 with the significant absorption maxima at 2942, 1754, 1717, 1615, 1549, 1476 and 750 cm$^{-1}$ and its melting point is 158–166° C. (decomposition). Representative X ray chart (powder method), IR spectra (KBr tablet) and differential scanning calorimeter patterns are shown in FIGS. 1–3, respectively.

The C-type crystal of 1-(cyclohexyloxycarbonyloxy) ethyl-2-ethoxy-1-[[2'-(1H-tetrazol-5-yl)biphenyl-4-yl] methyl]-benzimidazole-7-carboxylate has advantages, for example;

1. It improves heat stability and practical utility.

2. Residual solvent can be minimized in crystals.

3. It can achieve industrial and clinical developments and give ecomomical benefits.

The concentrated residues, amorphous powders, and/or crystals except for the C-type crystal for obtaining the subject compound, are stirred in a suitable solvent to form the desired C-type crystal. In case where the C-type crystal is not formed, a small amount of the C-type crystal can be added as a seed to allow crystallization. Examples of such solvents are not limited to, as long as they afford the C-type crystal, but include lower alcohols (e.g. methanol, ethanol, isopropyl alcohol, etc.), a mixture of lower alcohol and water and a mixture of lower alkyl ketone (e.g. acetone, etc.) and water. Amounts of solvents used are not limited to, but practically, 2 to 30-fold per weight of the crystal. Ratios of lower alcohol vs. water and lower alkyl ketone vs. water are not limited to, but preferably 4:1 to 1:1. Stirring temperatures are not limited to, but −5° C. to 40°C., preferably 0° C. to 25° C.

Experimental Example 2

Inhibition of binding of angiotensin II to angiotensin receptor

[Method]

An experiment of inhibition on the binding of angiotensin II (AII) to AII receptor was conducted by modifying the method of Douglas et al. [Endocrinology, 102, 685–696 (1978)]. An A II receptor membrane fraction was prepared from bovine adrenal cortex.

The compound of the present invention ($10^{-6}$ M or $10^{-7}$ M) and $^{125}$I-angiotensin II ($^{125}$I-A II) (1.85 kBq/50 μl) were added to the receptor membrane fraction, and the mixture was incubated at room temperature for one hour. The receptor-bound and free $^{125}$I-A II were separated through a filter (Whataan GF/B filter), and the radioactivity of $^{125}$I-A II bound to the receptor was measured.

[Results]

The results relating to the compounds of the present invention are shown in Table 2.

Experimental Example 3

Inhibitory effect of the compound of the present invention on pressor action of A II

[Method]

Jcl: SD rats (9 week old, male) were employed. On the previous day of the experiment, these animals were applied with cannulation into the femoral artery and vein under anesthesia with pentobarbital Na. The animals were fasted but allowed to access freely to drinking water until the experiment was started. Just on the day of conducting the experiment, the artery cannula was connected with a blood-pressure transducer, and the average blood pressure was recorded by means of polygraph. Before administration of the drug, the pressor action due to intravenous administration of A II (100 ng/kg) as the control was measured. The drugs were orally administered, then, at each point of the measurement, A II was administered intravenously, and the pressor action was similarly measured. By comparing the pressor action before and after administration of the drug, the percent inhibition by the drug on A II-induced pressor action was evaluated.

[Results]

The results relating to the compounds of the present invention are shown in Table 2.

TABLE 2

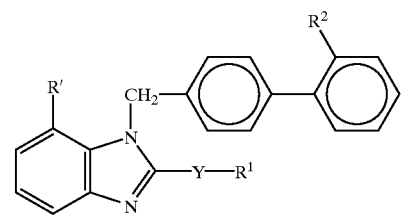

| Working Example No. | $R^1$ | Y | $R^2$ | R' | Radioreceptor Assay $1 \times 10^{-7}$M | $1 \times 10^{-6}$M | Pressor Response to A II(p.o.) 3 mg/kg |
|---|---|---|---|---|---|---|---|
| 28 | Et | O | Tet | COOEt | 46 | 82 | +++ a) |
| 29 | Et | O | Tet | COOH | 61 | 91 | +++ |
| 30 | Pr | O | Tet | COOEt | 16 | 48 | +++ |
| 31 | Pr | O | Tet | COOH | 40 | 79 | +++ |
| 33 | Me | S | Tet | COOEt | 2 | 26 | + |
| 34 | Et | S | Tet | COOEt | 17 | 54 | +++ |
| 35 | Pr | S | Tet | COOEt | 7 | 32 | NT |
| 36 | Me | S | Tet | COOH | 51 | 82 | +++ |
| 37 | Et | S | Tet | COOH | 41 | 80 | +++ |
| 38 | Pr | S | Tet | COOH | 6 | 50 | +++ |
| 39 | Et | O | Tet | COOMe | 58 | 89 | +++ |
| 40 | Et | NH | Tet | COOEt | 54 | 83 | +++ |
| 41 | Pr | NH | Tet | COOEt | 45 | 57 | NT b) |
| 43 | Et | O | Tet | COOCH$_2$OCtBu | 74 | 94 | +++ |

TABLE 2-continued

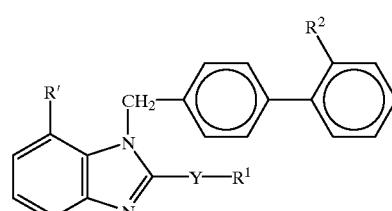

| Working Example No. | R¹ | Y | R² | R' | Radioreceptor Assay $1 \times 10^{-7}$M | $1 \times 10^{-6}$M | Pressor Response to A II(p.o.) 3 mg/kg |
|---|---|---|---|---|---|---|---|
| 44 | Et | O | Tet | 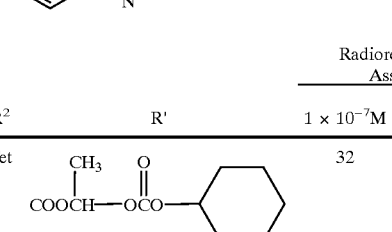 | 32 | 77 | +++ |
| 45 | Me | O | Tet | COOMe | 17 | 67 | +++ |
| 46 | Me | O | Tet | COOH | 66 | 88 | +++ |
| 47 | Et | NH | Tet | COOH | 84 | 96 | +++ |
| 48 | Pr | NH | Tet | COOH | 67 | 92 | ++ |
| 49 | Et | O | Tet | 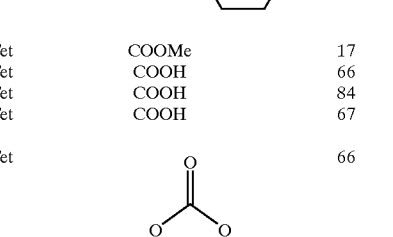 | 66 | 91 | +++ |
| 50 | Et | O | Tet | COOCH₂OCOCH₃ | 63 | 92 | +++ |
| 51 | Et | O | Tet | COOCH₂OCOEt | 44 | 84 | +++ |
| 52 | Et | O | Tet | COOCH₂OCOPr | 48 | 84 | +++ |
| 53 | Et | O | Tet | COOCH₂OCOiPr | 55 | 85 | +++ |
| 54 | Et | O | Tet | 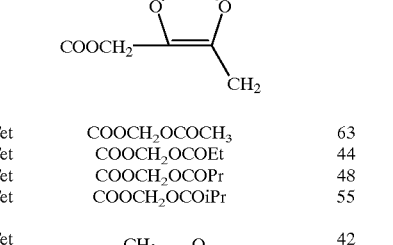 | 42 | 81 | +++ |
| 55 | Et | O | Tet | 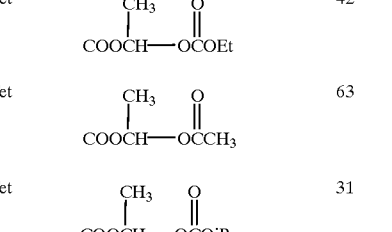 | 63 | 91 | +++ |
| 56 | Et | O | Tet | 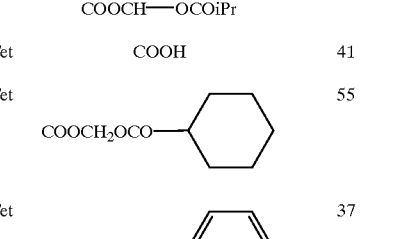 | 31 | 76 | +++ |
| 57 | Me | NH | Tet | COOH | 41 | 79 | NT |
| 58 | Et | O | Tet | 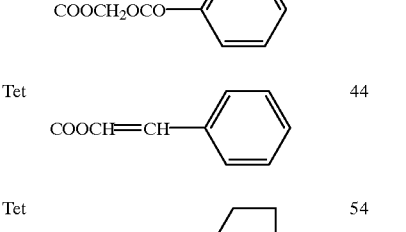 | 55 | 84 | +++ |
| 59 | Et | O | Tet | 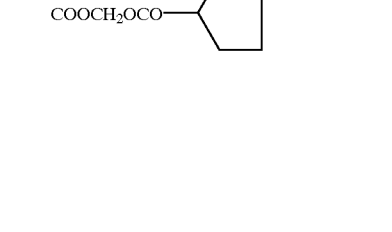 | 37 | 69 | +++ |
| 60 | Et | O | Tet | COOCH=CH—〈phenyl〉 | 44 | 81 | +++ |
| 61 | Et | O | Tet |  | 54 | 89 | +++ |

TABLE 2-continued

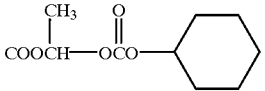

| Working Example No. | $R^1$ | Y | $R^2$ | R' | Radioreceptor Assay $1 \times 10^{-7}$M | $1 \times 10^{-6}$M | Pressor Response to A II(p.o.) 3 mg/kg |
|---|---|---|---|---|---|---|---|
| 62 | Et | NH | Tet | COOCH$_2$OCOtBu | 48 | 87 | +++ |
| 63 | Et | NH | Tet | COOCH(CH$_3$)—OCO—(cyclohexyl) | 19 | 61 | +++ | a) +++ ≧ 70% > ++ ≧ 50% ≧ + > 30% > −
b) NT, not tested

It is understood that the preceding representative examples may be varied within the scope of the present invention by one skilled in the art to achieve essentially the same results.

As many widely different embodiments of this invention may be made without departing from the spirit and scope thereof, it is to be understood that this invention is not limited to the specific embodiments thereof except as defined in the appended claims.

What is claimed is:

1. A compound of the formula:

Scheme A

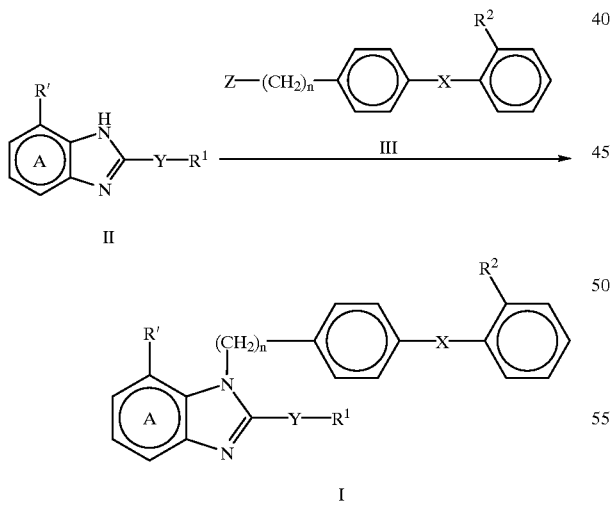

wherein the ring A is a benzene ring which may be substituted or unsubstituted in addition to the R' group; with a substituent selected from the group consisting of 1) halogen; 2) nitro; 3) cyano; 4) amino; 5) N—C$_{1-4}$, alkylamino; 6) N—N—di—C$_{1-4}$alkylamino; 7) phenylamino; 8) naphthylamino; 9) benzylamino; 10) naphthylmethylamino; 11) morpholino; 12) piperidino; 13) piperazino; 14) N-phenylpiperazino;

15) a group having the formula —W—R$^{13}$ wherein W is i) a chemical bond, ii) —O—, iii) —S— or iv) —C(=O)— and R$^{13}$ is i) hydrogen or ii) C$_{1-4}$ alkyl optionally substituted with a) hydroxyl, b) amino, c) dimethylamino, d) diethylamino, e) piperidino, f) morpholino, g) halogen or h) C$_{1-4}$ alkoxy;

16) a group having a formula: —(CH$_2$)$_p$—CO—D wherein p is 0 or 1, and D is i) hydrogen, ii) hydroxyl, iii) amino, iv) N—C$_{1-4}$ alkylamino: v) N—N—di—C$_{1-4}$alkylamino; vi) C$_{1-6}$ alkoxy optionally substituted with a) hydroxyl, b) amino, c) dimethylamino, d) diethylamino, e) piperidino, f) morpholino, g) halogen, h) C$_{1-6}$ alkoxy, i) C$_{1-6}$ alkylthio, j) dioxolenyl or k) 5-methyl-2-oxo-1,3-dioxolen4-yl on the alkyl moiety, or vii) a group having the formula: —OCH(R$^9$) OCOR$^{10}$ wherein R$^9$ is a) hydrogen, b) straight or branched C$_{1-6}$alkyl, c) cyclopentyl, d) cyclohexyl, or e) cycloheptyl, and R$^{10}$ is a) straight or branched C$_{1-6}$alkyl, b) straight or branched C$_{2-8}$alkenyl, c) cyclopentyl, d) cyclohexyl, e) cycloheptyl, f) C$_{1-3}$alkyl which is substituted with phenyl, p-chlorophenyl or C$_{5-7}$cycloalkyl, g) C$_{2-3}$alkenyl which is substituted with phenyl or C$_{5-7}$ cycloalkyl, h) phenyl, i) p-tolyl, j) naphthyl, k) straight or branched C$_{1-6}$alkoxy, l) straight or branched C$_{2-8}$alkenyloxy, m) cyclopentyloxy, n) cyclohexyloxy, o) cycloheptyloxy, p) C$_{1-3}$alkoxy which is substituted with phenyl or C$_{5-7}$cycloalkyl, g) C$_{2-3}$alkenyloxy which is substituted with phenvl or C$_{5-7}$cycloalkyl, r) phenoxy, s) p-nitrophenoxy or t) naphthoxy;

17) tetrazolyl optionally protected with i) C$_{1-4}$alkyl optionally substituted with C$_{1-4}$alkoxy or phenyl, ii) C$_{2-5}$ alkanoyl or iii) benzoyl;

18) trifluoromethanesulfonic amido;

19) phosphono (PO(OH)$_2$); and 20) sulfo (SO$_2$H);

whereby one or two of these substituents may be substituted at various positions of the benzene ring, and whereby when two substituents are present at the 4 and 5 or 5 and 6 positions on the ring A, they may be taken together to form a benzene ring whereby such rings may be substituted with the same groups as for the ring A, $R^1$ is
1) hydrogen:
2) $C_{1-8}$alkalyl, $C_{2-8}$alkenyl, $C_{2-8}$alknyl or $C_{3-6}$cycloalkyl group which groups may be substituted with i) hydroxyl, ii) amino, iii) methylamino iv) halogen or v) $C_{1-4}$alkoxy;
3) phenyl optionally substituted with i) halogen, ii) nitro, iii) $C_{1-4}$alkoxy or $C_{1-4}$alkyl; or
4) phenyl-$C_{1-4}$alkyl optionally substituted with i) haloen, ii) nitro, iii) $C_{1-4}$alkoxy or iv) $C_{1-4}$alkyl on the benzene ring; and $R^2$ is
1) carboxyl;
2) tetrazolyl;
3) trifluoromethanesulfonic amido;
4) phosphono (PO(OH)$_2$);
5) sulfo (SO$_3$H);
6) cyano; or
7) $C_{1-4}$alkoxycarbonyl; each of which may be protected with i) $C_{1-4}$alkyl optionally substituted with $C_{1-4}$alkoxy or phenyl, ii) $C_{2-5}$alkanoyl or iii) benzoyl;

X is a chemical bond, $C_{1-4}$alkylene wherein the number of carbon atoms in the straight chain of said $C_{1-4}$alkylene is 1 or 2, —CO—, —O—, —S—, —NH—, —CONH—, —OCHI—, SCH$_2$— or —CH=CH—;

R' is a group of the formula: —CO—D' wherein D' is hydroxy or lower ($C_{1-6}$) alkoxy optionally substituted with hydroxy, optionally substituted amino, halogen, lower ($C_{1-6}$) alkoxy, lower ($C_{1-6}$) alkylthio or optionally substituted dioxolenyl on the alkyl moiety; Y is —O—, —S(O)$_m$— or —N(R$^4$)— wherein m is an integer of 0, 1 or 2 and R$^4$ is hydrogen or optionally substituted alkyl group, wherein R$^1$ and R$^4$ may be taken together with the N atom to form a ring and n is an integer of 1 or 2; or a pharmaceutically acceptable salt thereof.

2. A compound according to claim 1, wherein R$^1$ is a $C_{1-5}$ alkyl or $C_{2-5}$ alkenyl group optionally substituted with halogen, hydroxyl, an amino group or a $C_{1-4}$ alkoxy group.

3. A compound or a salt thereof according to claim 1, wherein R$^1$ is phenyl which may be substituted with halogen, nitro, $C_{1-4}$ alkoxy, or $C_{1-4}$ alkyl.

4. A compound according to claim 1, wherein R$^1$ is phenyl-$C_{1-4}$ alkyl which may be substituted with halogen, nitro, $C_{1-4}$ alkoxy, or $C_{1-4}$ alkyl.

5. A compound or a salt thereof according to claim 1, wherein R$^2$is a tetrazolyl group optionally protected with $C_{1-4}$ alkyl optionally substituted with $C_{1-4}$ alkoxy or phenyl, $C_{2-5}$ alkanoyl or benzoyl, a carboxyl group optionally protected with $C_{1-4}$ alky optionaly substituted with $C_{1-4}$ alkoxy or phenyl, or trifluoromethanesulfonic amide.

6. A compound or a salt thereof according to claim 1, wherein R$^2$ is a tetrazolyl group.

7. A compound according to claim 1, wherein the ring A is a benzene ring which contains no substitution in addition to the R' group.

8. A compound according to claim 1, wherein X is a chemical bond between the phenylene group and the phenyl group.

9. A compound according to claim 1, which is ethyl 2-propoxy-1-[[2'-(1H-tetrazol-5-yl)biphenyl-4-yl]methyl] benzimidazole-7-carboxylate or a pharmaceutically acceptable salt thereof.

10. A compound according to claim 1, which is 2-propoxy-1-[[2'-(1H-tetrazol-5-yl)biphenyl-4-yl]methyl] benzimidazole-7-carboxylic acid or a pharmaceutically acceptable salt thereof.

11. A compound according to claim 1, which is carboxylate or a pharmaceutically acceptable salt thereof.

12. A compound according to claim 1, which is benzimidazole-7-carboxylate or a pharmaceutically acceptable salt thereof.

13. A compound according to claim 1, which is benzimidazole-7-carboxylate or a pharmaceutically acceptable salt thereof.

14. A compound according to claim 1, which is 2-methylthio-1-[[2'-(1H-tetrazol-5-yl)biphenyl-4-yl] methyl]benzimidazole-7-carboxylic acid or a pharmaceutically acceptable salt thereof.

15. A compound according to claim 1, which is 2-ethylthio-1-[[2'-(1H-tetrozol-5-yl)biphenyl-4-yl]methyl] benzimidazole-7-carboxylic acid or a pharmaceutically acceptable salt thereof.

16. A compound according to claim 1, which is 2-propylthio-1-[[2'-(1H-tetrazol-5-yl)biphenyl-4-yl]methyl] bennzimidazole-7-carboxylic acid or a pharmaceutically acceptable salt thereof.

17. A compound according to claim 1, which is ethyl 2-ethylamino-1-benzimidazole-7-carboxylate or a pharmaceutically acceptable salt thereof.

18. A compound according to claim 1, which is ethyl 2-propylamino-1-benzimidazole-7-carboxylate or a pharmaceutically acceptable salt thereof.

19. A compound according to claim 1, which is methyl 2-methoxy-1-benzimidazole-7 carboxylate acid or a pharmaceutically acceptable salt thereof.

20. A compound according to claim 1, which is 2-methoxy-1-[[2'-(1H-tetrazol-5-yl)biphenyl-4-yl]methyl] benzimidazole-7-carboxylic acid or a pharmaceutically acceptable salt thereof.

21. A compound according to claim 1, which is 2-ethylamino-1-[[2'-(1H-tetrazol-5-yl)biphenyl-4-yl] methyl]benzimidazole-7-carboxylic acid or a pharmaceutically acceptable salt thereof.

22. A compound according to claim 1, which is 2-propylamino-1-benzamidzaole-7-carboxylic acid or a pharmaetuecitcallu acceptable salt thereof.

23. A compound according to claim 1, which is (5-methyl-2-oxo-1,3-dioxolen-4-yl)methyl 2-ethoxy-1-benzyimdaloze-7-carboxlate or a pharmaceutically acceptable salt thereof.

24. A pharmaceutical composition for antagonizing angiotensin II which comprises a therapeutically effective amount of a compound according to claim 1 or a pharmaceutically acceptable salt thereof in admixture with a pharmaceutically acceptable carrier, excipient or diluent.

25. A method for antagonizing angiotensin II in a mammal which comprises administering to a mammal in need thereof a therapeutically effective amount of a compound according to claim 1 or a pharmaceutically acceptable salt thereof.

* * * * *

UNITED STATES PATENT AND TRADEMARK OFFICE
CERTIFICATE OF CORRECTION

PATENT NO. : 6,232,334 B1
DATED : May 15, 2001
INVENTOR(S) : Takehiko Naka et al.

It is certified that error appears in the above-identified patent and that said Letters Patent is hereby corrected as shown below:

Column 71, lines 26-67, Column 72, lines 26-67 through Column 73, lines 1-40, Should read:

1. A compound of the formula:

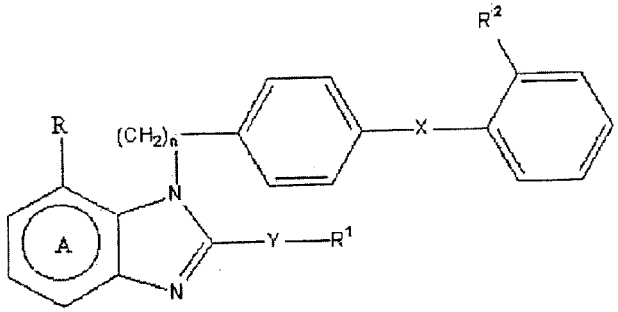

wherein the ring A is a benzene ring which may be substituted or unsubstituted in addition to the R' group; with a substituent selected from the group consisting of 1) halogen; 2) nitro; 3) cyano; 4) amino; 5) N-$C_{1-4}$ alkylamino; 6) N-N-di-$C_{1-4}$ alkylamino;

7) phenylamino; 8) naphthylamino; 9) benzylamino; 10) naphthylmethylamino; 11) morpholino; 12) piperidino; 13) piperazino; 14) N-phenylpiperazino;

15) a group having the formula -W-$R^{13}$ wherein W is i) a chemical bond, ii) -O-, iii) -S- or iv) -C(=O)- and $R^{13}$ is i) hydrogen or ii) $C_{1-4}$ alkyl optionally substituted with a) hydroxyl, b) amino, c) dimethylamino, d) diethylamino, e) piperidino, f) morpholino, g) halogen or h) $C_{1-4}$ alkoxy;

16) a group having a formula: -$(CH_2)_p$-CO-D wherein p is 0 or 1, and D is i) hydrogen, ii) hydroxyl, iii) amino, iv) N-$C_{1-4}$ alkylamino, v) N-N-di-$C_{1-4}$ alkylamino, vi) $C_{1-6}$ alkoxy optionally substituted with a) hydroxyl, b) amino, c) dimethylamino, d) diethylamino, e) piperidino, f) morpholino, g) halogen, h) $C_{1-6}$ alkoxy, i) $C_{1-6}$ alkylthio, j) dioxolenyl, or k) 5-methyl-2-oxo-1,3-dioxolen-4-yl on the alkyl moiety, or vii) a group having the formula: -OCH($R^9$) OCOR$^{10}$ wherein $R^9$ is a) hydrogen, b) straight or branched $C_{1-6}$ alkyl, c) cyclopentyl, d) cyclohexyl, or e) cycloheptyl, and

UNITED STATES PATENT AND TRADEMARK OFFICE
CERTIFICATE OF CORRECTION

PATENT NO. : 6,232,334 B1
DATED : May 15, 2001
INVENTOR(S) : Takehiko Naka et al.

It is certified that error appears in the above-identified patent and that said Letters Patent is hereby corrected as shown below:

$R^{10}$ is a) straight or branched $C_{1-6}$ alkyl, b) straight or branched $C_{2-8}$ alkenyl, c) cyclopentyl, d) cyclohexyl, e) cycloheptyl, f) $C_{1-3}$ alkyl which is substituted with phenyl, p-chlorophenyl or $C_{5-7}$ cycloalkyl, g) $C_{2-3}$ alkenyl which is substituted with phenyl or $C_{5-7}$ cycloalkyl, h) phenyl, i) p-tolyl, j) naphthyl, k) straight or branched $C_{1-6}$ alkoxy, l) straight or branched $C_{2-8}$ alkenyloxy, m) cyclopentyloxy, n) cyclohexyloxy, o) cycloheptyloxy, p) $C_{1-3}$ alkoxy which is substituted with phenyl or $C_{5-7}$ cycloalkyl, q) $C_{2-3}$ alkenyloxy which is substituted with phenyl or $C_{5-7}$ cycloalkyl, r) phenoxy, s) p-nitrophenoxy or t) naphthoxy;

17) tetrazolyl optionally protected with i) $C_{1-4}$ alkyl optionally substituted with $C_{1-4}$ alkoxy or phenyl, ii) $C_{2-5}$ alkanoyl or iii) benzoyl;

18) trifluoromethanesulfonic amido;

19) phosphono ($PO(OH)_2$); and 20) sulfo ($SO_3H$);

whereby one or two of these substituents may be substituted at various positions of the benzene ring, and whereby when two substituents are present at the 4 and 5 or 5 and 6 positions on the ring A, they may be taken together to form a benzene ring whereby such rings may be substituted with the same groups as for the ring A, $R^1$ is 1) hydrogen;

2) $C_{1-8}$ alkyl, $C_{2-8}$ alkenyl, $C_{2-8}$ alkynyl or $C_{3-6}$ cycloalkyl group which groups may be substituted with i) hydroxyl, ii) amino, iii) methylamino, iv) halogen or v) $C_{1-4}$ alkoxy;

3) phenyl optionally substituted with i) halogen, ii) nitro, iii) $C_{1-4}$ alkoxy or $C_{1-4}$ alkyl; or 4) phenyl-$C_{1-4}$ alkyl optionally substituted with i) halogen, ii) nitro, iii) $C_{1-4}$ alkoxy or iv) $C_{1-4}$ alkyl on the benzene ring; and $R^2$ is 1) carboxyl;

2) tetrazolyl;

3) trifluoromethanesulfonic amido;

UNITED STATES PATENT AND TRADEMARK OFFICE
CERTIFICATE OF CORRECTION

PATENT NO. : 6,232,334 B1
DATED : May 15, 2001
INVENTOR(S) : Takehiko Naka et al.

It is certified that error appears in the above-identified patent and that said Letters Patent is hereby corrected as shown below:

4) phosphono ($PO(OH)_2$);

5) sulfo ($SO_3H$);

6) cyano; or

7) $C_{1-4}$ alkoxycarbonyl; each of which may be protected with i) $C_{1-4}$ alkyl optionally substituted with $C_{1-4}$ alkoxy or phenyl, ii) $C_{2-5}$ alkanoyl or iii) benzoyl;

X is a chemical bond, $C_{1-4}$ alkylene wherein the number of carbon atoms in the straight chain of said $C_{1-4}$ alkylene is 1 or 2, -CO-, -O-, -S-, -NH-, -CONH-,-OCH$_2$-, SCH$_2$- or -CH=CH-;

R' is a group of the formula: -CO-D' wherein D' is hydroxy or lower ($C_{1-6}$) alkoxy optionally substituted with hydroxy, optionally substituted amino, halogen, lower ($C_{1-6}$) alkoxy, lower ($C_{1-6}$) alkylthio or optionally substituted dioxolenyl on the alkyl moiety;

Y is -O-, -S(O)$_m$- or -N(R$^4$)- wherein m is an integer of 0, 1 or 2 and R$^4$ is hydrogen or optionally substituted alkyl group, wherein R$^1$ and R$^4$ may be taken together with the N atom to form a ring and n is an integer of 1 or 2; or a pharmaceutically acceptable salt thereof.

Column 74,
Lines 9-52 should read:

11. A compound according to claim 1, which is ethyl 2-methylthio-1-[[2'-(1H-tetrazol-5-yl)biphenyl-4-yl]methyl]benzimidazole-7-carboxylate or a pharmaceutically acceptable salt thereof.

12. A compound according to claim 1, which is ethyl 2-ethylthio-1-[[2'-(1H-tetrazol-5-yl)biphenyl-4-yl]methyl]benzimidazole-7-carboxylate or a pharmaceutically acceptable salt thereof.

13. A compound according to claim 1, which is ethyl 2-propylthio-1-[[2'-(1H-tetrazol-5-yl)biphenyl-4-yl]methyl]benzimidazole-7-carboxylate or a pharmaceutically acceptable salt thereof.

16. A compound according to claim 1, which is 2-propylthio-1-[[2'-(1H-tetrazol-5-yl)biphenyl-4-yl]methyl]benzimidazole-7-carboxylic acid or a pharmaceutically acceptable salt thereof.

UNITED STATES PATENT AND TRADEMARK OFFICE
CERTIFICATE OF CORRECTION

PATENT NO. : 6,232,334 B1
DATED : May 15, 2001
INVENTOR(S) : Takehiko Naka et al.

It is certified that error appears in the above-identified patent and that said Letters Patent is hereby corrected as shown below:

17. A compound according to claim 1, which is ethyl 2-ethylamino-1-[[2'-(1H-tetrazol-5-yl)biphenyl-4-yl]methyl]benzimidazole-7-carboxylate or a pharmaceutically acceptable salt thereof.

18. A compound according to claim 1, which is ethyl 2-propylamino-1-[[2'-(1H-tetrazol-5-yl)biphenyl-4-yl]methyl]benzimidazole-7-carboxylate or a pharmaceutically acceptable salt thereof.

19. A compound according to claim 1, which is methyl 2-methoxy-1-[[2'-(1H-tetrazol-5-yl)biphenyl-4-yl]methyl]benzimidazole-7-carboxylate or a pharmaceutically acceptable salt thereof.

22. A compound according to claim 1, which is 2-propylamino-1-[[2'-(1H-tetrazol-5-yl)biphenyl-4-yl]methyl]benzimidazole-7-carboxylic acid or a pharmaceutically acceptable salt thereof.

23. A compound according to claim 1, which is (5-methyl-2-oxo-1,3-dioxolen-4-yl)methyl 2-ethoxy-1-[[2'-(1H-tetrazol-5-yl)biphenyl-4-yl]methyl]benzimidazole-7-carboxylate or a pharmaceutically acceptable salt thereof.

Signed and Sealed this

Twenty-eighth Day of January, 2003

JAMES E. ROGAN
*Director of the United States Patent and Trademark Office*